US012419870B2

(12) United States Patent
Rosen et al.

(10) Patent No.: US 12,419,870 B2
(45) Date of Patent: *Sep. 23, 2025

(54) COMPOSITIONS AND METHODS FOR IMMUNE CELL MODULATION IN ADOPTIVE IMMUNOTHERAPIES

(71) Applicant: Fate Therapeutics, Inc., San Diego, CA (US)

(72) Inventors: Jonathan Rosen, San Diego, CA (US); Betsy Rezner, San Diego, CA (US); Bahram Valamehr, San Diego, CA (US); Ryan Bjordahl, San Diego, CA (US); Eigen Peralta, San Diego, CA (US); Ian Hardy, San Diego, CA (US)

(73) Assignee: Fate Therapeutics, Inc., San Diego, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 17/861,042

(22) Filed: Jul. 8, 2022

(65) Prior Publication Data

US 2022/0401487 A1     Dec. 22, 2022

Related U.S. Application Data

(63) Continuation of application No. 16/071,460, filed as application No. PCT/US2017/014449 on Jan. 20, 2017, now Pat. No. 11,413,309.

(Continued)

(51) Int. Cl.
*A61K 31/436*     (2006.01)
*A61K 35/28*     (2015.01)
(Continued)

(52) U.S. Cl.
CPC ............ *A61K 31/436* (2013.01); *A61K 35/28* (2013.01); *A61K 35/545* (2013.01); *A61K 38/09* (2013.01);
(Continued)

(58) Field of Classification Search
CPC .................................................... A61K 31/436
See application file for complete search history.

(56) References Cited

U.S. PATENT DOCUMENTS 8,044,201 B2    10/2011  Xu et al.
9,233,125 B2     1/2016  Davila et al.
(Continued)

FOREIGN PATENT DOCUMENTS

CN      102027105 A     4/2011
EP        2303319 A2    4/2011
(Continued)

OTHER PUBLICATIONS

Nikiforow 2013 Biol Blood Marow Transplant Abstract 187 (Year: 2013).*

(Continued)

*Primary Examiner* — Mark L Shibuya
(74) *Attorney, Agent, or Firm* — Greenberg Traurig, LLP

(57) ABSTRACT

Compounds that either produced a higher proportion or greater absolute number of phenotypically identified nave, stem cell memory, central memory T cells, adaptive NK cells, and type I NKT cells are identified. Compositions and methods for modulating immune cells including T, NK, and NKT cells for adoptive cell therapies with improved efficacy are provided.

16 Claims, 18 Drawing Sheets

Related U.S. Application Data

(60) Provisional application No. 62/402,883, filed on Sep. 30, 2016, provisional application No. 62/281,064, filed on Jan. 20, 2016.

(51) Int. Cl.

| | |
|---|---|
| A61K 35/545 | (2015.01) |
| A61K 38/09 | (2006.01) |
| A61K 38/14 | (2006.01) |
| A61K 38/21 | (2006.01) |
| A61K 38/50 | (2006.01) |
| A61K 40/11 | (2025.01) |
| A61K 40/31 | (2025.01) |
| A61K 40/42 | (2025.01) |
| A61K 45/06 | (2006.01) |
| C07K 14/725 | (2006.01) |
| C12N 5/0783 | (2010.01) |

(52) U.S. Cl.
CPC ............ *A61K 38/14* (2013.01); *A61K 38/212* (2013.01); *A61K 38/50* (2013.01); *A61K 40/11* (2025.01); *A61K 40/31* (2025.01); *A61K 40/42* (2025.01); *C07K 14/7051* (2013.01); *C12N 5/0636* (2013.01); *A61K 45/06* (2013.01); *A61K 2239/31* (2023.05); *A61K 2239/38* (2023.05); *C12N 2510/00* (2013.01); *Y02A 50/30* (2018.01)

(56) References Cited

U.S. PATENT DOCUMENTS

| | | |
|---|---|---|
| 9,376,664 B2 | 6/2016 | Efe et al. |
| 9,556,271 B2 | 1/2017 | Efe et al. |
| 9,828,399 B2 | 11/2017 | Tremblay et al. |
| 11,096,964 B2 | 8/2021 | Rosen et al. |
| 11,413,309 B2 | 8/2022 | Rosen et al. |
| 11,859,003 B2 | 1/2024 | Luo et al. |
| 11,932,870 B2 | 3/2024 | Rosen et al. |
| 2001/0053361 A1 | 12/2001 | Thompson et al. |
| 2004/0175373 A1 | 9/2004 | Berenson et al. |
| 2005/0075276 A1 | 4/2005 | Rudd |
| 2006/0247214 A1 | 11/2006 | DeLong et al. |
| 2016/0009813 A1 | 1/2016 | Themeli et al. |
| 2017/0296659 A1 | 10/2017 | Lebwohl et al. |
| 2018/0072992 A1 | 3/2018 | Valamehr et al. |
| 2018/0243341 A1 | 8/2018 | June et al. |
| 2018/0320137 A1 | 11/2018 | Valamehr et al. |
| 2019/0125795 A1 | 5/2019 | Rosen et al. |
| 2019/0282618 A1 | 9/2019 | Rosen et al. |
| 2020/0181573 A1 | 6/2020 | Rosen et al. |
| 2021/0393695 A1 | 12/2021 | Rosen et al. |

FOREIGN PATENT DOCUMENTS

| | | |
|---|---|---|
| EP | 2638896 A1 | 3/2012 |
| GB | 2 444 853 A | 6/2008 |
| GB | 2 444 853 B | 6/2008 |
| JP | 2019-502725 A | 1/2019 |
| WO | WO 99/01426 A1 | 1/1999 |
| WO | WO 01/12596 A1 | 2/2001 |
| WO | WO 02/06213 A2 | 1/2002 |
| WO | WO 02/06213 A3 | 1/2002 |
| WO | WO 03/077914 A1 | 9/2003 |
| WO | WO 2005/051301 A2 | 6/2005 |
| WO | WO 2005/051301 A3 | 6/2005 |
| WO | WO 2007/044084 A2 | 4/2007 |
| WO | WO 2007/044084 A3 | 4/2007 |
| WO | WO 2007/103901 A2 | 9/2007 |
| WO | WO 2007/103901 A3 | 9/2007 |
| WO | WO 2008/006583 A1 | 1/2008 |
| WO | WO 2009/117439 A2 | 9/2009 |
| WO | WO 2009/155535 A2 | 12/2009 |
| WO | WO 2010/083298 A1 | 7/2010 |
| WO | WO 2015/155738 A2 | 10/2015 |
| WO | WO 2015/155738 A3 | 10/2015 |
| WO | WO 2015/160986 A2 | 10/2015 |
| WO | WO 2015/160986 A3 | 10/2015 |
| WO | WO 2015/188119 * | 12/2015 ............ A01N 63/00 |
| WO | WO 2015/188119 A1 | 12/2015 |
| WO | WO 2016/040892 A1 | 3/2016 |
| WO | WO 2016/123100 A1 | 8/2016 |
| WO | WO 2016/123117 A1 | 8/2016 |
| WO | WO 2016/160621 A2 | 10/2016 |
| WO | WO 2016/160621 A3 | 10/2016 |
| WO | WO 2016/179283 A1 | 11/2016 |
| WO | WO 2016/187158 A1 | 11/2016 |
| WO | WO 2017/078807 A1 | 5/2017 |
| WO | WO 2017/078807 A9 | 5/2017 |
| WO | WO 2017/127729 A1 | 7/2017 |
| WO | WO 2017/127755 A1 | 7/2017 |
| WO | WO 2018/231951 A1 | 12/2018 |

OTHER PUBLICATIONS

Wu 2014 Transplantation Abstract D2799 (Year: 2014).*

Aoukaty, A. et al. (Apr. 15, 2005). "Role for glycogen synthase kinase-3 in NK cell cytotoxicity and X-linked lymphoproliferative disease," *J. Immunol.*, 174(8):4551-4558.

Araki, K. et al. (Jul. 2, 2009, e-published Jun. 21, 2009). "mTOR regulates memory CD8 T-cell differentiation," *Nature*, 460(7251):108-112.

Araki, K. et al. (May 2010). "The role of mTOR in memory CD8 T-cell differentiation," *Immunol Rev* 235(1):234-243.

Asanuma, S. et al. (Jun. 2011, e-published Nov. 24, 2010). "Expansion of CD4(+)CD25 (+) regulatory T cells from cord blood CD4(+) cells using the common γ-chain cytokines (IL-2 and IL-15) and rapamycin," *Ann Hematol* 90(6):617-624.

Battaglia, M. et al. (Jun. 15, 2005, e-published Mar. 3, 2005). "Rapamycin selectively expands CD4+CD25+FoxP3+ regulatory T cells," *Blood* 105(12):4743-4748.

Berger, C. et al. (Jan. 2008). "Adoptive transfer of effector CD8+ T cells derived from central memory cells establishes persistent T cell memory in primates," *J. Clin. Invest.*, 118(1):294-305.

Cao et al., "Metabolic reprogramming towards aerobic glycolysis correlates with greater proliferative ability and resistance to metabolic inhibition in CD8 versus CD4 T cells," *PLoS One*, 9(8):e104104 (2014).

Chang, C.H. et al. (Jun. 6, 2013). "Posttranscriptional control of T cell effector function by aerobic glycolysis," *Cell*, 153(6):1239-1251.

Cheng, M. et al. (May 2013, e-published Apr. 22, 2013). "NK cell-based immunotherapy for malignant diseases," *Cell Mol. Immunol.*, 10(3):230-252.

Esteban, M.A. et al. (Jan. 8, 2010, e-published Dec. 31, 2009). "Vitamin C enhances the generation of mouse and human induced pluripotent stem cells," *Cell Stem Cell* 6(1):71-79.

Fate Therapeutics Announces Observed Effects of Pharmacologic Modulation on T Cell Compartment From Its Phase 1b Study of Prohema(R) (Feb. 26, 2014). located at <http://ir.fatetherapeutics.com/releasedetail.cfm?releaseid=828400> 2 pages.

Feng, B. et al. (Apr. 3, 2009). "Molecules that promote or enhance reprogramming of somatic cells to induced pluripotent stem cells," *Cell Stem Cell* 4(4):301-312.

Goessling, W. et al. (Apr. 8, 2011). "Prostaglandin E2 enhances human cord blood stem cell xenotransplants and shows long-term safety in preclinical nonhuman primate transplant models," *Cell Stem Cell* 8(4):445-458.

Goldman et al., "Immunology Overview," *Medical Microbiology, 4th Edition*, Baron ed., University of Texas Medical Branch at Galveston, pp. 1-48 (1996).

Huangfu, D et al. (Jul. 2008, e-published Jun. 22, 2008). "Induction of pluripotent stem cells by defined factors is greatly improved by small-molecule compounds," *Nat Biotechnol* 26(7):795797.

Huangfu, D et al. (Nov. 2008, e-published Oct. 12, 2008). "Induction of pluripotent stem cells from primary human fibroblasts with only Oct4 and Sox2," *Nat Biotechnol* 26(11):1269-1275.

(56) References Cited

OTHER PUBLICATIONS

Ichida, J.K. et al. (Nov. 6, 2009, e-published Oct. 8, 2009). "A small-molecule inhibitor of tgf-Beta signaling replaces sox2 in reprogramming by inducing nanog," *Cell Stem Cell* 5(5):491-503.
Inman, G.J. et al. (Jul. 2002). "SB-431542 is a potent and specific inhibitor of transforming growth factor-beta superfamily type I activin receptor-like kinase (ALK) receptors ALK4, ALK5, and ALK7," *J Mol. Pharmacol.* 62(1):65-74.
Kim, D. et al. (Jun. 5, 2009, e-published May 28, 2009). "Generation of human induced pluripotent stem cells by direct delivery of reprogramming proteins," *Cell Stem Cell*, 4(6):472-476.
Kim, G.G. et al. (Aug. 31, 2007, e-published Jun. 28, 2007). "A novel multiparametric flow cytometry-based cytotoxicity assay simultaneously immunophenotypes effector cells: comparisons to a 4 h 51Cr-release assay," *J. Immunol. Methods*, 325(1-2):51-66.
King, C.C. et al. (Jun. 16, 2000). "Sphingosine is a novel activator of 3-phosphoinositide-dependent kinase 1," *Journal of Biological Chemistry* 275(24):1810818113.
Liu, Y. et al. (Jan. 2015, e-published Jul. 14, 2014). "mTOR signaling in T cell immunity and autoimmunity," *Int Rev Immunol* 34(1):50-66.
Lyssiotis, C.A. et al. (Jun. 2, 2009, e-published May 15, 2009). "Reprogramming of murine fibroblasts to induced pluripotent stem cells with chemical complementation of Klf4," *PNAS USA* 106(22):8912-8917.
Mack et al., "Generation of induced pluripotent stem cells from CD34+ cells across blood drawn from multiple donors with non-integrating episomal vectors," *PLoS One*, 6(11):e27956 (2011).
Maherali, N. et al. (Nov. 3, 2009, e-published Sep. 17, 2009). "Tgfβ signal inhibition cooperates in the induction of iPSCs and replaces Sox2 and cMyc," *Curr Biol* 19(20):1718-1723.
Nerreter et al., "Combining dasatinib with dexamethasone long-term leads to maintenance of antiviral and antileukemia specific cytotoxic T cell responses in vitro," *Exp. Hematol.*, 41(7):604-614 (2013).
Nikiforow et al., "Evolution of T Cell Repertoire Diversity After Reduced-Intensity Conditioning and Double Umbilical Cord Blood Transplantation with or without Exposure to FT1050 (16, 16-dimethyl Prostaglandin E2)" *Biol. Blood Marrow Transplant.*, 19(2):S206-S207, Abstract No. 187 (2013).
Parameswaran et al., "Repression of GSK3 restores NK cell cytotoxicity in AML patients," *Nature Commun.*, 7:1154 (2016).
Perkins, M.R. et al. (Dec. 3, 2015). "Manufacturing an Enhanced CAR T Cell Product By Inhibition of the PI3K/Akt Pathway During T Cell Expansion Results in Improved In Vivo Efficacy of Anti-BCMA CAR T Cells," *Blood* 126(23): 3 pages..
Robson et al., "Optimal effector functions in human natural killer cells rely upon autocrine bone morphogenetic protein signaling," *Cancer Res.*, 74(18):5019-5031 (2014).
Rosen, J. et al. (Dec. 2, 2016). "Identification of small molecule modulators to enhance the therapeutic properties of chimeric antigen receptor T cells," *Blood* 128:4712.
Roskoski et al., "Properties of FDA-approved small molecule protein kinase inhibitors," *Pharmacol. Res.*, 144:19-50 (2019).
Rossari et al., "Past, present, and future of Bcr-Abl inhibitors: from chemical development to clinical efficacy," *J. Hematol. Oncol.*, 11:84 (2018).
Rutishauser, R.L. et al. (Aug. 21, 2009, e-published Aug. 6, 2009). "Transcriptional repressor Blimp-1 promotes CD8(+) T cell terminal differentiation and represses the acquisition of central memory T cell properties," *Immunity* 31(2): 296-308.
Saha, K. et al. (Dec. 4, 2009). "Technical challenges in using human induced pluripotent stem cells to model disease," *Cell Stem Cell* 5(6):584-595.
Schwarzbich et al., "The immune inhibitory receptor osteoactivin is upregulated in monocyte-derived dendritic cells by BCR-ABL tyrosine kinase inhibitors," *Cancer Immunol. Immunother.*, 61:193-202 (2012).
Shi, Y. et al. (Jun. 5, 2008). "A combined chemical and genetic approach for the generation of induced pluripotent stem cells," *Cell Stem Cell* 2(6):525-528.
Shi, Y. et al. (Nov. 6, 2008). "Induction of pluripotent stem cells from mouse embryonic fibroblasts by Oct4 and Klf4 with small-molecule compounds," *Cell Stem Cell* 3(5):568-574.
Silva, J. et al. (Oct. 21, 2008). "Promotion of reprogramming to ground state pluripotency by signal inhibition," *PloS Biol* 6(10):e253.
Sommermeyer, D. et al. (Feb. 2016, e-published Sep. 15, 2015). "Chimeric antigen receptor-modified T cells derived from defined CD8+ and CD4+ subsets confer superior antitumor reactivity in vivo," *Leukemia* 30(2):492-500.
Sukumar, M. et al. (Oct. 2013, Sep. 16, 2013). "Inhibiting glycolytic metabolism enhances CD8+ T cell memory and antitumor function," *J Clin Invest.* 123(10):4479-4488.
Takahashi, K. et al. (Aug. 25, 2006, e-published Aug. 10, 2006). "Induction of pluripotent stem cells from mouse embryonic and adult fibroblast cultures by defined factors," *Cell* 126(4):663-676.
Takahashi, K. et al. (Nov. 30, 2007). "Induction of pluripotent stem cells from adult human fibroblasts by defined factors," *Cell* 131(5):861-872.
Wai, L-E. et al. (Jan. 15, 2008). "Rapamycin, but not cyclosporine or FK506, alters natural killer cell function," *Transplantation*, 85(1):145-149.
Wolleschak et al., "FLT3-Kinase Inhibitors Quizartinib and Midostaurin Do Not Impair T-Cell Reactivity and Activation," *Blood*, 120(21):1045 (2012).
Wu et al., "Rapamycin Promotes Expansion of CD4+CD25+FOXP3+ Regulatory T Cells by Modulating Fatty Acid Metabolism," *Transplantation*, 98(Suppl 1):402, Abstract D2799 (2014).
Yamanaka, S. et al. (Jul. 2, 2009). "Elite and stochastic models for induced pluripotent stem cell generation," *Nature* 460(7251):49-52.
Yu, J. et al. (Dec. 21, 2007, e-published Nov. 20, 2007). "Induced pluripotent stem cell lines derived from human somatic cells," *Science* 318(5858):1917-1920.
Zhang, J.Y. et al. (Jan. 10, 2018). "Modulation of CD8 + memory stem T cell activity and glycogen synthase kinase 3β inhibition enhances anti-tumoral immunity in gastric cancer," *Oncoimmunology* 7(4):e1412900.
Zhou, H. et al. (May 8, 2009, e-published Apr. 23, 2009). "Generation of induced pluripotent stem cells using recombinant proteins," *Cell Stem Cell* 4(5):381-384.
Zhou, X. et al. (Sep. 15, 2012, e-published Aug. 8, 2012). "Cutting edge: generation of memory precursors and functional memory CD8+ T cells depends on T cell factor-1 and lymphoid enhancer-binding factor-1," *J Immunol.* 189(6): 2722-2726.
Baker et al., "Prostaglandin inhibition of T-cell proliferation is mediated at two levels," *Cell Immunol.*, 61(1):52-61 (1981).
Barbey et al., "Ex vivo monitoring of antigen-specific CD4+ T cells after recall immunization with tetanus toxoid," *Clin Vaccine Immunol.*, 14(9):1108-1116 (2007).
Chan et al., "Conformational Control Inhibition of the BCR-ABL 1 Tyrosine Kinase, Including the Gatekeeper T315I Mutant, by the Switch-Control Inhibitor DCC-2036," *Cancer Cell*, 19:556-568 (2011).
Garcillán et al., "γδ T lymphocytes in the diagnosis of human t cell receptor immunodeficiencies," *Front Immunol.* 6:20 (2015).
Kalinski, "Regulation of immune responses by prostaglandin E2," *J. Immunol.*, 188(1):21-28 (2012).
Parameswaran et al., "Novel Approach for NK Cell Therapy for Cancer," *Blood*, 124(21):3836 (2014).
Sakata et al., "Prostaglandin E2, an immunoactivator," *J. Pharmacol. Sci.*, 112(1):1-5 (2010).
Seggewiss et al., "Imatinib inhibits T-cell receptor-mediated T-cell proliferation and activation in a dose-dependent manner," *Blood*, 105:2473-2479 (2005).
Tighe et al., "GSK-3 inhibitors induce chromosome instability," *BMC Cell Biology*, 8(34):1-17 (2007).
Weichsel et al., "Profound Inhibition of Antigen-Specific T-Cell Effector Functions by Dasatinib.," *Clin. Cancer Res.*, 14(8):2484-2491 (2008).

(56) References Cited

OTHER PUBLICATIONS

Yoshioka et al., "Differential effects of inhibition of bone morphogenic protein (BMP) signalling on T-cell activation and differentiation," *Eur. J. Immunol.*, 42:749-759 (2012).

Blazar et al., U.S. Appl. No. 62/264,455, filed Dec. 8, 2015.

Campbell et al., "CCR7 expression and memory T cell diversity in humans," *J. Immunol.*, 166(2):877-884 (2001).

Fujisaki, H. et al. (May 1, 2009, e-published Apr. 21, 2009). "Expansion of highly cytotoxic human natural killer cells for cancer cell therapy," *Cancer Res* 69(9):4010-4017.

Mestermann et al., "The tyrosine kinase inhibitor dasatinib acts as a pharmacologic on/off switch for CART cells," *Sci. Transl. Med.*, 11:eaau5907, pp. 1-11 (2019).

Mustjoki et al., "Rapid mobilization of cytotoxic lymphocytes induced by dasatinib therapy," *Leukemia*. 27(4): 914-24 (2013).

Soriani et al., "Chemotherapy-elicited upregulation of NKG2D and DNAM-1 ligands as a therapeutic target in multiple myeloma," *Oncoimmunology*, 2(12):e26663 (2013).

Wu et al., "Dasatinib promotes the potential of proliferation and antitumor responses of human γδT cells in a long-term induction ex vivo environment," *Leukemia*, 28:206-210 (2014).

\* cited by examiner

COMPOSITIONS AND METHODS FOR IMMUNE CELL MODULATION IN ADOPTIVE IMMUNOTHERAPIES

RELATED APPLICATION

This application claims priority to U.S. Provisional Application Ser. No. 62/281,064, filed Jan. 20, 2016 and U.S. Provisional Patent Application No. 62/402,883, filed Sep. 30, 2016, the disclosures of which are hereby incorporated by reference in their entirety.

FIELD OF THE INVENTION

The present disclosure is broadly concerned with the field of adoptive immune cell therapies. More particularly, the present disclosure is concerned with the use of small molecules for modulating immune-cells suitable for adoptive cell therapies.

BACKGROUND OF THE INVENTION

Adoptive immunotherapy involves administration of immune cells to patients having cancer, tumor, or infections, whereby the administered immune cells provide a therapeutic benefit to the patients. Generally speaking, immune cells suitable for immunotherapy include, but are not limited to, B cells, dendritic cells (DC), T cells, Natural Killer (NK) cells, NKT (Natural Killer T) cells, and hematopoietic stem or progenitor cells. Mediating complete and durable disease responses in patients is the central goal of these cell-based immunotherapies.

Advances in our understanding of the biological mechanisms behind the effectiveness of adoptive T cell therapies, including, but not limited to, CAR-T cells, TCR-T cells, virus-specific T cells (VSTs) and tumor-infiltrating T cell (TILs), have underscored the importance of the certain attributes associated with transferred T cells and revealed the complexity of the inhibitory barriers posed by the host and tumor cells that need to be overcome for the success of the treatment of cancer. Among T cell factors, the avidity of the T cell receptor (TCR) or chimeric antigen receptor (CAR), the proliferative and survival capacities, migration to the tumor site(s), and the ability to sustain effector functions within the tumor have, in correlative studies, been shown to be crucial determinants for triggering the eradication of malignant cells. However, adding to another layer of complexity, even though some of these desirable attributes were recognized, the pathways or players driving these attributes are still unclear, which limits one's ability to intervene and obtain cells having desired quantity and quality for their therapeutic uses.

Using CAR-T cell therapy as an example, the therapy has to overcome multiple challenges including CAR-T potency and persistence, migration to the tumor, the immunosuppressive tumor microenvironment, tumor heterogeneity and patient safety. Multiple approaches are being applied to overcome these challenges. For example, specific T-cell subsets are selected for therapeutic use and further engineering of the CAR may be used to improve tumor targeting, CAR potency and on-target/off-tumor safety issues. However, improving the CAR-T therapeutic efficacy, including CAR-T persistence and migration remains to be resolved. It has been shown that the in vivo efficacy of the T cell therapy can be strongly influenced by the manufacturing process which is dependent upon both the starting population of T cells going into the process or feedstock, and the ex vivo expansion and activation methods utilized. It has been demonstrated that the differentiation state of the administered T cells can significantly affect in vivo persistence and anti-tumor activity. T helper (CD4+ T cells) and cytotoxic T cells (CD8+), specifically, naïve (Tn), stem cell memory (Tscm) and central memory (Tcm) T cells, characterized by the expression of the CCR7 and CD62L markers, mediate superior anti-tumor activity in both mouse models (Sommermeyer et al. 2015) and in nonhuman primate models (Berger et al. 2008).

During the manufacturing process, therapeutic cells (or cell populations) are typically activated and expanded. This process generally drives differentiation of the cells and leads to an increase in the proportion of the cells in a more differentiated state—in the case of T-cells, the more differentiated cells are phenotypically characterized as effector memory or effector T cells. Once infused into patients, these more differentiated cells have a lower capacity to proliferate and a lower potential to persist as a long-lived or persistent population, as compared to cells in less differentiated states. Thus, there is an urgent need in the art not only for compositions and methods useful for maintaining and expanding desired immune cell subsets, but also for reducing cell differentiation during expansion, and for dedifferentiating cells to less differentiated cells, thereby obtaining desired immune cell subsets that have greater capacity to proliferate and persist in order to improve the efficacy of various adoptive immunotherapies.

Similar efficacy issues exist in NK-cell based therapies as well. Natural killer cells have traditionally been categorized as innate immune cells that are characterized as being relatively short-lived and exhibit minimal change in response to secondary exposure to a stimulus i.e., display limited target memory responses. However, recent research has uncovered information on both activating and inhibitory NK cell receptors which play important roles including self-tolerance and sustaining NK cell activity. Data have demonstrated the ability of NK cells to readily adjust to the immediate environment and formulate antigen-specific immunological memory, which is fundamental for responding to secondary exposure to the same antigen. A subpopulation of NK cells, now called adaptive NK cells or memory NK cells, have been identified by several groups. These cells have many functional characteristics similar to CD8+ T cells, including being longer-lived and having enhanced response to stimuli after an initial exposure. These properties may result in a more efficacious cell therapy strategy, as compared to canonical NK cells. Expanding and maintaining adaptive/memory NK cells that mediate durable antigen-specific recognition in vivo would be a key to improving NK-cell based adoptive immunotherapy.

Further, it is believed that, like T and NK cells, improvements can be made to isolate more efficacious NKT cells, a type of CD1d-restricted T cell playing a role in both the innate and adaptive immune systems, which can be targeted for modulation to yield an improved cell therapy.

Since the final state of the cells, or specifically, the cell subtypes, going into the patient can be defined in large part by the manufacturing process, the importance of that process cannot be overstated. Preferentially maintaining or expanding cell subpopulations having a desired differentiation state, and/or adaptive immune cell characteristics during cell culture and expansion could be extremely beneficial for enhancing the efficacy of cell-based therapies. Thus, a manufacturing approach that can enhance the desired T, NK or NKT cell subsets both in quantity and quality could provide a significant enhancement of their therapeutic efficacy.

There is a substantial need in the art for immune cell subsets with improved therapeutic efficacy. However, while certain desirable attributes of therapeutic immune cells are known, the pathways and/or players involved in achieving these attributes are largely unknown. The methods and compositions of the present invention addresses this need and provide other related advantages in the field of immune cell therapy.

SUMMARY OF THE INVENTION

The present invention provides compositions and methods for modulating one or more populations or subpopulations of immune cells to improve their therapeutic potential for adoptive immunotherapies. It is an object of the present invention to provide one or more compounds, either alone or in combination to improve proliferation, persistence, cytotoxicity, and/or cell recall/memory of therapeutic immune cells by, for example, increasing the number or ratio of a subpopulation of cells that displays improvement in at least one of the following qualities that are expected to result in better immunotherapeutic results: migration, homing, cytotoxicity, maintenance, expansion, persistence, longevity, desired states of differentiation.

One aspect of the invention provides a composition for improving therapeutic potential of immune cells suitable for adoptive cell-based therapies, and the composition comprises one or more agents selected from the group consisting of compounds listed in Table 1: Dorsomorphin; Heptelidic acid; 1-Pyrrolidinecarbodithioic acid, ammonium salt; 2-dexoyglucose (2-DG); GSK3 Inhibitor; Rho kinase inhibitors; MEK inhibitors; PDK1 agonist; TGFβ inhibitors; 6-Mercaptopurine; AC-93253 iodide; Tiratricol; PI-103; Fulvestrant; Thapsigargin; SU 4312; Telmisartan; Cyclosporin A; 1,3,5-tris(4-hydroxyphenyl)-4-propyl-1H-pyrazole; BAY 61-3606; Protoporphyrin IX disodium; mTOR inhibitor; HS173; LY294002; Pictilisib; 5-Azacytidine; Fludarabine; Roscovitine, (S)-Isomer; PAC-1; 8-Quinolinol, 5,7-dichloro-; Nitrofurantoin; 8-Quinolinol, 5-chloro-7-iodo-; 2-Naphthacenecarboxamide, 7-chloro-4-(dimethylamino)-1,4,4a,5,5a,6,11,12a-octahy; Nifuroxazide; Tosufloxacin hydrochloride; Sertraline; Diethylenetriaminepentaacetic acid, penta sodium; Edrophonium chloride; BIX01294; Terfenadine; and dmPGE2. The one or more agents selected from the group consisting of compounds listed in Table 1 improve therapeutic potential of immune cells or one or more subpopulation thereof via modulating of the immune cells using one or more agent. In some embodiments, the modulation of the immune cells is ex vivo.

In some embodiments, the one or more of compounds listed in Table 1 modulates cell expansion, maintenance and/or differentiation, and thereby improve proliferation, cytotoxicity, cytokine response and secretion, cell recall, and/or persistence of the immune cells, or one or more subpopulation thereof.

In one embodiment, the one or more of the compounds listed in Table 1 improves cell survival rate of the immune cell, or one or more subpopulation thereof both ex vivo and in vivo.

In one embodiment, the one or more of the compounds listed in Table 1 increases the ratio of one or more desired cell subpopulation of the immune cells.

In some embodiments, the present invention provides one or more selected agents herein to improve therapeutic efficacy of a population or subpopulation of immune cells, including but not limited to T, NK and NKT cells. In some embodiments, the immune cells immune cells suitable for adoptive cell-based therapies comprise T cells, NKT cells, or NK cells. In some embodiments, the immune cells subject to the treatments comprise T cells, as such the one or more desired cell subpopulations has an increased ratio comprises naïve T cells, stem cell memory T cells, and/or central memory T cells. In some embodiments, the immune cells subject to the treatments using the agents comprise NKT cells, as such the one or more desired cell subpopulations has an increased ratio comprise type I NKT cells. In some other embodiments, the immune cells subject to the treatments using the agents comprise NK cells, and wherein the one or more desired cell subpopulations has an increased ratio comprise adaptive NK cells.

In some embodiments, the composition comprising one or more agents selected from the group consisting of the compounds, or derivatives, analogues or pharmaceutically acceptable salts thereof, listed in Table 1. The compounds, or derivatives, analogues or pharmaceutically acceptable salts thereof further comprise ester, ether, solvate, hydrate, stereoisomer, and prodrug of the compounds of Table 1.

In some embodiments, the composition for improving therapeutic potential of immune cells comprises at least one agent selected from Group I, and one or more agents selected from Group II, Group III, Group IV, and/or Group V.

Group I comprises: dorsomorphin, heptelidic acid, 1-Pyrrolidinecarbodithioic acid, and 2-DG. Without being limited to the theory, Group I agents, among other potential roles, impact cell metabolism and nutrient sensing.

Group II comprises: GSK3 Inhibitor, ROCK inhibitor, TGFβ receptor inhibitor, MEK inhibitor, PDK1 agonist, 6-Mercaptopurine, AC-93253 iodide, tiratricol, PI-103, fulvestrant, thapsigargin, SU 4312, U0126, telmisartan, cyclosporin A, 1,3,5-tris(4-hydroxyphenyl)-4-propyl-1H-pyrazole, BAY 61-3606, protoporphyrin IX disodium, mTOR inhibitor, TWS119, HS173, LY294002, and Pictilisib. Without being limited to the theory, Group II agents, among other potential roles, impact signal transduction in various functional pathways.

Group III comprises: 5-Azacytidine, fludarabine, roscovitine, and PAC-1. Without being limited to the theory, Group III agents, among other potential roles, impact cell proliferation and apoptosis.

Group IV comprises: 5,7-dichloro-8-Quinolinol, 2-Naphthacenecarboxamide, 7-chloro-4-(dimethylamino)-1,4,4a,5, 5a,6,11,12a-octahy, Nifuroxazide, and Tosufloxacin hydrochloride. Without being limited to the theory, Group IV agents, among other potential roles, may impact cell properties relating to infective processes.

Group V comprises: sertraline, diethylenetriaminepentaacetic acid, edrophonium chloride, BIX01294, terfenadine, and dmPGE2. Without being limited to the theory, Group V agents, among other potential roles, generally impact other cell properties relating to expansion, maintenance, differentiation, proliferation, survival rate, cytotoxicity, cell recall, and/or persistence.

In some other embodiments, the composition for improving therapeutic potential of immune cells comprises at least one agent selected from Group II, and one or more agents selected from Group I, Group III, Group IV, and/or Group V.

In still other embodiments, the composition for improving therapeutic potential of immune cells comprises at least one agent selected from Group III, and one or more agents selected from Group I, Group II, Group IV, and/or Group V.

In yet other embodiments, the composition for improving therapeutic potential of immune cells comprises at least one agent selected from Group IV, and one or more agents selected from Group I, Group II, Group III, and/or Group V.

In still some other embodiments, the composition for improving therapeutic potential of immune cells comprises at least one agent selected from Group V, and one or more agents selected from Group I, Group II, Group III, and/or Group IV.

In some embodiments, the composition for improving therapeutic potential of immune cells comprises a combination comprising at least one agent selected from the group consisting of TWS119, HS173, LY294002, Pictilisib, and 2-DG; and one or more additional agent selected from the group consisting of compounds listed in Table 1. In some particular embodiments, the composition comprises a synergistic combination of two or more agents selected from the group consisting of TWS119, HS173, LY294002, Pictilisib, and 2-DG.

In some embodiments, the composition comprising one or more agents selected from the group consisting the compounds listed in Table 1 further comprises at least one organic solvent selected from the group consisting of dimethyl sulfoxide (DMSO), N,N-dimethylformamide (DMF), dimethoxyethane (DME), dimethylacetamide, ethanol and combinations thereof.

In some embodiments, the composition comprises at least one agent selected from Group II. In some embodiments, the composition comprises an mTOR inhibitor. In some embodiments, the composition comprises at least one agent selected from Group II, and one or more agents selected from Group V. In one embodiment, the composition comprises an mTOR inhibitor, and dmPGE2, or an analogue or a derivative of dmPGE2. In some embodiments, the mTOR inhibitor is selected from rapamycin, and analogues or derivatives thereof, which comprise sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, or other O-alkylated and O-methylated rapamycin derivatives. In one embodiment, dmPGE2 is 16,16-dimethyl Prostaglandin E2. In some other embodiments, the analogue or derivative of dmPGE2 is selected from the group consisting of $PGE_2$, 16,16-dimethyl $PGE_2$ p-(p-acetamidobenzamido) phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso PGE2 isopropyl ester, 8-iso-16-cyclohexyl-tetranor $PGE_2$, 20-hydroxy $PGE_2$, 20-ethyl $PGE_2$, 11-deoxy PGEi, nocloprost, sulprostone, butaprost, 15-keto $PGE_2$, and 19 (R) hydroxy $PGE_2$. In one particular embodiment, the composition comprises rapamycin and dmPGE2.

Another aspect of the invention provides a composition comprising a population or subpopulation of immune cells, and one or more agents selected from the group consisting of the compounds listed in Table 1, and derivatives and analogues thereof. In some embodiments, the immune cells are contacted with the one or more agents to improve therapeutic potential of the immune cells for adoptive cell therapy in comparison to immune cells without such contact. In some embodiments, the immune cells are contacted with the one or more agents to improve cell expansion, maintenance, differentiation, dedifferentiation, and/or survival rate in comparison to immune cells without the same treatment. In yet some other embodiments, the immune cells are contacted with the one or more agents to improve cell proliferation, cytotoxicity, persistence, and/or recall in comparison to immune cells without the same treatment.

In some embodiments, the immune cells contacted with the one or more agents have an increased number or ratio of a desired subpopulation of the immune cells in comparison to immune cells without the same treatment. In some embodiments, the immune cells comprise T, NK or NKT cells. In one embodiment, the composition comprises a population of T cells, as such the desired subpopulation of immune cells after contacting the agent(s) comprise naïve T cells, stem cell memory T cells, and/or central memory T cells. In some embodiments, the composition comprises a population of NKT cells, as such the desired subpopulation of immune cells after contacting the agents comprise type I NKT cells. In yet some other embodiments, the immune cells comprise a population of NK cells, as such the desired subpopulation of immune cells after contacting the agents comprise adaptive NK cells. In other embodiments the adaptive NK cells comprise CD57+ and at least one of NKG2C+, low PLZF, low SYK, low FεFRγ, low EAT-2, low TIGIT, low PD1, low CD7, low CD161, high LTLRB1, high CD45RO, and low CD45RA In some embodiments, the population or subpopulation of immune cells of the composition are isolated from or comprised in peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered with genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In yet another embodiment, the immune cells are differentiated in vitro from stem cells, hematopoietic stem or progenitor cells, or progenitor cells; or are trans-differentiated in vitro from non-pluripotent cells of hematopoietic or non-hematopoietic lineage. In some embodiments, the immune cells of the composition are genomically engineered and comprise an insertion, a deletion, or a nucleic acid replacement (substitution, or indel). In some particular embodiments, the immune cells of the composition comprise an exogenous nucleic acid encoding a T Cell Receptor (TCR) and/or a Chimeric Antigen Receptor (CAR). In some embodiments, the immune cells isolated from tissue of a subject are genetically engineered, and may comprise a TCR or a CAR. In some embodiments, the immune cells isolated from tissue or a subject is a CAR-T cell.

In still some other embodiments, the immune cells of the composition are differentiated in vitro from stem cells, hematopoietic stem or progenitor cells, or progenitor cells. In one embodiment, the stem cell is induced pluripotent stem cells (iPSCs) or embryonic stem cells (ESCs). In one embodiment, the progenitor cell is a CD34+ hemogenic endothelium cell, a multipotent progenitor cell, a T cell progenitor cell, a NK progenitor cell, or a NKT progenitor cell. In some embodiments, the stem cell, hematopoietic stem or progenitor cell, or progenitor cell is genomically engineered and comprises an insertion, a deletion, or a nucleic acid replacement, or comprises at least one genetically modified modality. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16. In some other embodiments, the immune cells of the composition are trans-differentiated in vitro from non-pluripotent cells of hematopoietic or non-hematopoietic lineage. In some embodiments, the desired subpopulation of immune cells after modulation comprises immune cells having at least one genetically modified modality. In some embodiments, the genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; and (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

In some embodiments, the composition comprising the immune cells and one or more agents selected from the group consisting of compounds listed in Table 1, further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest; an antibody, or an antibody fragment; and a chemotherapeutic agent, a radioactive moiety, or an immunomodulatory drug (IMiD). In some of these embodiments, the antibody, or antibody fragment, specifically binds to a viral antigen. In other embodiments, the antibody, or antibody fragment, specifically binds to a tumor antigen. In some embodiments, the additional additive comprises. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In one specific embodiment, the composition comprises a mixture of a population or subpopulation of immune cells and one or more of a GSK3 inhibitor, a TGFβ receptor inhibitor, a ROCK inhibitor, a MEK inhibitor, a PDK1 agonist, and an mTOR inhibitor, wherein the immune cells comprise T cells, NK cells or NKT cells. In one embodiment, the composition comprises an mTOR inhibitor, wherein the immune cells comprise T cells. In one embodiment, the T cells comprise CAR-T cells. In some embodiments, the mTOR inhibitor is selected from rapamycin, and analogues or derivatives thereof.

In some embodiments, the composition comprising the immune cells and one or more agents listed in Table 1 comprises at least one agent selected from Group II, and one or more agents selected from Group V. In one embodiment, the composition comprises an mTOR inhibitor and dmPGE2, or an analogue or derivative of dmPGE2. In some embodiments, the mTOR inhibitor is selected from rapamycin, and analogues or derivatives thereof, which comprise sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives. In one embodiment, dmPGE2 is 16,16-dimethyl Prostaglandin E2. In some other embodiments, the analogue or derivative of dmPGE2 is selected from the group consisting of $PGE_2$, 16,16-dimethyl $PGE_2$ p-(p-acetamidobenzamido) phenyl ester, 1 1-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso PGE2 isopropyl ester, 8-iso-16-cyclohexyl-tetranor $PGE_2$, 20-hydroxy $PGE_2$, 20-ethyl $PGE_2$, 11-deoxy PGEi, nocloprost, sulprostone, butaprost, 15-keto $PGE_2$, and 19 (R) hydroxy $PGE_2$. In one particular embodiment, the composition comprises CAR-T cells, rapamycin and dmPGE2.

Still, another aspect of the invention provides a composition comprising an isolated population of immune cells that has been contacted or modulated with a composition comprising one or more agents listed in Table 1, or a derivative or an analogue thereof. In some embodiments, the composition provided is a therapeutic composition having the treated isolated population or subpopulation of immune cells including, but not limited to, T, NK, and NKT cells. The therapeutic composition can be washed with a buffer substantially free of the modulating agent.

In some embodiments, the modulated cell population comprises immune cells having improved therapeutic potential for adoptive cell therapy in comparison to unmodulated cell population. In some embodiments, the isolated population of immune cells has improved cell expansion, maintenance, differentiation, dedifferentiation, and/or survival rate in comparison to immune cells without the treatment by the one or more agents. In some embodiments, the isolated population of immune cells has improved cell proliferation, cytotoxicity, cytokine response and secretion, cell recall, and persistence in comparison to immune cells without the treatment by the one or more agents. In some other embodiments, the isolated population of immune cells has increased number or ratio of one or more desired subpopulations of the immune cells in comparison to immune cells without the same treatment.

In some embodiments, the isolated population of immune cells that treated with one or more agents selected from the group consisting of compounds listed in Table 1 comprises T cells, as such the obtained one or more desired subpopulation of immune cells comprise naïve T cells, stem cell memory T cells, and/or central memory T cells. In some embodiments, the isolated population of immune cells treated with one or more agents comprises NKT cells, as such the obtained one or more desired subpopulation of immune cells comprise type I NKT cells. In yet some other embodiments, the isolated population of immune cells treated with one or more agents comprises NK cells, as such the one or more desired subpopulation of immune cells comprise adaptive NK cells.

In some embodiments of the composition as provided, the isolated population of immune cells may be isolated from peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered with genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In some embodiments of the composition as provided, the isolated population of immune cells may be differentiated from a stem cell, a hematopoietic stem or progenitor cell, or a progenitor cell. In some embodiments, the isolated population of immune cells may be differentiated from a stem cell, a hematopoietic stem or progenitor cell, or a progenitor cell prior to, or during, the treatment by the agent(s). In some embodiments, the stem cell is an induced pluripotent stem cell (iPSC) or embryonic stem cell (ESC). In some embodiments, the progenitor cell is a CD34+ hemogenic endothelium cell, a multipotent progenitor cell, a T cell progenitor cell, a NK progenitor cell, or a NKT progenitor cell. In some further embodiment, the stem cell, hematopoietic stem or progenitor cell, progenitor, the derived immune cell for modulation, or modulated derived immune cell is genomically engineered, for example, comprising an insertion, a deletion, and/or a nucleic acid replacement. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16.

In some other embodiment of the composition as provided, the isolated population of immune cells may be trans-differentiated from a non-pluripotent cell of hematopoietic or non-hematopoietic lineage. In some embodiments, the isolated population of immune cells may be trans-differentiated from a non-pluripotent cell of hematopoietic or non-hematopoietic lineage prior to, or during, the treatment by the agent.

In some embodiments of the composition as provided, the isolated population of immune cells comprise T cells that have been modulated with a composition comprising an mTOR inhibitor. In some embodiments of the composition as provided, the isolated population of immune cells comprise T cells that have been modulated with a composition comprising an mTOR inhibitor, and dmPGE2 or an analogue or derivative of dmPGE2. In some embodiments, the mTOR inhibitor is selected from rapamycin, and analogues and derivatives thereof comprising sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives. In some embodiments, the analogue or derivative of dmPGE2 is selected from the group consisting of $PGE_2$, 16,16-dimethyl $PGE_2$ p-(p-acetamidobenzamido) phenyl ester, 1 1-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso PGE2 isopropyl ester, 8-iso-16-cyclohexyl-tetranor $PGE_2$, 20-hydroxy $PGE_2$, 20-ethyl $PGE_2$, 11-deoxy PGEi, nocloprost, sulprostone, butaprost, 15-keto $PGE_2$, and 19 (R) hydroxy $PGE_2$. In yet some other embodiments, the composition comprises rapamycin and $dmPGE_2$.

In some embodiments of the composition as provided, the isolated population of immune cells comprise T cells. In some embodiments, the isolated population of immune cells comprise CAR-T cells. In some embodiments, the modulated immune cells comprising T cells having at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased spare respiratory capacity (SRC); (4) increased central memory T cell subpopulation; (5) decreased effector T cell subpopulation; (6) improved expansion and viability; and (7) improved capability in tumor clearance and persistence, when compared to T cells without being modulated with a composition comprising an mTOR inhibitor, and optionally dmPGE2 or an analogue or derivative of dmPGE2. In some embodiments, the T cells having at least one of the above properties are CAR-T cells.

Another aspects of the present invention provides a composition comprising an isolated population of T cells having at least one of the properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased spare respiratory capacity (SRC); (4) increased central memory T cell subpopulation; and (5) decreased effector T cell subpopulation, when in comparison to T cells without being modulated. In some embodiments, the isolated population of T cells in the composition comprise CAR-T cells. In some embodiments, the isolated population of T cells in the composition have improved capability in at least one of: expansion; viability; persistence and tumor clearance.

Another aspect of the present invention provides a method of modulating a population of immune cells for adoptive therapies, the method generally comprises contacting the population of immune cells with a sufficient amount of a composition comprising at least one agent selected from the group consisting of the compounds listed in Table 1, and derivatives and analogues thereof, for a time sufficient to obtain a population of modulated immune cells having improved therapeutic potential for adoptive cell therapy compared to unmodulated immune cells. In some embodiments, the modulated immune cells for adoptive therapies are autologous. In some embodiments, the modulated immune cells for adoptive therapies are allogenic.

In some embodiments of the method, contacting the population of immune cells with the one or more agents improves proliferation, cytotoxicity, cytokine response, cytokine release, cell recall, and/or persistence; and/or improves cell expansion, maintenance, differentiation, de-differentiation, and/or survival rate in comparison to immune cells without the treatment by the one or more agents of Table 1, and derivative or analogs thereof. In some embodiments of the method, contacting the population of immune cells with one or more agents of Table 1, and derivative or analogs thereof, increases the number or ratio of one or more desired subpopulations of the immune cells in comparison to immune cells without the treatment by the same one or more agents.

In some embodiments, the above method further comprises (b) isolating the one or more desired subpopulations of the immune cells contacted with the one or more agents of Table 1.

In some embodiments, the above method further comprises administering the population or a subpopulation of the treated immune cells of step (a), or the isolated one or more desired subpopulations of the immune cells of step (b), or the therapeutical composition thereof to a subject in need of cell therapy. In some embodiments, the subject has an autoimmune disorder, hematological malignancy, solid tumor, or infection. In some embodiments, the subject had, is under, or will be treated with, chemotherapy or radiation therapy.

In some embodiments, the population of immune cells comprises T cells, NKT cells, or NK cells. In one embodiment of the method, the population of immune cells comprises T cells, and the one or more desired subpopulations after treatment comprise naïve T cells, stem cell memory T cells, and/or central memory T cells. In one embodiment of the method, the population of immune cells comprises NKT cells, and the one or more desired subpopulations after treatment comprise type I NKT cells. In one embodiment of the method, the population of immune cells comprises NK cells, and the one or more desired subpopulations after treatment comprise adaptive NK cells.

In some embodiments of said general method, the immune cells for modulation are isolated from or comprised in peripheral blood, bone marrow, lymph node tissue, cord blood, thymus tissue, tissue from a site of infection, ascites, pleural effusion, spleen tissue, or tumors. In some embodiments, the immune cells for modulation are isolated from a healthy subject; a subject having an autoimmune disease, a hematopoietic malignancy, a virus infection or a solid tumor; a subject previously administered with genetically modified immune cells; or a subject that is CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genomically modified immune cells are isolated for ex vivo modulation using the present compositions and methods as disclosed. In some embodiments, after modulation, the genomically modified immune cells isolated from a subject may be administered to the same donor or a different patient.

In some embodiments, the immune cells for modulation are differentiated in vitro from stem cells, hematopoietic stem or progenitor cells, or progenitor cells. In some embodiments, the immune cells for modulation are trans-differentiated in vitro from non-pluripotent cells of hematopoietic or non-hematopoietic lineage. In some embodiments, said stem cells comprise induced pluripotent stem cells (iPSCs) or embryonic stem cells (ESCs). In some embodiments, said progenitor cell is a CD34+ hemogenic endothelium cell, a multipotent progenitor cell, a T cell progenitor cell, a NK progenitor cell, or a NKT progenitor cell. In yet some other embodiments, the stem cell, hematopoietic stem or progenitor cell, or progenitor cell is genomically engineered and comprises an insertion, a deletion, or a nucleic acid replacement, and/or comprises at least one genetically modified modality. As such, the desired subpopulation of modulated immune cells derived therefrom comprises immune cells having at least one genetically modified modality.

In some embodiments, said genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of deletion or reduced expression of B2M, TAP1, TAP2, Tapasin, NLRC5, PD1, LAG3, TIM3, RFXANK, CIITA, RFX5, or RFXAP, and any gene in the chromosome 6p21 region. In some other embodiments, the genetically modified modalities comprise one or more introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

In some embodiments of the method of modulating immune cells, said "time sufficient" or "sufficient length of time" is no less than 16 hours, 14 hours, 12 hours, 10 hours, 8 hours, 6 hours, 4 hours, 2 hours, 1 hour, 0.5 hour, 0.1 hour, or any length of time in between. As such, said sufficient length of time, for example, is no less than 15, 13, 11, 9, 7, 5, 3, 1, 0.5, or 0.1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

In some embodiments of said method, the immune cells, during and/or after modulation, are in a feeder-free environment. Feeder-free conditions include feeder cell free, and feeder-conditioned medium free. In some embodiments of said method, the immune cells, during modulation, are co-cultured with feeder cells.

In some embodiments, the subject can be a candidate for adoptive cell transfer. In some embodiments, the subject can be a candidate for bone marrow or stem cell transplantation. In some embodiments, the subject has previously received a bone marrow or stem cell transplantation. In some embodiments, the subject has received bone marrow ablative or non-myeolablative chemotherapy or radiation therapy.

In some embodiments of method, the composition for contacting the immune cells comprise an mTOR inhibitor. In some embodiments of method, the composition for contacting the immune cells comprise an mTOR inhibitor, and dmPGE2 or an analogue or derivative of dmPGE2. In some embodiments, the mTOR inhibitor is selected from rapamycin, and analogues and derivatives thereof comprising sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives. In some embodiments, the analogue or derivative of dmPGE2 is selected from the group consisting of $PGE_2$, 16,16-dimethyl $PGE_2$ p-(p-acetamidobenzamido) phenyl ester, 1 l-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso PGE2 isopropyl ester, 8-iso-16-cyclohexyl-tetranor $PGE_2$, 20-hydroxy $PGE_2$, 20-ethyl $PGE_2$, 11-deoxy PGEi, nocloprost, sulprostone, butaprost, 15-keto $PGE_2$, and 19 (R) hydroxy $PGE_2$. In yet some other embodiments, the composition for contacting the immune cells comprises rapamycin and $dmPGE_2$.

In some embodiments of the method as provided, the population of immune cells comprise T cells. In some embodiments, the population of immune cells comprise CAR-T cells. In some embodiments, the modulated cell population comprising T cells having at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased spare respiratory capacity (SRC); (4) increased central memory T cell subpopulation; (5) decreased effector T cell subpopulation; (6) improved expansion and viability; and (7) improved capability in tumor clearance and persistence, when compared to T cells without being modulated with a composition comprising an mTOR inhibitor, and dmPGE2 or an analogue or derivative of dmPGE2. In some embodiments, the T cells having at least one of the above properties are CAR-T cells.

An additional aspect of the invention provides a method of making a therapeutic composition for cell therapies according to any of the above methods for modulating a population of immune cells.

A further aspect of the present invention provides using the above immune cell modulation methods to make therapeutic compositions comprising modulated immune cells for cell therapies. In some embodiment, the modulated immune cells comprise T, NK and/or NKT cells. In some embodiments, the modulated NK cells comprise adaptive NK cells. An additional aspect of the present invention provides a population of modulated immune cells comprising selectively expanded NK cells made by the method provided herein.

Yet another aspect of the present invention provides a therapeutic composition comprising the modulated cells obtained using the methods and composition disclosed herein, and a therapeutically acceptable medium. In some embodiments of the therapeutic composition, the composition further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, antibodies, chemotherapeutic agents or radioactive moiety, and immunomodulatory drugs (IMiDs).

Further provided is a method of treating a subject by administering a therapeutically sufficient amount of the above said therapeutic composition to a subject in need of an adoptive cell therapy. In some embodiments, the cell therapy is autologous. In some other embodiments, the cell therapy is allogeneic. In some embodiments, the subject in need of the therapy has an autoimmune disorder, a hematological malignancy, a solid tumor, cancer, or an infection associated with HIV, RSV, EBV, CMV, adenovirus, or BK polyomavirus. In some embodiments, the method of treating a subject using the modulated immune cells is carried out by administering said therapeutic composition in combination with an antibody, a chemotherapeutic, or a radioactive treatment, wherein the antibody, chemotherapeutic, or radioactive treatment is prior to, during or after administering the therapeutic composition.

Yet another aspect of the invention provides use of a mixture for manufacturing of a therapeutic composition for cell therapies, wherein the mixture comprises: (a) an isolated population of immune cells, and (b) a composition comprising an mTOR inhibitor, or a combination of an mTOR inhibitor, and dmPGE2 or an analogue or derivative of dmPGE2. In some embodiments, the mTOR inhibitor is selected from rapamycin, and analogues and derivatives thereof. In some embodiments, the analogues and derivatives of rapamycin is selected from the group consisting of sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, or other O-alkylated or O-methylated rapamycin derivatives. In some other embodiments, the analogue or derivative of dmPGE2 is selected from the group consisting of $PGE_2$, 16,16-dimethyl $PGE_2$ p-(p-acetamidobenzamido) phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso PGE2 isopropyl ester, 8-iso-16-cyclohexyl-tetranor $PGE_2$, 20-hydroxy $PGE_2$, 20-ethyl $PGE_2$, 11-deoxy PGEi, nocloprost, sulprostone, butaprost, 15-keto $PGE_2$, and 19 (R) hydroxy $PGE_2$. In one particular embodiment, the mixture for manufacturing a therapeutic composition for cell therapies comprises a combination of rapamycin and dmPGE2.

As provided, in the mixture for manufacturing of a therapeutic composition for cell therapies, the composition comprising a combination of an mTOR inhibitor, and dmPGE2 or an analogue or derivative of dmPGE2 is capable of modulating the isolated population of immune cells. In some embodiments the mixture for manufacturing a therapeutic composition for cell therapies comprises an isolated population of T cells. In some embodiments, the T cells are CAR-T cells.

In some embodiments, after being modulated by the combination of an mTOR inhibitor, and dmPGE2 or an analogue or derivative of dmPGE2, the modulated immune cells comprises T cells having at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased spare respiratory capacity (SRC); (4) increased central memory T cell subpopulation; (5) decreased effector T cell subpopulation; (6) improved expansion and viability; and (7) improved capability in tumor clearance and persistence, when compared to T cells without being modulated.

Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIG. 7A: the comparison of genome-wide transcriptional profiles induced by rapamycin, dmPGE2, and rapamycin+dmPGE2 combination by probes included in the microarray. FIG. 7B: Venn diagram representing the number of genes having differential changes (up or down regulated 2 fold or more in comparison to the vehicle treatment) under rapamycin, dmPGE2, and/or rapamycin+dmPGE2 combination treatments.

FIG. 13A: CAR-T cells treated with rapa+dmPGE2 or the PI3K inhibitor PI-103 were able to clear tumor from the majority of mice, while those treated with untransduced T cells, or CAR-T cells treated with DMSO, U0126 or TWS119, demonstrated minimal tumor control. FIG. 13B: At 21 days post challenge with secondary tumor 75% of the rapa+dmPGE2-treated CAR-T mice and 60% of the PI103 CAR-T-treated mice had no detectable tumor.

DETAILED DESCRIPTION OF THE INVENTION

Figure 1A:
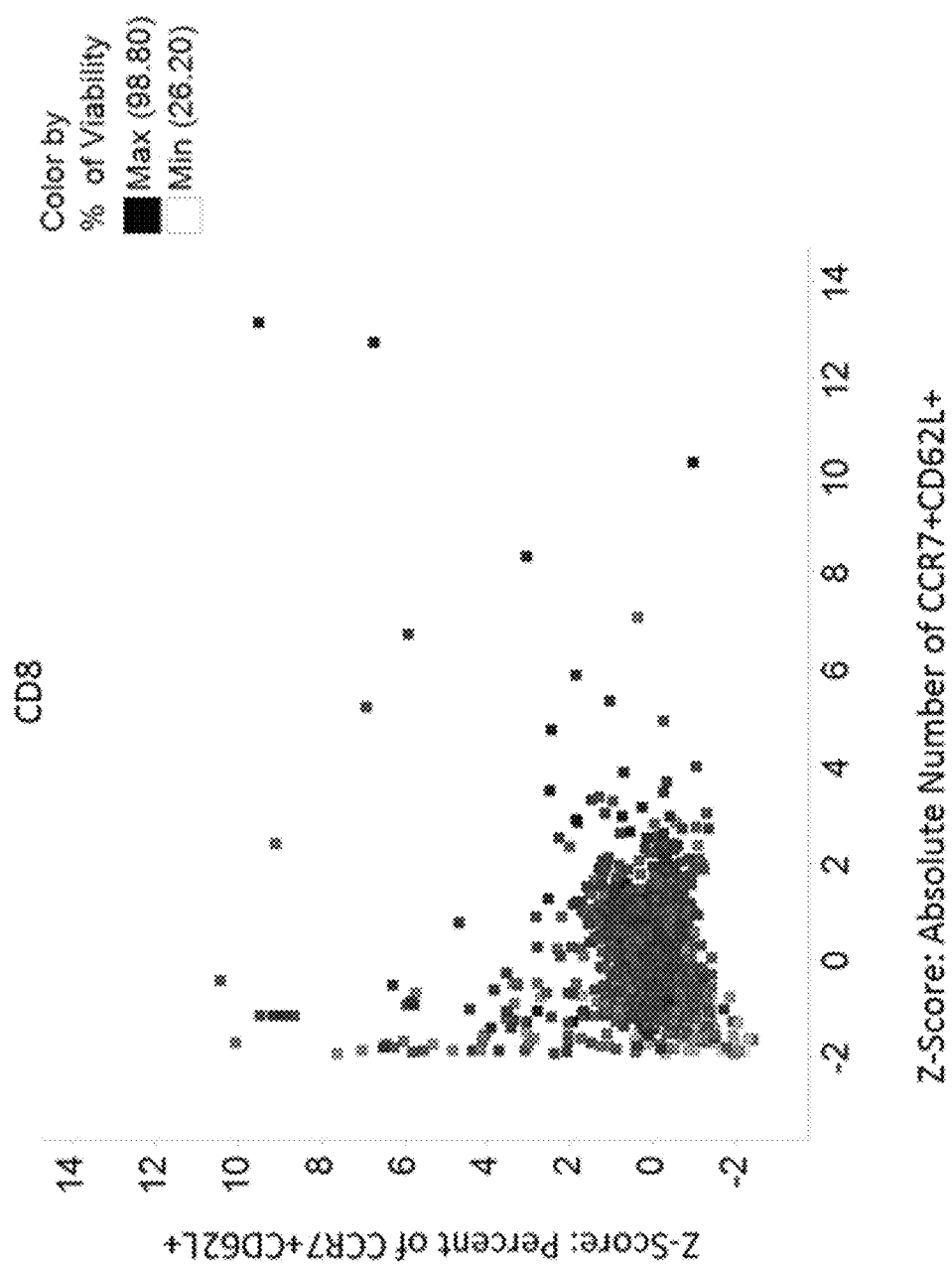
FIGS. 1A-1B are graphic representations of z-Score of the percentage of cells co-expressing both of CCR7 and CD62L, and a relative measure of the absolute number of naïve, stem cell memory, or central memory T cells in (FIG. 1A) the viable CD8+ cell population and (FIG. 1B) the viable CD4+ cell population.
Figure 1B:
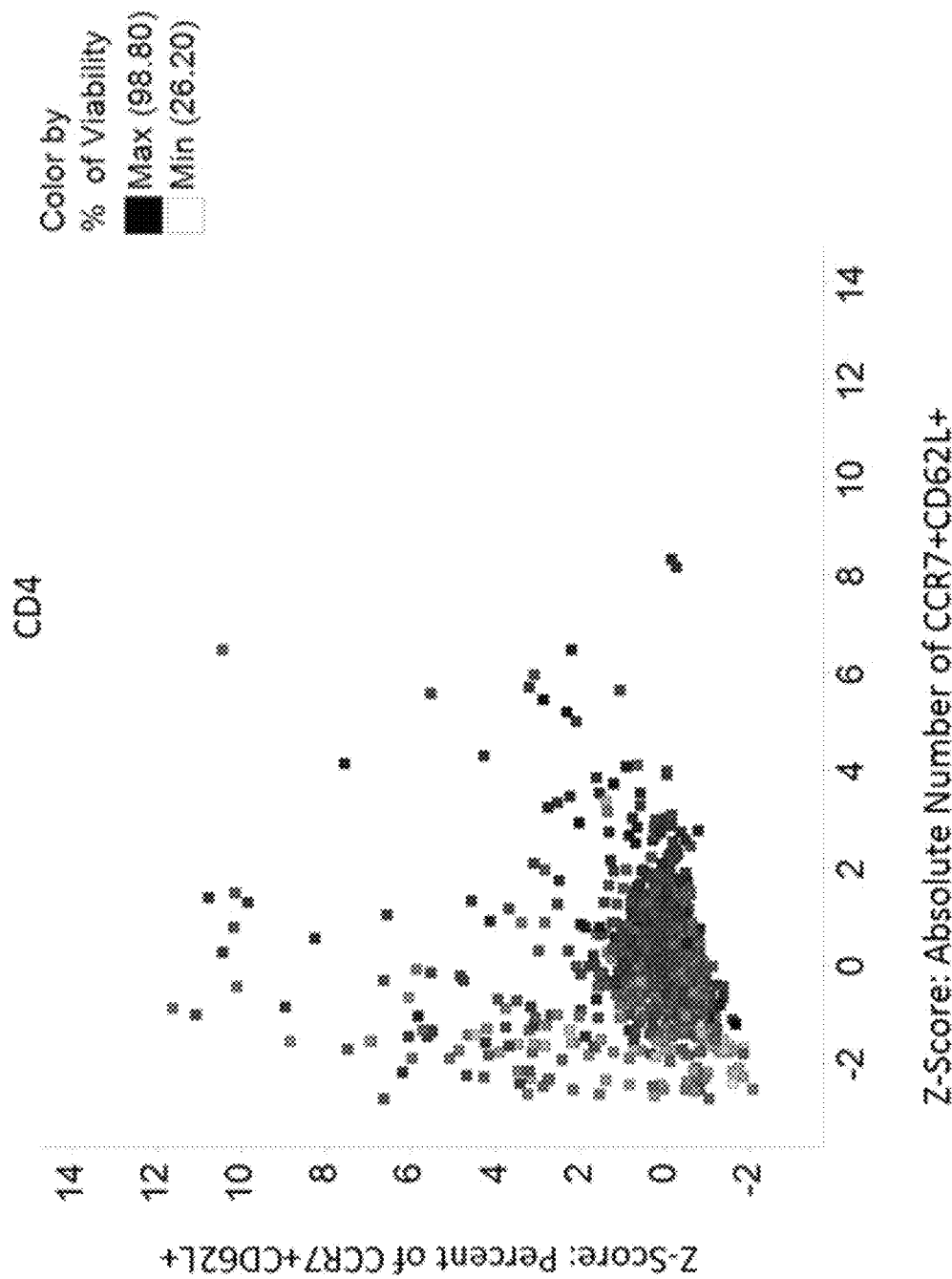

The present invention provides compositions and methods of modulating immune cell populations or subpopulations to obtain improved therapeutic potential for adoptive immunotherapies. The present invention also provides the method of using the modulated immune cells having improved therapeutic potential. In general, immune cells having improved therapeutic potential exhibit at least one of the following: improved proliferation, persistence, cytotoxicity, and/or cell recall/memory. The invention provides methods of improving immune cell therapeutic potential through improvements to the quality of the immune cells—for example, an increase in the number or ratio of a subpopulation of cells that displays improvement in at least one of the following qualities would be expected to result in better immunotherapeutic results: migration, homing, cytotoxicity, maintenance, expansion, persistence, longevity, differentiation, and/or de-differentiation of the same cells.

Definition

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" refer to one or to more than one of the grammatical object of the article. By way of example, a T cell means one T cell or more than one T cells.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3, Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

As used herein, the term "naïve T cell" or Tn, refers to mature T cells that, unlike activated or memory T cells, have not encountered their cognate antigen within the periphery. Naïve T cells are commonly characterized by the surface expression of L-selectin (CD62L); the absence of the activation markers CD25, CD44 or CD69; and the absence of the memory CD45RO isoform. They also express functional IL-7 receptors, consisting of subunits IL-7 receptor-α, CD127, and common-γ chain, CD132. In the naïve state, T cells are thought to be quiescent and non-dividing, requiring the common-gamma chain cytokines IL-7 and IL-15 for homeostatic survival mechanisms.

As used herein, the term "central memory T cells" or Tcm, refers to a subgroup or subpopulation of T cells that have lower expression or pro-apoptotic signaling genes, for example, Bid, Bnip3 and Bad, and have higher expression of genes associated with trafficking to secondary lymphoid organs, which genes include CD62L, CXCR3, CCR7, in comparison to effector memory T cells, or Tem.

As used herein, the term "stem memory T cells," or "stem cell memory T cells", or Tscm, refers to a subgroup or subpopulation of T cells that are capable of self-renewing and generating Tcm, Tem and Teff (effector T cells), and express CD27 and lymphoid homing molecules such as CCR7 and CD62L, which are properties important for mediating long-term immunity. As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3− and CD56+, expressing and have at least one of CD57+, NKG2C and CD57, and optionally, CD16, but lack expression of one or more of the following: +, low PLZF, low SYK, FceRγ, and low FεFRγ, low EAT-2., low TIGIT, low PD1, low CD7, low CD161, high LILRB1, high CD45RO, and low CD45RA. In some embodiments, isolated subpopulations of CD56+NK cells comprise expression of NKG2C and CD57. In some other embodiments, isolated subpopulations of CD56+NK cells comprise expression of CD57, CD16, NKG2C, CD57, NKG2D, NCR ligands, NKp30, NKp40, NKp46, activating and inhibitory KIRs, NKG2A and/or DNAM-1. CD56+ can be dim or bright expression.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are currently recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or noninvariant type II NKT cells, display a more heterogeneous TCR αβ usage. Type I NKT cells are currently considered suitable for immunotherapy. Adaptive or invariant (type I) NKT cells can be identified with the expression of at least one or more of the following markers, TCR Vα24-Jα18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, tissue, biopsy. The term also includes a cell that is removed from at least one, some or all components as the cell is found in non-naturally occurring environments, for example, culture, cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cells, substantially pure cells and cells cultured in a medium that is non-naturally occurring. Isolated cells may be obtained from separating the desired cells, or populations thereof, from other substances or cells in the environment, or from removing one or more other cell populations or subpopulations from the environment. As used herein, the term "purify" or the like refers to increasing purity. For example, the purity can be increased to at least 50%, 60%, 70%, 80%, 90%, 95%, 99%, or 100%.

As used herein, the term "population" when used with reference to T, NK or NKT cells refers to a group of cells including two or more T, NK, or NKT cells, respectively. Using T cell as an example, the isolated, or enriched, population of T cells may include only one type of T cell, or may include a mixture of two or more types of T cell. The isolated population of T cells can be a homogeneous population of one type of T cell or a heterogeneous population of two or more types of T cell. The isolated population of T cells can also be a heterogeneous population having T cells and at least a cell other than a T cell, e.g., a B cell, a macrophage, a neutrophil, an erythrocyte, a hepatocyte, an endothelial cell, an epithelial cell, a muscle cell, a brain cell, etc. The heterogeneous population can have from 0.01% to about 100% T cell. Accordingly, an isolated population of T cells can have at least 50%, 60%, 70%, 80%, 90%, 95%, 98%, or 99% T cells. The isolated population of T cells can include one or more, or all of, the different types of T cells, including but not limited to those disclosed herein. In an isolated population of T cells that includes more than one type of T cells, the ratio of each type of T cell can range from 0.01% to 99.99%. The isolated population also can be a clonal population of T cells, in which all the T cells of the population are clones of a single T cell.

An isolated population of T, NK or NKT cells may be obtained from a natural source, such as human peripheral blood or cord blood. Various ways of dissociating cells from tissues or cell mixtures to separate the various cell types have been developed in the art. In some cases, these manipulations result in a relatively homogeneous population of cells. The T cells can be isolated by a sorting or selection process as described herein or by other methods known in the art. The proportion of T cells in the isolated population may be higher than the proportion of T cells in the natural source by at least about 10%, about 20%, about 30%, about 40%, about 50%, about 60%, about 70%, about 80%, about 85%, about 90%, or about 95%. The isolated population of T cells can be for T cells in general, or one or more specific types of T cells.

As used herein, the term "subpopulation" when used in reference to T, NK or NKT cells refers to a population of T, NK or NKT cells that includes less than all types of T, NK, or NKT cells, respectively, that are found in nature.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, "iPSCs," refers to stem cells produced from differentiated adult cells that have been induced or changed (i.e. reprogrammed) into cells capable of differentiating into tissues of all three germ or dermal layers: mesoderm, endoderm, and ectoderm.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta and are not totipotent.

As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" in intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein, the term "ex vivo" refers to activities that take place outside an organism, such as experimentation or measurements done in or on living tissue in an artificial environment outside the organism, preferably with minimum alteration of the natural conditions. The "ex vivo" procedures can involve living cells or tissues taken from an organism and cultured in a laboratory apparatus, usually under sterile conditions, and typically for a few hours or up to about 24 hours, but including up to 2 to 28 days, depending on the circumstances. Such tissues or cells can also be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo. Meanwhile, an "in vivo" activity takes place inside an organism, such as cell engraftment, cell homing, self-renewal of cells, and expansion of cells.

As used herein, the term "in vitro" refers to activities performed or taking place in a test tube, culture dish, or elsewhere outside a living organism.

As used herein, the terms "agent," "modulating agent," and "modulator" are used interchangeably herein to refer to a compound or molecule capable of modifying gene expression profile or a biological property of a cell including an immune cell. The agent can be a single compound or molecule, or a combination of more than one compound or molecule.

As used herein, the terms "contact," "treat," or "modulate," when used in reference to an immune cell, are used interchangeably herein to refer to culturing, incubating or exposing an immune cell with one or more of the agents disclosed herein.

As used herein, a "noncontacted" or an "untreated" cell is a cell that has not been treated, e.g., cultured, contacted, or incubated with an agent other than a control agent. Cells contacted with a control agent, such as DMSO, or contacted with another vehicle are examples of noncontacted cells.

As used herein, "feeder cells" or "feeders" are terms describing cells of one type that are co-cultured with cells of a second type to provide an environment in which the cells of the second type can grow, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

As used herein, the term "analogue" refers to a chemical molecule that is similar to another chemical substance in structure and function, differing structurally by one single element or group, or more than one group (e.g., 2, 3, or 4 groups) if it retains the same chemical scaffold and function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Analogues can also include conjugates, such as biotin or avidin moieties, enzymes such as horseradish peroxidase and the like, and including radio-labeled, bioluminescent, chemoluminescent, or fluorescent moieties. Also, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.).

As used herein, the term "increase" refers to the ability of an agent to produce or cause a greater physiological response (i.e., downstream effects) in a cell, as compared to the response caused by either vehicle or a control molecule/composition, e.g., increased production of interleukin 4 or interleukin 10 by an isolated population of T cells. The increase can be an increase in gene expression as a result of increased signaling through certain cell signaling pathways. An "increased" amount is typically a statistically significant amount, and can include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) compared to the response produced by vehicle (the absence of an agent) or a control composition.

As used herein, the term "decrease" refers to the ability of an agent to produce or cause a lesser physiological response (i.e., downstream effects) in a cell, as compared to the response caused by either vehicle or a control molecule/composition. The decrease can be a decrease in gene expression, a decrease in cell signaling, or a decrease in cell proliferation. An "decreased" amount is typically a "statistically significant" amount, and can include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle (the absence of an agent) or a control composition.

As used herein, the term "synergy" or "synergistic" refers to a combination of two or more entities for an enhanced effect such that the working together of the two or more entities produces an effect greater than the sum of their individual effects, as compared to "antagonistic," which is used when two or more entities in a combination counteract or neutralize each other's effect; and compared to "additive," which is used when two or more entities in a combination produce an effect nearly equal to the sum of their individual effects.

As used herein, the terms "substantially free of," when used to describe a composition, such as a cell population or culture media, refers to a composition that is free of a specified substance of any source, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. The range of quantity, level, value, number, frequency, percentage, dimension, size, amount, weight or length can be ±15%, ±10%, ±9%, 8%, ±7%, ±6%, ±5%, ±4%, ±3%, ±2%, or ±1% about a reference quantity, level, value, number, frequency, percentage, dimension, size, amount, weight or length.

As used herein, the term "subject," refers to a mammal. A subject can be a human or a non-human mammal such as a dog, cat, bovid, equine, mouse, rat, rabbit, or transgenic species thereof.

As used herein, the term "treat," and the like, when used in reference to a subject, refer to obtaining a desired pharmacologic and/or physiologic effect, including without limitation achieving an improvement or elimination of the symptoms of a disease. The effect can be prophylactic in terms of completely or partially preventing a disease or symptom thereof and/or can be therapeutic in terms of achieving an improvement or elimination of symptoms, or providing a partial or complete cure for a disease and/or adverse effect attributable to the disease. The term "treatment" includes any treatment of a disease in a mammal, particularly in a human, and includes: (a) preventing the disease from occurring in a subject which can be predisposed to the disease but has not yet been diagnosed as having it; (b) inhibiting the disease, or arresting its development; (c) relieving the disease, or causing regression of the disease, or to completely or partially eliminate symptoms of the disease; and (d) restoring the individual to a pre-disease state, such as reconstituting the hematopoietic system.

As used herein, "genetic modification" refers to genetic editing including those (1) naturally derived from rearrangements, mutations, genetic imprinting and/or epigenetic modification, (2) or obtained through genomic engineering through insertion, deletion or substitution in the genome of a cell. Genetic modification, as used herein, also includes one or more retainable therapeutic attributes of a source specific immune cell that is donor-, disease-, or treatment response-specific, As used herein, the term "genetic imprint" refers to genetic or epigenetic information that contributes to preferential therapeutic attributes in a source cell. In the aspect of a source cell obtained from a specifically selected donor, disease or treatment context, the genetic imprint contributing to preferential therapeutic attributes may include any context specific genetic or epigenetic modifications which manifest a retainable phenotype, i.e. a preferential therapeutic attribute, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof, resistance to tumor microenvironment; induction of bystander immune cells and immune modulations; improved on-target specificity with reduced off-tumor effect; resistance to treatment such as chemotherapy.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g. a prodrug, that when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

I. Agents for Improving Efficacy of Cell-Based Adoptive Immunotherapy

The present invention provides a composition comprising one or more agents in an amount sufficient for improving therapeutic potential of immune cells suitable for adoptive cell-based therapies. Immune cells having improved therapeutic potential present improved proliferation, persistence, cytotoxicity, and/or cell recall/memory. Immune cells may have specifically improved in vivo proliferation, in vivo persistence, in vivo cytotoxicity, and/or in vivo cell recall/memory. To improve immune cell therapeutic potential generally requires better quality of the immune cells—in a T cell population, for example, increased number or ratio of naïve T cell, stem cell memory T cell, and/or central memory T cell through maintenance, expansion, differentiation, and/or de-differentiation thereof are indicative of better quality of the T cells for improved in vivo adoptive therapeutic potential. In a NK cell population, for example, increased number or ratio of adaptive NK cells through maintenance, subtype skewing, expansion, differentiation, and/or de-differentiation thereof are indicative of better quality of the NK cells for improved in vivo adoptive therapeutic potential. With respect to a NKT cell population, for example, an increased number or ratio of type I NKT cells through maintenance, subtype switching, expansion, differentiation, and/or de-differentiation thereof are indicative of better quality of the NKT cells for improved in vivo adoptive therapeutic potential.

The immune cells suitable for adoptive cell-based therapies are contacted, treated, or modulated with one or more agents included in Table 1. The treatment with the agent(s) can modify the biological properties of the cells, or a subpopulation of the cells, including by modulating cell expansion, maintenance, differentiation, dedifferentiation, and/or survival rate, and/or increasing proliferation, cytotoxicity, persistence, and/or cell recall/memory, and thus the therapeutic potential of the cells treated. For example, the treatment can improve the therapeutic immune cell survival rate both in vitro and in vivo. Further, the treatment can alter the ratios of different subpopulation of the treated cell population. For example, in one embodiment, the number and proportion of naïve T cells, stem cell memory T cells, and/or central memory T cells increase in an isolated T cell population upon treatment using one or more of the agents selected from Table 1, and derivatives and analogs thereof. In another embodiment, upon treatment of a NK cell population using one or more of the agents selected from Table 1, and derivatives and analogs thereof, the number and percentage of adaptive NK cells are increased in the population.

TABLE 1

Agents for Immune Cell Modulation in Adoptive Cell Therapies

| Compounds | CAS Number | Group | Group Descriptor |
|---|---|---|---|
| Dorsomorphin | 866405-64-3 | I | Metabolism & Nutrient Sensing |
| Heptelidic acid | 74310-84-2 | I | Metabolism & Nutrient Sensing |
| 1-Pyrrolidine-carbodithioic acid, ammonium salt | 5108-96-3 | I | Metabolism & Nutrient Sensing |
| 2-dexoyglucose (2-DG) | 154-17-6 | I | Metabolism & Nutrient Sensing |
| GSK3 Inhibitor | Including for example-BIO: 667463-62-9; TWS119: 601514-19-6; CHIR99021: 252917-06-9 | II | Signaling Pathways |
| Rho kinase inhibitors | Including for example-Thiazovivin: 1226056-71-8 | II | Signaling Pathways |
| MEK inhibitors | Including for example-PD0325901: 391210-10-9; U0126: 109511-58-2 | II | Signaling Pathways |
| PDK1 agonist | Including for example-PS48: 1180676-32-7 | II | Signaling Pathways |
| TGFβ inhibitors | Including for example-SB431542: 301836-41-9 | II | Signaling Pathways |
| 6-Mer-captopurine | 6112-76-1 | II | Signaling Pathways |
| AC-93253 iodide | 108527-83-9 | II | Signaling Pathways |
| Tiratricol | 51-24-1 | II | Signaling Pathways |
| PI-103 | 371935-74-9 | II | Signaling Pathways |
| Fulvestrant | 129453-61-8 | II | Signaling Pathways |
| Thapsigargin | 67526-95-8 | II | Signaling Pathways |
| SU 4312 | 5812-07-7 | II | Signaling Pathways |
| Telmisartan | 144701-48-4 | II | Signaling Pathways |
| Cyclosporin A | 59865-13-3 | II | Signaling Pathways |
| 1,3,5-tris(4-hydroxy-phenyl)-4-propyl-1H-pyrazole | 263717-53-9 | II | Signaling Pathways |
| BAY 61-3606 | 732983-37-8 | II | Signaling Pathways |
| Protoporphyrin IX disodium | 553-12-8 | II | Signaling Pathways |
| mTOR inhibitor | Including for example-Rapamycin: 53123-88-9 | II | Signaling Pathways |
| HS173 | 1276110-06-5 | II | Signaling Pathways |
| LY294002 | 154447-36-6 | II | Signaling Pathways |
| Pictilisib | 957054-30-7 | II | Signaling Pathways |
| 5-Azacytidine | 320-67-2 | III | Proliferation and Apoptosis |
| Fludarabine | 21679-14-1 | III | Proliferation and Apoptosis |
| Roscovitine, (S)-Isomer | 186692-45-5 | III | Proliferation and Apoptosis |
| PAC-1 | 315183-21-2 | III | Proliferation and Apoptosis |
| 8-Quinolinol, 5,7-dichloro- | 773-76-2 | IV | Anti-infective |
| Nitrofurantoin | 67-20-9 | IV | Anti-infective |
| 8-Quinolinol, 5-chloro-7-iodo- | 130-26-7 | IV | Anti-infective |

TABLE 1-continued

Agents for Immune Cell Modulation in Adoptive Cell Therapies

| Compounds | CAS Number | Group | Group Descriptor |
|---|---|---|---|
| 2-Naphthacene-carboxamide, 7-chloro-4-(dimethyl-amino)-1,4,4a,5,5a,6,11,12a-octahy | 64-73-3 | IV | Anti-infective |
| Nifuroxazide | 965-52-6 | IV | Anti-infective |
| Tosufloxacin hydrochloride | 100490-36-6 | IV | Anti-infective |
| Sertraline | 79617-96-2 | V | Other |
| Diethylene-triamine-pentaacetic acid, penta sodium | 67-43-6 | V | Other |
| Edrophonium chloride | 116-38-1 | V | Other |
| BIX01294 | 1392399-03-9 | V | Other |
| Terfenadine | 50679-08-8 | V | Other |
| dmPGE2 (16,16-dimethyl Prostaglandin E2) | 39746-25-3 | V | Other |

Without being limited by the theory, the agents of Table 1 improve the therapeutic potential of an immune cell for adoptive therapy by modulating cell expansion, metabolism, and/or cell differentiation via regulating cell metabolism, nutrient sensing, proliferation, apoptosis, signal transduction, properties relating to infective process, and/or other aspects of cell function. As understood by those skilled in the art, the scope of the present invention also includes analogues or derivatives, including but not limited to, salt, ester, ether, solvate, hydrate, stereoisomer or prodrug of the listed agents in Table 1. For example, illustrative examples of analogues and derivatives of a Table 1 agent, dmPGE$_2$ (16,16-dimethyl Prostaglandin E2), include, without limitation, PGE$_2$, 16,16-dimethyl PGE$_2$ p-(p-acetamidobenzamido) phenyl ester, 11-deoxy-16,16-dimethyl PGE$_2$, 9-deoxy-9-methylene-16, 16-dimethyl PGE$_2$, 9-deoxy-9-methylene PGE$_2$, 9-keto Fluprostenol, 5-trans PGE$_2$, 17-phenyl-omega-trinor PGE$_2$, PGE$_2$ serinol amide, PGE$_2$ methyl ester, 16-phenyl tetranor PGE$_2$, 15(S)-15-methyl PGE$_2$, 15(R)-15-methyl PGE$_2$, 8-iso-15-keto PGE$_2$, 8-iso PGE2 isopropyl ester, 8-iso-16-cyclohexyl-tetranor PGE$_2$, 20-hydroxy PGE$_2$, 20-ethyl PGE$_2$, 11-deoxy PGEi, nocloprost, sulprostone, butaprost, 15-keto PGE$_2$, and 19 (R) hydroxy PGE$_2$. Also included are PG analogues or derivatives having a similar structure to PGE$_2$ that are substituted with halogen at the 9-position (see, e.g., WO 2001/12596, the disclosure of which is hereby incorporated by reference in its entirety), as well as 2-decarboxy-2-phosphinico prostaglandin derivatives, such as those described in U.S. Publication No. 2006/0247214, the disclosure of which is hereby incorporated by reference in its entirety).

GSK3 (Glycogen synthase kinase 3) inhibitors can include antibodies that bind, dominant negative variants of, and siRNA, microRNA, antisense nucleic acids, and other polynucleotides that target GSK3. Suitable GSK3 inhibitor (GSK3i) for use in compositions contemplated herein include, but are not limited to: Kenpaullone, 1-Azakenpaullone, CHIR99021, CHIR98014, AR-A014418, CT 99021, CT 20026, SB216763, AR-A014418, lithium, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)-[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl]-4-pyrazin-2-yl-pyrrole-2,5-dione; TWS119, L803 H-KEAPPAPPQSpP-NH2 or its myristoylated form; 2-Chloro-1-(4,5-dibromo-thiophen-2-yl)-ethanone; GF109203X; RG318220; TDZD-8; TIBPO; and OTDZT. In one embodiment, the GSK-3 inhibitor is CHIR99021, BIO, TWS119, or Kenpaullone. In one embodiment, the GSK3 inhibitor is TWS119. In another embodiment, the GSK-3 inhibitor is CHIR99021. In yet another embodiment the GSK3 inhibitor is BIO.

MEK/ERK pathway inhibitors refer to inhibitors of either MEK or ERK serine/threonine kinases that are part of the Raf/MEK/ERK pathway. ERK/MEK inhibitors suitable for use in compositions contemplated herein include, but not limited to: PD0325901, PD98059, U0126, SL327, ARRY-162, PD184161, PD184352, sunitinib, sorafenib, vandetanib, pazopanib, axitinib, GSK1 120212, ARRY-438162, RGO126766, XL518, AZD8330, RDEA1 19, AZD6244, FR180204, PTK787, 6-(4-Bromo-2-chloro-phenylamino)-7-fluoro-3-methyl-3H-benzoimidazol-e-5-carboxylic acid (2,3-dihydroxy-propoxy)-amide; 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimida-zol-5-yl]-2-hydroxy-ethanone, 6-(4-Bromo-2-chloro-phenylamino)-7-fluoro-3-methyl-3H-benzoimidazol-e-5-carboxylic acid (2-hydroxy-1,1-dimethyl-ethoxy)-amide, 6-(4-Bromo-2-chloro-phenylamino)-7-fluoro-3-(tetrahydro-furan-2-ylm-ethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazol-e-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazol-e-5-carboxylic acid (2-hydroxy-ethoxy)-amide, 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2; and 4-(4-bromo-2-fluorophenylamino)-N-(2-hydroxyethoxy)-1,5-dimethyl-6-oxo-1,6-dihydropyridazine-3-carboxamide or a pharmaceutically acceptable salt thereof. Additional illustrative MEK/ERK inhibitors include those compounds disclosed in International Published Patent Applications WO 99/01426, WO 02/06213, WO 03/077914, WO 05/051301 and WO2007/044084. In one embodiment, the MEK inhibitor is PD0325901. In another embodiment, the MEK inhibitor is U0126.

ROCK (Rho associated kinases) inhibitors refer to inhibitors of the Rho-GTPase/ROCK pathway. The pathway includes the downstream protein Myosin II, which is further downstream of ROCK (Rho-ROCK-Myosin II forms the pathway/axis). Thus, one can use any or all of a Rho GTPase inhibitor, a ROCK inhibitor, or a Myosin II inhibitor to achieve the effects described herein. ROCK inhibitors suitable for use in compositions contemplated herein include, but are not limited to: thiazovivin, Y27632, fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, (R)-(+)-trans-N-(4-Pyridyl)-4-(1-aminoethyl)-cyclohexanecarboxamide, and ROCK inhibitors disclosed in U.S. Pat. No. 8,044,201, which is herein incorporated by reference in its entirety. In one embodiment, the ROCK inhibitor is thiazovivin, Y27632, or pyrintegrin. In one embodiment, the ROCK inhibitor is thiazovivin.

Activin receptor-like kinase 5 (ALK5) is the principal TGFβ receptor that mediates cellular responses to TGFβs. Upon ligand binding, constitutively active TβRII kinase phosphorylates ALK5 which, in turn, activates the downstream signal transduction cascades. TGFβ receptor/ALK5 inhibitors can include antibodies to, dominant negative variants of, and siRNA, microRNA, antisense nucleic acids, and other polynucleotides that suppress expression of, TGFβ/ALK5 receptors. TGFβ receptor/ALK5 inhibitors suitable for use in compositions contemplated herein include, but are not limited to: SB431542; A-83-01 (3-(6-Methyl-2-pyridinyl)-N-phenyl-4-(4-quinolinyl)-1H-pyrazole-1-carbothioamide; 2-(3-(6-Methylpyridin-2-yl)-1H-pyrazol-4-yl)-1,5-naphthyridine, Wnt3a/BIO, GW788388 (-{4-[3-(pyridin-2-yl)-1H-pyrazol-4-yl]pyridin-2-yl}-N-(tetrahydro-2H-pyran-4-yl)benzamide), SM16, IN-1130 (3-((5-(6-methylpyridin-2-yl)-4-(quinoxalin-6-yl)-1H-imidazol-2-yl)methyl)benzamide), GW6604 (2-phenyl-4-(3-pyridin-2-yl-1H-pyrazol-4-yl)pyridine), SB-505124 (2-(5-benzo[1,3]dioxol-5-yl-2-tert-butyl-3H-imidazol-4-yl)-6-methylpyridine hydrochloride); SU5416; 2-(5-benzo[1,3] dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). It is further believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described herein are merely for organizational purposes and one of skill in the art would know that compounds can affect one or more points within a pathway, and thus compounds may function in more than one of the defined categories. In one embodiment, the TGFβ receptor inhibitor comprises SB431542.

PDK1 or 3'-phosphoinositide-dependent kinase-1 is a master kinase associated with the activation of AKT/PKB and many other AGC kinases including PKC, S6K, SGK. An important role for PDK1 is in the signaling pathways activated by several growth factors and hormones including insulin signaling. Exemplary PDK1 agonists include sphingosine (King et al, Journal of Biological Chemistry, 275: 18108-18113, 2000). Exemplary allosteric activators of PDK1 include PS48 ((Z)-5-(4-Chlorophenyl)-3-phenylpent-2-enoic acid), PS08 ((Z)-5-(4-Bromo-2-fluorophenyl)-3-phenylpent-2-enoic acid), 1-(2-(3-(4-Chlorophenyl)-3-oxo-1-phenylpropylthio)acetic acid; 3,5-diphenylpent-2-enoic acids such as compound 12Z (2-(3-(4-Chlorophenyl)-3-oxo-1-phenylpropylthio)acetic acid, (Z)-5-(Napthalen-2-yl)-3-phenylpent-2-enoic acid), and compound 13Z ((Z)-5-(1H-Indol-3-yl)-3-phenylpent-2-enoic acid). In one embodiment, the PDK1 agonist comprises PS48.

Mammalian target of rapamycin (mTOR) inhibitors block the activity of the mammalian target of rapamycin. mTOR is a protein kinase, which regulates growth factors that stimulate cell growth and angiogenesis. mTOR inhibitors suitable for the composition and method of the present invention include, but not limited to rapamycin, and analogues and derivatives thereof comprising sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives.

In some embodiments, the composition for improving therapeutic potential of immune cells suitable for adoptive cell-based therapies comprises at least one agent selected from Table 1, and derivatives and analogs thereof. In one embodiment, the composition for improving therapeutic potential of immune cells comprises a combination of at least 2, 3, 4, 5, or 6, or any number, of the agents selected from Table 1, and derivatives and analogs thereof.

In one embodiment, the composition comprising at least one agent selected from Table 1 further comprises an organic solvent. In certain embodiments, the organic solvent is substantially free of methyl acetate. In certain embodiments, the organic solvent is selected from the group consisting of dimethyl sulfoxide (DMSO), N,N-dimethylformamide (DMF), dimethoxyethane (DME), dimethylacetamide, ethanol, and combinations thereof. In some embodiments, the organic solvent is DMSO. In some embodiments, the organic solvent is ethanol. In some other embodiments, the organic solvent is a mixture of DMSO and ethanol.

In some embodiments, the composition for improving therapeutic potential of immune cells suitable for adoptive cell-based therapies comprises at least one agent selected from Group I: dorsomorphin, heptelidic acid, 1-Pyrrolidinecarbodithioic acid, and 2-DG. Without being limited to the theory, Group I agents, among other potential roles, may impact cell metabolism and nutrient sensing.

In some embodiments, the composition for improving therapeutic potential of immune cells suitable for adoptive cell-based therapies comprises at least one agent selected from Group II. GSK3 Inhibitor, ROCK inhibitor, TGFβ receptor inhibitor, MEK inhibitor, PDK1 agonist, 6-Mercaptopurine, AC-93253 iodide, tiratricol, PI-103, fulvestrant, thapsigargin, SU 4312, U0126, telmisartan, cyclosporin A, 1,3,5-tris(4-hydroxyphenyl)-4-propyl-1H-pyrazole, BAY 61-3606, protoporphyrin IX disodium, mTOR inhibitor, TWS119, HS173, LY294002, and Pictilisib. Without being limited to the theory, Group II agents, among other potential roles, may impact signal transduction in various functional pathways. In one embodiment, the agent selected from Group II is an mTOR inhibitor. In one embodiment, the agent selected from Group II is rapamycin, or an analogue or derivative thereof. In some embodiments, the analogues or derivatives of rapamycin include, but not limited to, sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives.

In some embodiments, the composition for improving therapeutic potential of immune cells suitable for adoptive cell-based therapies comprises at least one agent selected from Group III: 5-Azacytidine, fludarabine, roscovitine, and PAC-1. Without being limited to the theory, Group III agents, among other potential roles, may impact cell proliferation and apoptosis.

In some embodiments, the composition for improving therapeutic potential of immune cells suitable for adoptive cell-based therapies comprises at least one agent selected from Group IV: 5,7-dichloro-8-Quinolinol, 2-Naphthacenecarboxamide, 7-chloro-4-(dimethylamino)-1,4,4a,5,5a,6,11,12a-octahy, Nifuroxazide, and Tosufloxacin hydrochloride. Without being limited to the theory, Group IV agents, among other potential roles, may impact cell properties relating to infective processes.

In some embodiments, the composition for improving therapeutic potential of immune cells suitable for adoptive cell-based therapies comprises at least one agent selected from Group V: sertraline, diethylenetriaminepentaacetic acid, edrophonium chloride, BIX01294, terfenadine, and dmPGE2. Without being limited to the theory, Group V agents, among other potential roles, generally may impact other cell properties relating to expansion, maintenance differentiation, dedifferentiation, survival rate, proliferation, cytotoxicity, cell recall, and/or persistence.

In yet some other embodiments, the composition for improving therapeutic potential of immune cells suitable for adoptive cell-based therapies comprises at least one agent selected from Group I, and one or more agents selected from Group II, Group III, Group IV, and/or Group V.

In some other embodiments, the composition for improving therapeutic potential of immune cells suitable for adoptive cell-based therapies comprises at least one agent selected from Group II, and one or more agents selected from Group I, Group III, Group IV, and/or Group V. In one embodiment, the composition comprise an agent selected from Group II and an agent selected from Group V. In one embodiment, the agent selected from Group II is an mTOR inhibitor. In one embodiment, the agent selected from Group II is rapamycin, or an analogue or derivative thereof. In some embodiments, the analogues or derivatives of rapamycin include, but not limited to, sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives. In one embodiment the agent selected from Group V is dmPGE2, or an analogue or derivative thereof.

In yet some other embodiments, the composition for improving therapeutic potential of immune cells suitable for adoptive cell-based therapies comprises at least one agent selected from Group III, and one or more agents selected from Group I, Group II, Group IV, and/or Group V.

In still some other embodiments, the composition for improving therapeutic potential of immune cells suitable for adoptive cell-based therapies comprises at least one agent selected from Group IV, and one or more agents selected from Group I, Group II, Group III, and/or Group V.

In still some other embodiments, the composition for improving therapeutic potential of immune cells suitable for adoptive cell-based therapies comprises at least one agent selected from Group IV, and one or more agents selected from Group I, Group II, Group III, and/or Group IV.

In some embodiments, the composition for improving therapeutic potential of immune cells suitable for adoptive cell-based therapies comprises at least one agent selected from a group consisting of a GSK3 inhibitor, a MEK inhibitor, a ROCK inhibitor, a TGFβ inhibitor, a PDK1 agonist, and an mTOR inhibitor.

In some embodiments, the composition comprises a combination of two or more agents selected from Table 1, wherein the agents have additive effect in the combination. As defined, "additive" refers to when two or more agents in a combination produce an effect nearly equal to the sum of their individual effects. In some embodiments, one or more of the agents in a combination are from the same group: Group I, II, III, IV, or V. In some embodiments, one or more of the agents in a combination are from different groups.

In some embodiments, the composition for improving therapeutic potential of immune cells comprises a combination of rapamycin and dmPGE2, or any combination of their respective analogues and derivatives.

In some embodiments, the composition comprises a synergistic combination of two or more agents selected from Table 1. As defined, "synergy" is an enhanced effect such that the working together of two or more agents to produce an effect greater than the sum of their individual effects. In one embodiment, the composition comprising a synergistic combination comprises at least one agent selected from the group consisting of TWS119, HS173, LY294002, Pictilisib, and 2-DG. In one embodiment, the composition comprises a combination comprising at least one agent selected from the group consisting of TWS119, HS173, LY294002, Pictilisib, and 2-DG, and one or more additional agent selected from the group of compounds listed in Table 1. In one embodiment, the composition comprising TWS119, further comprises two or more additional agents selected from Table 1. In one embodiment, the composition comprising HS173, further comprises two or more additional agents selected from Table 1. In one embodiment, the composition comprising LY294002, further comprises two or more additional agents selected from Table 1. In one embodiment, the composition comprising Pictilisib, further comprises two or more additional agents selected from Table 1. In one embodiment, the composition comprising 2-DG, further comprises two or more additional agents selected from Table 1.

In some embodiments, the composition comprising one or more agents selected from the group consisting of the compounds listed in Table 1, further comprises one of more additional additives selected from the group consisting of peptides, cytokines, mitogens, growth factors, small RNAs, dsRNAs (double stranded RNA), mononuclear blood cells, feeder cells, feeder cell components or replacement factors, vectors comprising one or more polynucleic acids of interest, antibodies and antibody fragments thereof, and/or chemotherapeutic agent or radioactive moiety. In some embodiments, the additional additive comprises an antibody, or an antibody fragment. In some of these embodiments, the antibody, or antibody fragment, specifically binds to a viral antigen. In other embodiments, the antibody, or antibody fragment, specifically binds to a tumor antigen.

In some embodiments, the cytokine and growth factor comprise one or more of the following cytokines or growth factors: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-γ), stem cell factor (SCF) and erythropoietin (Epo). In some embodiments, the cytokine comprises at least interleukin-2 (IL-2), interleukin 7 (IL-7), interleukin-12 (IL-12), interleukin-15, interleukin 18 (IL-18), interleukin 21 (IL-21), or any combinations thereof. In some embodiments, the growth factor of the composition comprises fibroblast growth factor. These cytokines may be obtained commercially, for example from R&D Systems (Minneapolis, Minn.), and may be either natural or recombinant. In particular embodiments, growth factors and cytokines may be added at concentrations contemplated herein. In certain embodiments growth factors and cytokines may be added at concentrations that are determined empirically or as guided by the established cytokine art.

In some embodiments, the mitogen of the composition comprises concanavalin A. In some other embodiments, the feeder cells are genetically modified. In some embodiments, the feeder cells comprise one or more of the followings: mononuclear blood cells, thymic epithelial cells, endothelial cells, fibroblasts, leukemic cells K562, Raji cells, or feeder cell components or replacement factors thereof.

In some embodiments, the small RNA comprises one or more of siRNA, shRNA, miRNA and antisense nucleic acids. In some other embodiments, the small RNA comprises one or more of the followings: miR-362-5p, miR-483-3p, miR-210 and miR-598.

In some embodiments, the vector comprising one or more polynucleic acids of interest is integrating or non-integrating. In some embodiments, the vector comprising one or more polynucleic acids of interest further comprises backbones of an adenovirus vector, plasmid vector, adeno-associated virus vector, retrovirus vector, lentivirus vector, Sendai virus vector, episomal vector and the like. In some embodiments, the plasmid vectors for the expression in animal cells include, for example, pA1-11, pXT1, pRc/CMV, pRc/RSV, pcDNAI/Neo, and the like. In some embodiments, the one or more polynucleic acids comprised in the vector encode one or more proteins or polypeptides. In some embodiments, the one or more polynucleic acids encode Delta-like 1 (DLL1), Delta-like 3 (DLL3), Delta-like 4 (DLL4), Jagged1 (Jag1), or Jagged2. In some embodiments, the one or more polynucleic acids encode Jagged 1.

II. Immune Cells for Adoptive Cellular Therapies

The present invention provides a composition comprising an isolated population or subpopulation of immune cells that have been contacted with one or more agents selected from Table 1. In one embodiment, the isolated population or subpopulation of immune cells have been contacted with one or more agents selected from Table 1 in an amount sufficient to improve the therapeutic potential of the immune cells. In some embodiments, the treated immune cells are used in a cell-based adoptive therapy. The present invention further provides a population or subpopulation of immune cells, and one or more agents selected from the agents listed in Table 1, wherein a treatment of the population or subpopulation of immune cells using the one or more agents selected from the agents listed in Table 1 improves the therapeutic potential of the immune cells for adoptive therapy. The treatment can modify the biological properties of the immune cells to improve cell proliferation, cytotoxicity, and persistence, and/or reduce the relapse rate of the cell therapy.

In some embodiments, the population of immune cells comprises T cells. In some embodiments, the population of immune cells comprises NK cells. In some embodiments, the population of immune cell comprises NKT cell.

In some embodiments, a population or subpopulation of T cells contacted with one or more agents selected from Table 1 comprises an increased number or ratio of naïve T cells (Tn), stem cell memory T cells (Tscm), and/or central memory T cells (Tcm), and/or improved cell proliferation, cytotoxicity, cell recall, and/or persistence in comparison to the T cells without the same treatment. In some embodiments the number of Tn, Tscm, and/or Tcm is increased by at least 10%, 20%, 30%, 40%, 50%, 60%, 70%, 80%, 90%, or increased by at least 5, 10, 15, or 20 fold compared to the number of Tn, Tscm, and/or Tcm in the cell population without the same treatment with one or more agents selected from Table 1.

In some embodiments, a population or subpopulation of NK cells contacted with one or more agents selected from Table 1 comprises an increased number or ratio of adaptive (or memory) NK cells, and/or improved cell proliferation, cytotoxicity, cell recall, and/or persistence in comparison to the NK cells without the same treatment. In some embodiments the number of adaptive NK cells is increased by at least 10%, 20%, 30%, 40%, 50%, 60%, 70%, 80%, 90%, or increased by at least 5, 10, 15, or 20 fold compared to the number of adaptive NK cells in the cell population without the same treatment with one or more agents selected from Table 1. In one embodiment, a population or subpopulation of NK cells contacted with a GSK3 inhibitor, a MEK inhibitor, a ROCK inhibitor, a TGFβ inhibitor, a PDK1 agonist, and/or rapamycin comprises an increased number or ratio of adaptive NK cells. In one embodiment, the adaptive NK cell is characterized by CD3− and CD56+, and at least one of CD57+, NKG2C+, low PLZF, low SYK, low FεFRγ, low EAT-2, low TIGIT, low PD1, low CD7, low CD161, high LILRB1, high CD45RO, and low CD45RA. In some embodiments, the adaptive NK cells are at least two of CD57+, NKG2C+, low PLZF, low SYK, low FεFRγ, low EAT-2, low TIGIT, low PD1, low CD7, low CD161, high LILRB1, high CD45RO, and low CD45RA. For example, the adaptive NK cell can be CD57+ and NKG2C+. In some embodiments, the adaptive NK cells are at least three of CD57+, NKG2C+, low PLZF, low SYK, low FεFRγ, low EAT-2, low TIGIT, low PD1, low CD7, low CD161, high LILRB1, high CD45RO, and low CD45RA. For example, the adaptive NK cell can be SYK-, FεFRγ-, and EAT-2-. In one embodiment, the GSK-3β inhibitor is CHIR99021, BIO, TWS119, or Kenpaullone. In one embodiment, the GSK-3β inhibitor is TWS119. In another embodiment, the GSK-3β inhibitor is CHIR99021. In yet another embodiment the GSK-3β inhibitor is BIO. In one embodiment, the mTOR inhibitor is rapamycin, or an analogue or a derivative thereof comprising sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives.

In some other embodiments, a population or subpopulation of NKT cells contacted with one or more agents selected from Table 1 comprises an increased number or ratio of type I NKT cells vs type II, and/or improved cell proliferation, cytotoxicity, cell recall, and/or persistence in comparison to the isolated population or subpopulation of NKT cells without the treatment with one or more agents selected from Table 1. In some embodiments the number of type I NKT cells is increased by at least 10%, 20%, 30%, 40%, 50%, 60%, 70%, 80%, 90%, or increased by at least 5, 10, 15, or 20 fold compared to the number of type I NKT cells in the cell population without the same treatment with one or more agents selected from Table 1.

In some embodiments, the increased number or ratio of naïve T cells (Tn), stem cell memory T cells (Tscm), central memory T cells (Tcm), adaptive NK cells, and/or type I NKT cells are due to improved maintenance and expansion of these cell subtypes, and/or increased cell dedifferentiation/reprogramming from more mature cell subtypes to cell subtypes in a desired differentiation state.

In some embodiments, after contacting a population of immune cell with one or more of the agents included in Table 1, the number of naïve T cells (Tn), stem cell memory T cells (Tscm), central memory T cells (Tcm) in the population is increased in comparison to untreated immune cell population, wherein the Tn, Tscm and Tcm are characterized by co-expression of CCR7 and/or CD62L.

In some embodiments, after contacting a population of immune cells with one or more of the agents included in Table 1, the number of adaptive NK cells in the population is increased in comparison to untreated immune cell population, wherein the adaptive NK cells are characterized by CD3−, CD56+, CD16+, NKG2C+, and CD57+. In some other embodiments, the adaptive NK cells are characterized by CD3−, CD56+, and at least one, two or three of CD57+, NKG2C+, low PLZF, low SYK, low FεRγ, low EAT-2, low TIGIT, low PD1, low CD7, low CD161, high LILRB1, high CD45RO, and low CD45RA.

In some embodiments, after contacting a population of immune cells with one or more of the agents included in Table 1, the number of type I NKT cells in the population is increased in comparison to untreated immune cell population, wherein the type I NKT cells are characterized by surface antigens CD3+, CD56+, TCR Vα24+, and/or TCR Vβ11+.

In some embodiments, the population or subpopulation of T, NK or NKT cells for treatment by the agents disclosed herein can be isolated from a human or a non-human mammal. Examples of such non-human mammals include, but are not limited to rabbit, horse, bovine, sheep, pigs, dogs, cats, mice, rats, and transgenic species thereof.

The population or subpopulation of T cells can be obtained or isolated from a number of sources, including but not limited to peripheral blood, bone marrow, lymph node tissue, cord blood, thymus tissue, and tissue from a site of infection, ascites, pleural effusion, spleen tissue, and tumors. The bone marrow can be obtained from femurs, iliac crest, hip, ribs, sternum, and other bones. In addition, the T cell lines available in the art can also be used, such as Jurkat, SupT1, and others.

The population or subpopulation of NK cells can be obtained, or can be enriched, from a number of sources, including but not limited to peripheral blood, cord blood, and tumors.

Fully mature NKT cells can be obtained, or can be enriched, from peripheral blood, with smaller populations of mature NKT cells potentially found in bone marrow, lymph node tissue and cord blood, thymus tissue.

In certain embodiments of the present invention, an isolated or enriched population or subpopulation of T, NK, NKT cells can be obtained from a unit of blood using any number of techniques known to the skilled artisan, such as Ficoll™ separation. In one embodiment, T, NK or NKT cells from the circulating blood of an individual are obtained by apheresis. The apheresis product typically contains cells, including T cells, monocytes, granulocytes, B cells, NK cells, NKT cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, Ca-free, Mg-free PBS, PlasmaLyte A, or other saline solution with or without buffer. Alternatively, the undesirable components of the apheresis sample can be removed and the cells directly resuspended in culture media.

In another embodiment, the population or subpopulation of T, NK or NKT cells are isolated or enriched from peripheral blood lymphocytes by lysing the red blood cells and depleting the monocytes, for example, by centrifugation through a PERCOLL™ gradient or by counterflow centrifugal elutriation.

In one embodiment, a specific subpopulation of T cells, can be further isolated or enriched by positive or negative selection techniques such as CD3, CD28, CD4, CD8, CD45RA, CD45RO, CD62L, CCR7, CD27, and/or CD122 antibodies. For example, in one embodiment, the isolated or enriched population or subpopulation of T cells are expanded and activated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 72 hours or longer and all integer values between. In a further embodiment, the time period is at least 1, 2, 3, 4, 5, or 6 hours. In yet another preferred embodiment, the time period is 10 to 72 hours. In one preferred embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), specific populations or subpopulations of T cells can be further selected for or against at culture initiation or at other time points during the process. Additionally, by increasing or decreasing the ratio of anti-CD3 and/or anti-CD28 antibodies on the beads or other surface, specific populations or subpopulations of T cells can be preferentially selected for or against at culture initiation or at other desired time points. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Isolation or enrichment of a population or subpopulation of T, NK or NKT cells by negative selection can be accomplished with a combination of antibodies directed to surface markers unique to the negatively selected cells. One method is cell sorting and/or selection via negative magnetic immuno-adherence or fluorescence-activated cell sorting that uses a cocktail of monoclonal antibodies directed to cell surface markers present on the cells negatively selected. For example, to enrich for CD3+ cells by negative selection, a monoclonal antibody cocktail typically includes antibodies to CD14, CD20, CD11b, CD16, and HLA-DR. In certain embodiments, it can be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection. In some embodiments, a desired T cell subpopulation for immunotherapy is enriched or selected from the modulated immune cells comprising T cells by CCR7 and CD62L. Alternatively cells of interest may be selected according to physical parameters including differential size, density, granularity, deformability, resistance or capacitance.

In one embodiment, a population or subpopulation of adaptive NK cells are enriched by selecting within the modulated immune cells comprising NK cells for those phenotypically CD3– and CD56+, using the identifiers such as include positive expression of CD16, NKG2C, and CD57. Further, negative selection of adaptive subpopulation can be based on lack of expression of NKG2C and/or CD57, and additionally lack expression of one or more of the following: low PLZF, low SYK, low FcεRγ, low EAT-2, low TIGIT, low PD1, low CD7, low CD161, high LILRB1, high CD45RO, and low CD45RA.

In one embodiment, a population or subpopulation of NKT cells are enriched by selecting within the population of NK cells for those phenotypically expressing the invariant TCRα chain, and specifically the following combination of markers: CD3+, CD56+, TCR Vα24+, and/or TCR Vo11+. Alternatively, NKT cells can be selected based on a combination of phenotype combined with expression of the invariant TCRα chain.

The blood samples or apheresis product from a subject can be collected at a time period prior to when the immune cells as described herein are isolated. As such, the source of the cells to be modulated can be collected at any time point necessary, and desired cells, such as T cells, NK cells and NKT cells, isolated and frozen for later use in cell-based immunotherapy for any number of diseases or conditions that would benefit from such cell therapy, such as those described herein. In one embodiment a blood sample or an apheresis product is collected from a generally healthy subject. In certain embodiments, a blood or an apheresis product is collected from a generally healthy subject who is at risk of developing a disease, but who has not yet developed a disease, and the cells of interest are isolated and frozen for later use. In other embodiments, a blood sample or an apheresis product is collected from a subject who has been previously administered with genetically modified immune cells (genetically engineered or naturally derived from rearrangements, mutations, genetic imprinting and/or epigenetic modification). In certain embodiments, the T, NK, NKT or other immune cells can be expanded, frozen, and treated and used at a later time. In certain embodiments, samples are collected from a patient shortly after diagnosis of a particular disease as described herein but prior to any treatments. In some embodiments, the cells are isolated from a subject presenting CMV (cytomegalovirus) seropositivity. In a further embodiment, the cells are isolated from a blood or an apheresis product from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, mycophenolic acid, steroids, FR901228, and irradiation. In a further embodiment, the cells are isolated from a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, the population or subpopulation of T, NK or NKT cells are genomically engineered, which include insertion, deletion, or nucleic acid replacement. Modified immune cells may express cytokine transgenes, silenced inhibitory receptors; or overexpress activating receptors, or CARs for retargeting the immune cells. In some embodiments, the population of immune cells isolated for modulation from a subject, or donor, or isolated from or comprised in peripheral blood, bone marrow, lymph node tissue, cord blood, thymus tissue, tissue from a site of infection, ascites, pleural effusion, spleen tissue, tumors of a subject/donor may be genetically modified. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof.

The genomically engineered immune cells comprise genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In some embodiments, the T, NK or NKT cells comprise an exogenous nucleic acid. In some embodiments, the exogenous nucleic acid is introduced to the immune cells via direct genomic editing of the cells. In some other embodiments, the exogenous nucleic acid is introduced to the immune cells via retaining the same from a genomically engineered hematopoietic stem or progenitor cell or iPSC, which gives rise to the immune cell through differentiation. In some embodiments, the exogenous nucleic acid for a T cell can encode a TCR (T Cell Receptor), a CAR (Chimeric Antigen Receptor), a bi-specific T cell engager (BiTE), a tri-specific T cell engager, a multi-specific T cell engager, or a universal engager compatible with multiple immune cell types. In some embodiments, the exogenous nucleic acid for a NK cell can encode a TCR, a CAR, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid for a NKT cell can be an altered TCR or CAR. In some embodiments, the exogenous nucleic acid encoding CAR19. In some embodiments, CD16 variants comprise high-affinity CD16 (HACD16), non-cleavable CD16, and high-affinity non-cleavable CD16 (hnCD16).

In some embodiments, the population or subpopulation of immune cells for modulation is differentiated in vitro from a stem cell or progenitor cell. In some embodiments, the isolated population or subpopulation of T, NK or NKT cells can be differentiated from a stem cell, a hematopoietic stem or progenitor cell (HSC), or a progenitor cell. The progenitor cell can be a CD34+ hemogenic endothelium cell, a multipotent progenitor cell, a T cell progenitor, a NK cell progenitor, or a NKT cell progenitor. The stem cell can be a pluripotent stem cell, such as induced pluripotent stem cells (iPSCs) and embryonic stem cells (ESCs). The iPSC is a non-naturally occurring reprogrammed pluripotent cell. Once the cells of a subject have been reprogrammed to a pluripotent state, the cells can then be programmed or differentiated to a desired cell type or subtypes, such as T, NK, or NKT cells.

In some embodiments, the iPSC is differentiated to a T, NK or NKT cells by a multi-stage differentiation platform wherein cells from various stages of development can be induced to assume a hematopoietic phenotype, ranging from mesodermal stem cells, to fully differentiated T, NK or NKT cells (See e.g. U.S. Applications 62/107,517 and 62/251,016, the disclosures of which are incorporated herein in their entireties). In some embodiments, the iPSC, HSC, or progenitor for T, NK or NKT cell differentiation is genomically engineered, which include insertion, deletion, or nucleic acid replacement.

In some embodiments, the genomically engineered iPSC, HSC or hematopoietic progenitor cells comprise genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSC, HSC, progenitor, or their derived cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, surface triggering receptors for coupling with bi- or multi-specific or universal engagers, a TCR (T Cell Receptor), or a CAR (Chimeric Antigen Receptor). In some embodiments, the iPSC, HSC, or progenitor for T, NK or NKT cell differentiation comprises modified HLA class I and/or II. In some embodiments, the iPSC, HSC, or progenitor for T, NK or NKT cell differentiation with modified HLA class I and/or II comprises null or low expression of at least one of B2M, HLA-E/G, PDL1, A2AR, CD47, LAG3, TIM3, TAP1, TAP2, Tapasin, NLRC5, PD1, RFKANK, CIITA, RFX5, and RFXAP. In some embodiments, the iPSC, HSC, or progenitor for T, NK or NKT cell differentiation has an exogenous nucleic acid. In some embodiments, the exogenous nucleic acid can encode, a bi-specific T cell engager (BiTE), a tri-specific T cell engager, a multi-specific T cell engager, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid encoding hnCD16 in the iPSC, HSC, or progenitor for T, NK or NKT cell differentiation. In some embodiments, the exogenous nucleic acid encoding CAR19 in the iPSC, HSC, or progenitor for T, NK or NKT cell differentiation.

In some embodiments, the population or subpopulation of immune cells is trans-differentiated in vitro from a non-pluripotent cell of non-hematopoietic fate to a hematopoietic lineage cell or from a non-pluripotent cell of a first hematopoietic cell type to a different hematopoietic cell type, which can be a T, NK, or NKT progenitor cell or a fully differentiated specific type of immune cell, such as T, NK, or NKT cell (See e.g. U.S. Pat. No. 9,376,664 and U.S. application Ser. No. 15/072,769, the disclosure of which is incorporated herein in their entirety). In some embodiments, the non-pluripotent cell of non-hematopoietic fate is somatic cells, such as skin fibroblasts, adipose tissue-derived cells and human umbilical vein endothelial cells (HUVEC). Somatic cells useful for trans-differentiation may be immortalized somatic cells.

Various strategies are being pursued to induce pluripotency, or increase potency, in cells (Takahashi, K., and Yamanaka, S., Cell 126, 663-676 (2006); Takahashi et al., Cell 131, 861-872 (2007); Yu et al., Science 318, 1917-1920 (2007); Zhou et al., Cell Stem Cell 4, 381-384 (2009); Kim et al., Cell Stem Cell 4, 472-476 (2009); Yamanaka et al., 2009; Saha, K., Jaenisch, R., Cell Stem Cell 5, 584-595 (2009)), and improve the efficiency of reprogramming (Shi et al., Cell Stem Cell 2, 525-528 (2008a); Shi et al., Cell Stem Cell 3, 568-574 (2008b); Huangfu et al., Nat Biotechnol 26, 795-797 (2008a); Huangfu et al., Nat Biotechnol 26, 1269-1275 (2008b); Silva et al., Plos Bio 6, e253. Doi: 10.1371/journal. Pbio. 0060253 (2008); Lyssiotis et al., PNAS 106, 8912-8917 (2009); Ichida et al., Cell Stem Cell 5, 491-503 (2009); Maherali, N., Hochedlinger, K., Curr Biol 19, 1718-1723 (2009b); Esteban et al., Cell Stem Cell 6, 71-79 (2010); and Feng et al., Cell Stem Cell 4, 301-312 (2009)), the disclosures of which are hereby incorporated by reference in their entireties.

III. Method of Modulating Immune Cells for Adoptive Therapies

The present invention provides a method of modulating a population or a subpopulation of immune cells suitable for adoptive cell-based therapies, and the method comprises contacting the immune cells with a composition comprising at least one agent selected from Table 1.

In one embodiment, the method of modulating a population or a subpopulation of immune cells suitable for adoptive cell-based therapies comprises contacting the immune cells with a composition comprising at least one agent selected from Table 1 wherein the contacted immune cells have increased cell expansion, increased number or ratio of one or more desired cell subpopulations, and/or improved proliferation, cytotoxicity, cell recall, and/or persistence in comparison to immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1, wherein the maintenance and expansion of one or more desired subpopulation of cells are improved in comparison to immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1, wherein the number or ratio of immune cells in the population reprogrammed to a desired state of differentiation is increased in comparison to immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1 in a sufficient amount for increasing cell expansion, increasing number or ratio of one or more desired immune cell subpopulations, and/or improving proliferation, cytotoxicity, cell recall, and/or persistence of the immune cell in comparison to immune cells without contacting the agents of Table 1. In one embodiment, the agent for immune cell treatment is between about 0.1 nM to about 50 µM. In one embodiment, the agent for immune cell treatment is about 0.1 nM, 0.5 nM, 1 nM, 5 nM, 10 nM, 50 nM, 100 nM, 500 nM, 1 µM, 5 µM, 10 µM, 20 µM, or 25 µM, or any concentration in-between. In one embodiment, the agent for immune cell treatment is between about 0.1 nM to about 5 nM, is between about 1 nM to about 100 nM, is between about 50 nM to about 250 nM, between about 100 nM to about 500 nM, between about 250 nM to about 1 µM, between about 500 nM to about 5 µM, between about 3 µM to about 10 µM, between about 5 µM to about 15 µM, between about 12 µM to about 20 µM, or between about 18 µM to about 25 µM.

In some embodiments, the method of modulating a population or a subpopulation of immune cells suitable for adoptive cell-based therapies comprises contacting the immune cells with a composition comprising at least one agent selected from Table 1 for a sufficient length of time for increasing cell expansion, increasing number or ratio of one or more desired immune cell subpopulations, and/or improving proliferation, cytotoxicity, cell recall, and/or persistence of the immune cell in comparison to immune cells without contacting the agents of Table 1. In one embodiment, the immune cells are contacted with one or more agent of Table 1 for at least 10 minutes, 30 minutes, 1 hours, 2, hours, 5 hours, 12 hours, 16 hours, 18 hours, 1 day, 2 days, 3 days, 4 days, 5 days, 6 days, 7 days, 10 days, 15 days, 20 days, 25 days, 30 days, or any length of period in between. In one embodiment, the immune cells are contacted with one or more agent of Table 1 for between about 0.5 hour to about 2 hours, between about 1 hour to about 12 hours, between about 10 hours to about 2 days, between about 1 day to about 3 days, between about 2 days to about 5 days, between about 3 days to about 6 days, between about 5 days to about 8 days, between about 7 days to about 14 days, between about 12 days to about 22 days, between about 14 days to about 25 days, between about 20 days to about 30 days. In some embodiments, the immune cells are contacted with one or more agent of Table 1 for no less than 16 hours, 14 hours, 12 hours, 10 hours, 8 hours, 6 hours, 4 hours, 2 hours, or any length of time in between. As such, said sufficient length of time, for example, is no less than 15, 13, 11, 9, 7, 5, 3, or 1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

The method of modulating a population or a subpopulation of immune cells suitable for adoptive cell-based therapies that comprises contacting the immune cells with a composition comprising at least one agent selected from Table 1, may further comprise enriching or isolating one or more desired subpopulations from the immune cells after the contacting, wherein the one or more desired subpopulations are selected from the group consisting of naïve T cell, stem cell memory T cell, central memory T cell, adaptive NK cell, and type I NKT cell.

In some embodiments, the subject is CMV seropositive, or may have been previously administered with genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient. In some embodiments, the donor derived immune cells for modulation comprise an exogenous nucleic acid encoding a T Cell Receptor (TCR) and/or a Chimeric Antigen Receptor (CAR).

Alternatively, the population of immune cells for modulation may be differentiated in vitro from stem cell, hematopoietic stem or progenitor cells, or progenitor cells; or trans-differentiated from a non-pluripotent cell of hematopoietic or non-hematopoietic lineage. In some embodiments, the stem cells, hematopoietic stem or progenitor cells, progenitor cells, or a non-pluripotent cell that derive the immune cells for modulation are genomic engineered and comprise an insertion, a deletion, and/or a nucleic acid replacement, as such the derived immune cells for modulation comprise the same genetic modalities introduced by genomic engineering in the source cells.

IV. Therapeutic Use of the Treated Immune Cells, Immune Cell Population or Subpopulations The present invention provides a composition comprising an isolated population or subpopulation of immune cells that have been contacted with one or more agents selected from Table 1 in an amount sufficient to improve the therapeutic potential of the immune cells when used in a cell based adoptive therapy. In one embodiment, the isolated population or subpopulation of immune cell that has been treated comprises an increased number or ratio of naïve T cells, stem cell memory T cells, and/or central memory T cells. In one embodiment, the isolated population or subpopulation of immune cell that has been contacted comprises an increased number or ratio of type I NKT cells. In another embodiment, the isolated population or subpopulation of immune cell that has been contacted comprises an increased number or ratio of adaptive NK cells. It is contemplated herein that combination treatments using NK cell therapy products together with other drugs that target tumor cells or modulate cytotoxic activity of NK cells. In some embodiments of the composition, the composition further comprises one or more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, antibodies, chemotherapeutic agents or radioactive moiety, and immunomodulatory drugs (IMiDs).

The present invention also provides compositions and methods of combinational treatment comprising the immune cells modulated with one or more agents comprising the compounds listed in Table 1, and additional therapeutic agents. In some embodiments, the additional therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the modulated NK cells to make use of antibody-dependent cellular cytotoxicity (ADCC) and lysis of the target cell. Monoclonal antibodies (mAbs) bind to the target cell plus engaging CD16 on NK cells and other cell types resulting in killing of tumor cell by ADCC both in vivo and in vitro. mAbs can also enhance ADCC and stimulate NK cells by blocking NK cell inhibition. In some embodiments, the NK cell mediated ADCC is through expressed CD16 and genetically engineered variants thereof by the modulated NK cells. The genetically engineered variants of CD16 include, but are not limited to, non-cleavable CD16, high affinity CD16 (haCD16), and high affinity non-cleavable CD16 (hnCD16). As such, the above aspect of the present invention provides GSK3i modulated NK cells capable of performing ADCC in antibody combination cancer treatments. In some embodiments, the antibodies suitable for combinational treatment with anti-cancer NK cells provided herein include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab), and their humanized and Fc modified variants. Additionally, the design of bi- and trispecific antibodies, fusing the Fab region of the antibody targeting the tumor cell antigen, such as the anti-CD19, CD20, and CD33 antigens, in combination with another Fab region recognizing CD16 on NK cell leads to stimulation of the NK cells followed by tumor cell killing.

In some embodiments, the additional therapeutic agent comprises one or more chemotherapeutic agents or a radioactive moiety. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's *The Pharmacological Basis of Therapeutics*, Ninth Edition, McGraw-Hill, N.Y, 1995) or through the National Cancer Institute website (fda.gov/cder/cancer/druglistfrarne.htm), both as updated from time to time.

Immunomodulatory drugs (IMiDs) such as thalidomide, lenalidomide, and pomalidomide stimulate both NK cells and T cells. As provided herein, IMiDs may be used with the modulated therapeutic immune cells for cancer treatments.

A variety of diseases may be ameliorated by introducing the cells of the invention to a subject suitable for adoptive cell therapy. Examples of diseases including various autoimmune disorders, including but not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's); hematological malignancies, including but not limited to, acute and chronic leukemias, lymphomas, multiple myeloma and myelodysplastic syndromes; solid tumors, including but not limited to, tumor of the brain, prostate, breast, lung, colon, uterus, skin, liver, bone, pancreas, ovary, testes, bladder, kidney, head, neck, stomach, cervix, rectum, larynx, or esophagus; and infections, including but not limited to, HIV—(human immunodeficiency virus), RSV—(Respiratory Syncytial Virus), EBV—(Epstein-Barr virus), CMV—(cytomegalovirus), adenovirus- and BK polyomavirus-associated disorders.

EXAMPLES

The following examples are offered by way of illustration and not by way of limitation.

Example 1—Methods and Materials

In Vitro T Cell Culture. Fresh leukopaks (AllCells, Alameda, CA) were obtained from healthy donors, from which T cells were negatively selected using the EasySep Human T Cell Enrichment Kit (Stem Cell Technologies, Vancouver, Canada). The freshly isolated T cells were aliquoted and cryopreserved. On the day the screens were initiated, T cells were thawed and washed into X-Vivo 15 with 5% human AB serum, IL-2, pen/strep, and additional supplements. Cells were dispensed into flat-bottom 384-well plates at $5 \times 10^5$ cells/ml with anti-CD3/Anti-CD28 dynabeads (ThermoFisher, Waltham, MA) at a 3:1 bead-to-cell ratio. Individual compounds were added at a final concentration of 10 µM to each well from column 3 to column 22 of each plate. Positive and negative controls were added to additional wells. Cells were incubated for about 6 days at 37 degrees with 5% CO2.

Flow Cytometry. On Day 6 of culture, cells were stained with a fixable viability marker and fluorophore-conjugated antibodies: CD3, CD4, CD8, CD45RA, CD45RO, CD62L, CCR7, CD27, and CD122 (BD Biosciences, San Jose, CA; and BioLegend, San Diego, CA). Fluorescent absolute counting beads (Spherotech, Lake Forest, IL) were added just prior to acquisition. Data acquisition was performed on a BD Fortessa X-20 (BD Biosciences) and data were analyzed using Treestar software (FlowJo, Ashland, OR) and Spotfire (Tibco, Boston, MA).

Culturing cells in large-scale for phenotypic and exhaustion marker evaluation. Isolated CD8 T cells were activated in bulk on day 0 using CTS (Cell Therapy Systems) Dynabeads™ CD3/CD28 (Thermo Fisher Scientific, Waltham, MA) in T cell media supplemented with IL-2. On day 1, cells were transduced with the CAR Construct and cell density was adjusted to $0.5 \times 10^6$/ml and $10^6$ cells were seeded into 12-well plates in the presence of vehicle, TWS119, or DCC-2036. On day 4, cells were transferred into 6-well plates and 2 ml of T cell media was added to each well. On day 6 another 2 ml of media was added to each well. On day 8, CAR T cells were analyzed on a flow cytometer for surface expression of phenotypic markers (CD62L, CCR7, and CD27) and exhaustion markers (PD-1 and Tim-3).

Example 2—Agent for Immune Cell Modulation

Data were analyzed to identify compounds that either produced a higher proportion or greater absolute number of phenotypically identified naïve, stem cell memory, or central memory T cells. These cells are characterized by expression of CCR7 and CD62L. Therefore, cells co-expressing both of these identifying markers were evaluated. Within the viable CD4+ population and viable CD8+ population, the percent of cells co-expressing CCR7 and CD62L was determined. The expression of either CD62L or CCR7 on T cells, as indicative of the desired T cell subsets, have been described as having favorable functional characteristics for CAR-T cell therapy, and potentially other adoptive T cell therapies. Under the treatment of dorsomorphin, heptelidic acid, GSK3 inhibitor, 6-Mercaptopurine, AC-93253 iodide, tiratricol, PI-103, 5-Azacytidine, 5,7-dichloro-8-Quinolinol, Nitrofurantoin, 5-chloro-7-iodo-8-Quinolinol, or diethylenetriaminepentaacetic acid, the number or ratio of cells co-expressing CCR7 and CD62L increased in both viable CD4+ population and viable CD8+ population (Table 2). Under the treatment of fulvestrant, thapsigargin, SU 4312, fludarabine, 2-Naphthacenecarboxamide, 7-chloro-4-(dimethylamino)-1,4,4a,5,5a,6,11,12a-octahy, nifuroxazide, edrophonium chloride, the number or ratio of cells co-expressing CCR7 and CD62L increased at least in viable CD8+ population (Table 2). Under the treatment of 1-Pyrrolidinecarbodithioic acid, ammonium salt, U0126, telmisartan, cyclosporin A, 1,3,5-tris(4-hydroxyphenyl)-4-propyl-1H-pyrazole, BAY 61-3606, Protoporphyrin IX disodium, rapamycin, roscovitine, PAC-1, tosufloxacin hydrochloride, BIX01294, and terfenadine, the number or ratio of cells co-expressing CCR7 and CD62L increased at least in viable CD8+ population (Table 2).

In addition, GSK3 (Glycogen synthase kinase 3) inhibitor was shown to preserve CD3-CD19-CD56+NK cells, and increased the adaptive NK cell subpopulation by affecting cell maturation and subtype skewing, based on observation of including, but not limited to CD57+ and NKG2C+ expression.

The number of events in each of these gates relative to the number of absolute counting beads in each sample was calculated, defining a relative measure of the absolute number of naïve, stem cell memory, or central memory T cells within the CD4+ and/or CD8+ populations. A z-Score relative to the screened compound samples within each 384-well plate was calculated for each of these four values: 1) percent CCR7+CD62L+ in CD4+, 2) percent CCR7+CD62L+ in CD8+, 3) absolute relative number of CCR7+CD62L+ in CD4+, and 4) absolute relative number of CCR7+CD62L+ in CD8+(FIGS. 1A and 1i). Z-scores were also calculated for the percent viability of all cells within each sample and the relative absolute number of cells within each sample. A "Z-Score" is a statistical measurement of a score's relationship to the mean in a group of scores. A Z-score of 0 means the score is the same as the mean. A Z-score can also be positive or negative, indicating whether it is above or below the mean and by how many standard deviations.

Eliminating compounds that have a detrimental impact on T cell proliferation or viability, focuses efforts on compounds that are most likely to be amenable to T cell manufacturing strategies. Primary hit compounds were selected by the following criteria: 'percent viability' Z-score of greater than −1, 'relative absolute number of cells' Z-score of greater than −1, and Z-score of one of the 4 values of greater than +2. 34 compounds (Table 2) were selected for having much higher Z-Scores and meeting the above criteria for more than 1 of the 4 primary values. An additional 5 compounds are also included for their abilities to modulate T cells (Table 3)

TABLE 2

Agents for T Cell Modulation in Adoptive Cell Therapies

| Compounds | CAS Number | Compound Information | Group | Group Descriptor | CD8 Hit | CD4 Hit |
|---|---|---|---|---|---|---|
| Dorsomorphin | 866405-64-3 | AMPK inhibitor | I | Metabolism & Nutrient Sensing | CD8 | CD4 |
| Heptelidic acid | 74310-84-2 | GAPDH inhibitor | I | Metabolism & Nutrient Sensing | CD8 | CD4 |
| 1-Pyrrolidinecarbodithioic acid, ammonium salt | 5108-96-3 | Prevents induction of nitric oxide synthetase | I | Metabolism & Nutrient Sensing | | CD4 |
| GSK3 Inhibitor | For example-BIO; 667463-62-9 | GSK-3α/β inhibitor | II | Signaling Pathways | CD8 | CD4 |
| 6-Mercaptopurine | 6112-76-1 | Competes with purine derivatives hypoxanthine and guanine for enzyme HGPRT | II | Signaling Pathways | CD8 | CD4 |
| AC-93253 iodide | 108527-83-9 | Subtype selective RAR (RARα) agonist | II | Signaling Pathways | CD8 | CD4 |
| Tiratricol | 51-24-1 | Thyroid hormone analogue | II | Signaling Pathways | CD8 | CD4 |
| PI-103 | 371935-74-9 | mTOR/PI3K inhibitor | II | Signaling Pathways | CD8 | CD4 |
| Fulvestrant | 129453-61-8 | Estrogen receptor antagonist | II | Signaling Pathways | CD8 | |
| Thapsigargin | 67526-95-8 | sarco/ER Ca2+-ATPase antagonist | II | Signaling Pathways | CD8 | |
| SU 4312 | 5812-07-7 | VEGF receptor protein tyrosine kinase 1/2 and PDGF receptor inhibitor | II | Signaling Pathways | CD8 | |
| U0126 | 109511-58-2 | MAPK/ERK kinase; antagonizes AP-1 transcriptional activity | II | Signaling Pathways | | CD4 |
| Telmisartan | 144701-48-4 | Micardis; angiotensin II receptor anatagonist | II | Signaling Pathways | | CD4 |
| Cyclosporin A | 59865-13-3 | Neoral; immunosuppressive | II | Signaling Pathways | | CD4 |
| 1,3,5-tris(4-hydroxyphenyl)-4-propyl-1H-pyrazole | 263717-53-9 | PPT; a specific estrogen receptor α (ERα) agonist | II | Signaling Pathways | | CD4 |
| BAY 61-3606 | 732983-37-8 | Spleen tyrosine kinase (Syk) inhibitor | II | Signaling Pathways | | CD4 |
| Protoporphyrin IX disodium | 553-12-8 | GCS (guanylate cyclase) activator | II | Signaling Pathways | | CD4 |
| rapamycin | 53123-88-9 | Sirolimus; immunosuppressant | II | Signaling Pathways | | CD4 |
| 5-Azacytidine | 320-67-2 | Cytosine nucleoside analog that interferes with nucleic acid synthesis | III | Proliferation and Apoptosis | CD8 | CD4 |
| Fludarabine | 21679-14-1 | Purine analog that interferes with nucleic acid synthesis | III | Proliferation and Apoptosis | CD8 | |
| Roscovitine, (S)-Isomer | 186692-45-5 | Cyclin-dependent kinase (Cdk) inhibitor | III | Proliferation and Apoptosis | | CD4 |
| PAC-1 | 315183-21-2 | Procaspase-3 activating compound; | III | Proliferation and Apoptosis | | CD4 |
| 8-Quinolinol,5,7-dichloro- | 773-76-2 | Capitrol; Antibiotic | IV | Anti-infective | CD8 | CD4 |
| Nitrofurantoin | 67-20-9 | Antibiotic | IV | Anti-infective | CD8 | CD4 |
| 8-Quinolinol,5-chloro-7-iodo- | 130-26-7 | Clioquinol; Antibiotic | IV | Anti-infective | CD8 | CD4 |
| 2-Naphthacenecarboxamide, 7-chloro-4-dimethylamino)-1,4,4a,5,5a,6,11,12a-octahy | 64-73-3 | Ribosomal protein synthesis inhibitor | IV | Anti-infective | CD8 | |
| Nifuroxazide | 965-52-6 | Nitrofuran antibiotic | IV | Anti-infective | CD8 | |
| Tosufloxacin hydrochloride | 100490-36-6 | Ozex; Fluoroquinolone antibiotic | IV | Anti-infective | | CD4 |
| Sertraline | 79617-96-2 | Zoloft; antidepressant | V | Other | CD8 | CD4 |
| Diethylenetriaminepentaacetic acid, penta sodium | 67-43-6 | Iron chelating agent | V | Other | CD8 | CD4 |
| Edrophonium chloride | 116-38-1 | Reversible acetylcholinesterase inhibitor | V | Other | CD8 | |
| BIX01294 | 1392399-03-9 | GLP and G9a histonelysine methyltransferase inhibitor | V | Other | | CD4 |
| Terfenadine | 50679-08-8 | Antihistamine | V | Other | | CD4 |
| dmPGE2 | 39746-25-3 | Prostaglandin molecule | V | Other | | |

TABLE 3

Additional Agents for T Cell Modulation
in Adoptive Cell Therapies

| Compounds | CAS Number | Compound Information | Group | Group Descriptor |
|---|---|---|---|---|
| 2-DG | 154-17-6 | Inhibits glycolysis | I | Metabolism & Nutrient Sensing |
| GSK3 Inhibitor | For example- TWS119: 601514-19-6 | GSK3 inhibitor | II | Signaling Pathways |
| HS173 | 1276110-06-5 | PI3K inhibitor | II | Signaling Pathways |
| LY294002 | 154447-36-6 | PI3K inhibitor | II | Signaling Pathways |
| Pictilisib | 957054-30-7 | PI3K inhibitor | II | Signaling Pathways |

Example 3—In Vitro Triage Experiments of the Selected Compounds

In vitro experiments are performed to optimize methods for compound exposure and triage compounds that have detrimental impacts on T cell functions. Initial tests determine optimal dose of individual compounds while also evaluating whether the impact on naïve, stem cell memory, and central memory T cells observed previously are replicated in additional donors. To triage compounds with potential detrimental functional impacts on T cells, in vitro assessments for proliferative capacity, ability to polarize to Th1 and Th17, survival through a cryopreservation/thaw cycle, transduction efficiency, and tumoricidal activity of CAR-transduced T cells are performed. Compounds that reproducibly improve ratio or number of naïve, stem cell memory, or central memory T cells during expansion without significant negative impacts on T cell function are tested in combination and assessed for additive or synergistic effects. Through these assessments, lead candidates or combinations are prioritized for additional testing in vivo.

Example 4—In Vivo Models of Adoptive Cellular Therapy Using the Selected Compounds To translate the results of the in vitro screening and follow up in vitro triage experiments the lead candidates of the selected compounds are applied to in vivo models of adoptive cellular therapy. Specifically, the impact of small molecule modulation is interrogated on adoptive cellular therapy in regards to engraftment, tumoricidal activity, secondary tumoricidal responses, migration, cellular persistence, and graft-versus-host disease. Other readouts which are hall marks of durable adoptive cellular therapy that have been found to correlate with efficacious responses in the clinic are also interrogated.

These experiments are conducted either in a humanized system, in which human cells are adoptively transferred into immuno-deficient NSG mice bearing human tumors, or in a surrogate murine model, in which an immuno-competent animal bears a syngeneic tumor and is treated with syngeneic cellular therapy.

In either the surrogate or humanized model system, mice are injected with a luciferized lymphoma or other tumor of interest. Soon thereafter, the adoptive cellular therapy which has been pre-treated with vehicle or modulating compounds disclosed herein is administered. Dose of both the cell therapy and tumor is optimized to enable a window in which positive or detrimental effects of the compound treatment can be observed. The animal weight, plasma cytokine concentrations, abundance of tumor and adoptive cellular therapy in peripheral blood, secondary lymphoid organs and tumor mass; tumor burden, tumor metastasis, and phenotype of the cellular therapy are monitored for the duration of the experiment.

Compounds that are able to ameliorate one or many tumor-related parameters in vivo have expected effects including, but not limited to, decreasing the cellular therapy dose required for effective tumor clearance, increasing the persistence of adoptive cellular therapy in the peripheral blood, enhancing migration to tumor sites, and/or increased survival against challenge with high tumor dose.

Example 5—Synergistic Increase in CD27 with Rapa+dmPGE2 Treatment in T Cells

CD27 is a member of the TRA-linked TNF (Tumor Necrosis Factor) receptor family that also includes 4-1BB and OX-40. These transmembrane proteins are involved in the regulation of lymphocyte function. In humans, most naïve peripheral T cells (Tn) express CD27. Once the naïve peripheral T cells are activated, the expression of CD27 is significantly increased. However, terminal effector differentiation of T cell is associated with irreversible loss of CD27 (Hintzen et al. 1994). Further elucidation of the role of CD27 demonstrated that it was required for the generation and long-term maintenance of T cell immunity (Hendriks et al. 2000).

Figure 2:
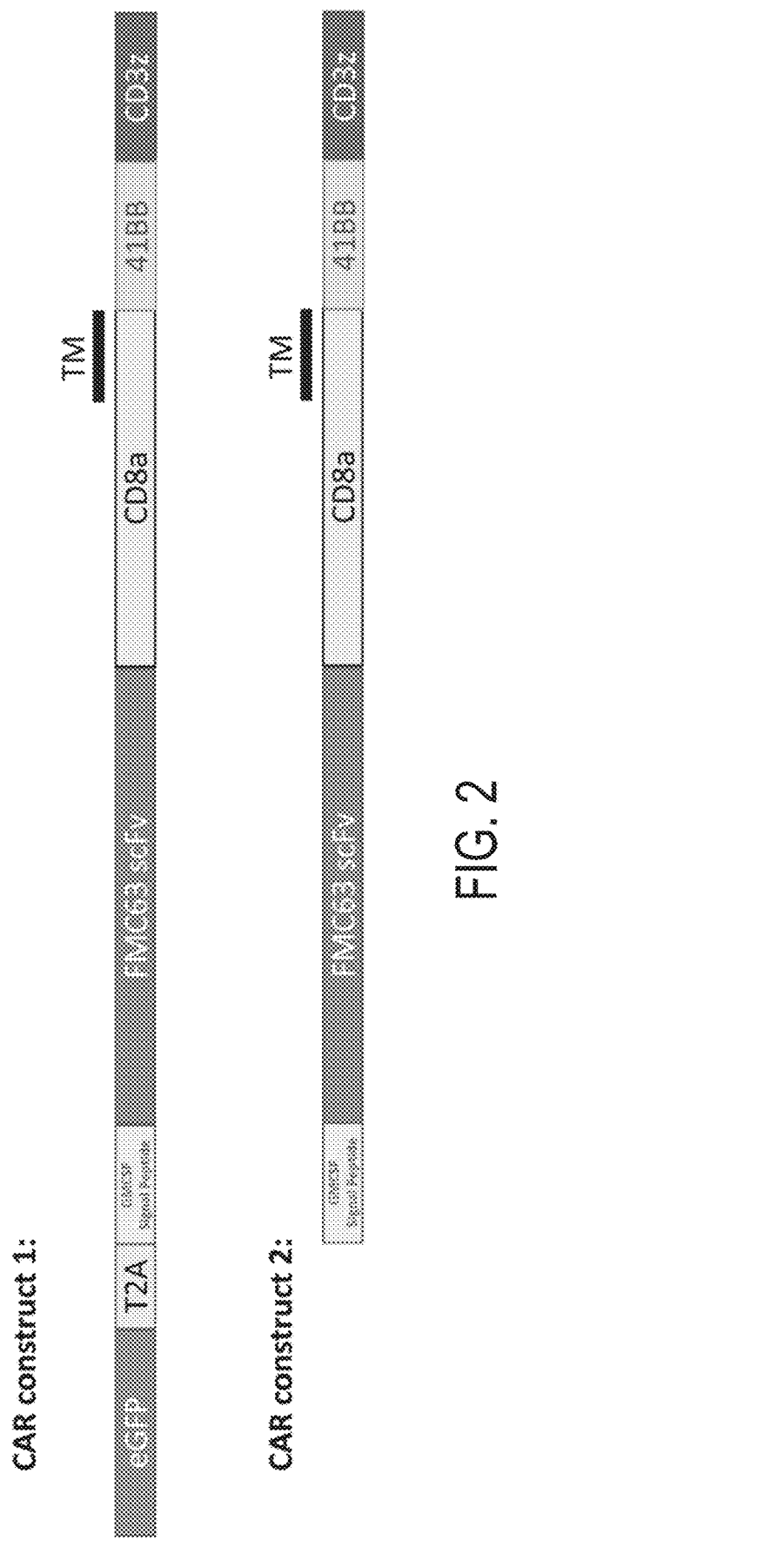
FIG. 2 shows the various CAR constructs used in the studies.

Cells treated with rapamycin (referred to as "rapa" from time to time), dimethyl prostaglandin E2 (dmPGE2) or a combination of both compounds exhibited significant differences in many aspects when compared to cells treated with vehicle alone (DMSO). However, one of the strongest changes observed was a synergistic increase in the level of CD27 expressed on the surface of CD8 T cells treated with rapa+dmPGE2 relative to the expression of CD27 on CD8 T cells treated with vehicle or either compound alone. In order to perform these studies, isolated CD8 T cells were activated in bulk on day 0 using CTS (Cell Therapy Systems) Dynabeads™ CD3/CD28 (Thermo Fisher Scientific, Waltham, MA) in T cell media supplemented with IL-2. On day 1, cells were transduced with the CAR Construct 1 shown in FIG. 2 and cell density was adjusted to $0.5 \times 10^6$/ml and $10^6$ cells were seeded into 12 well plates in the presence of vehicle, 20 nM rapa, 10 µM dmPGE2 or both compounds at the same concentrations. On day 4, cells were transferred into 6-well plates and 2 ml of media was added to each well. On day 6 another 2 ml of media was added to each well. On day 8, cells were analyzed on a flow cytometer for cell surface expression of CD27.

Figure 3:
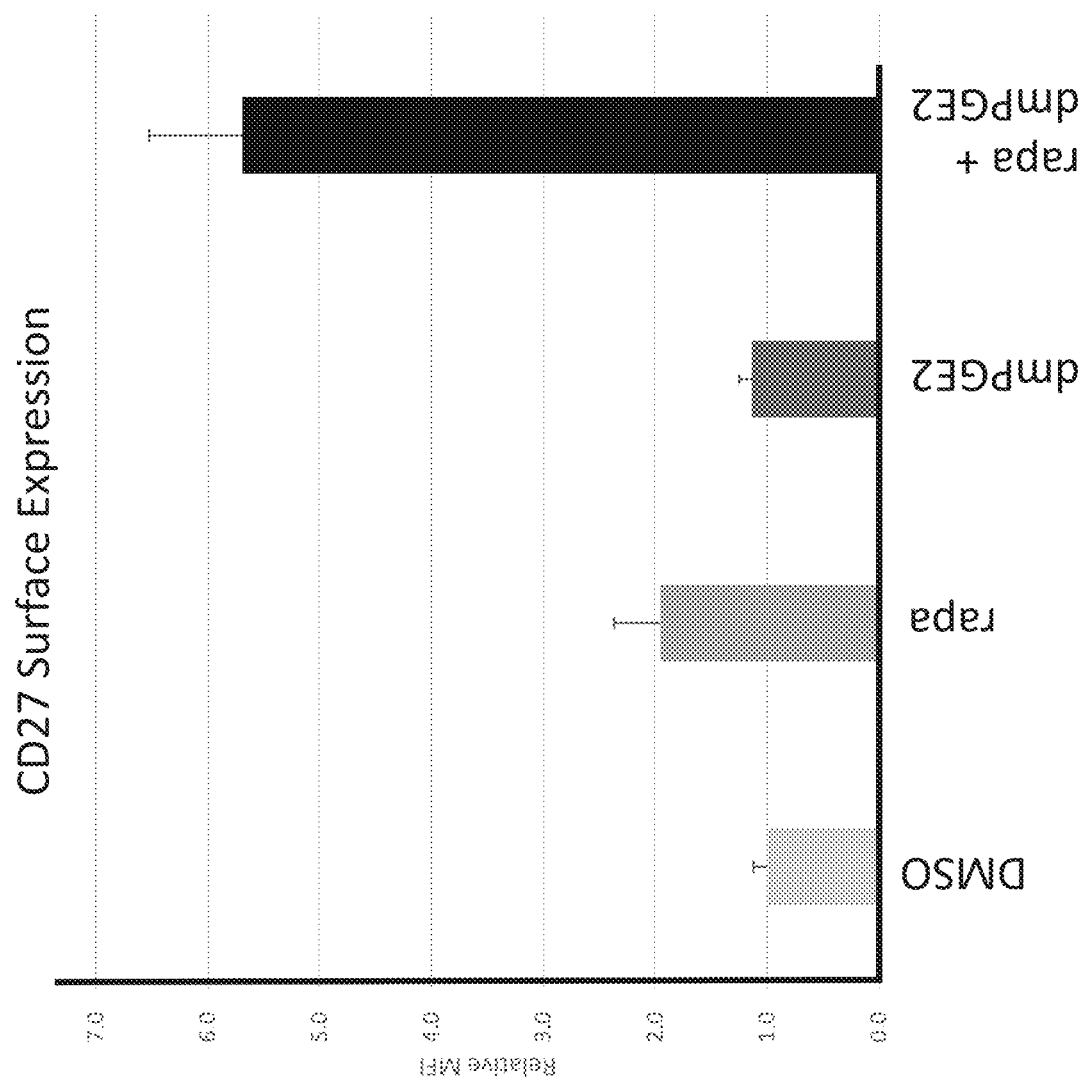
FIG. 3 shows CD27 surface expression on CAR-T cells treated under DMSO (vehicle), rapamycin, dmPGE2, and rapamycin+dmPGE2 combination, respectively.

The expression of CD27 in treated and untreated T cells from two independent donors is shown in FIG. 3. The expression of CD27 observed with vehicle treatment was defined as an MFI (mean fluorescence intensity) of 1 and the relative MFI of cells treated with compound was calculated. When CD8 T cells are incubated with rapa alone, the CD27 expression increases approximately 2-fold; with dmPGE2 alone there is no increase, i.e., dmPGE2 alone has no impact on the CD27 expression. However, when CD8 T cells are incubated in the presence of a combination of rapamycin and dmPGE2 (rapa+dmPGE2), the increase in CD27 expression relative to the vehicle is almost 6-fold, a level that cannot be explained simply through additive effects of the two individual compounds. Thus, it appears that the cell surface expression of CD27 induced by the compound combination is synergistic; and the compound combination appears to drive for the phenotype of naïve T cells rather than T effector cells.

Example 6—Rapa+dmPGE2 Treatment Increases the T Cell Central Memory Subset

Figure 4:
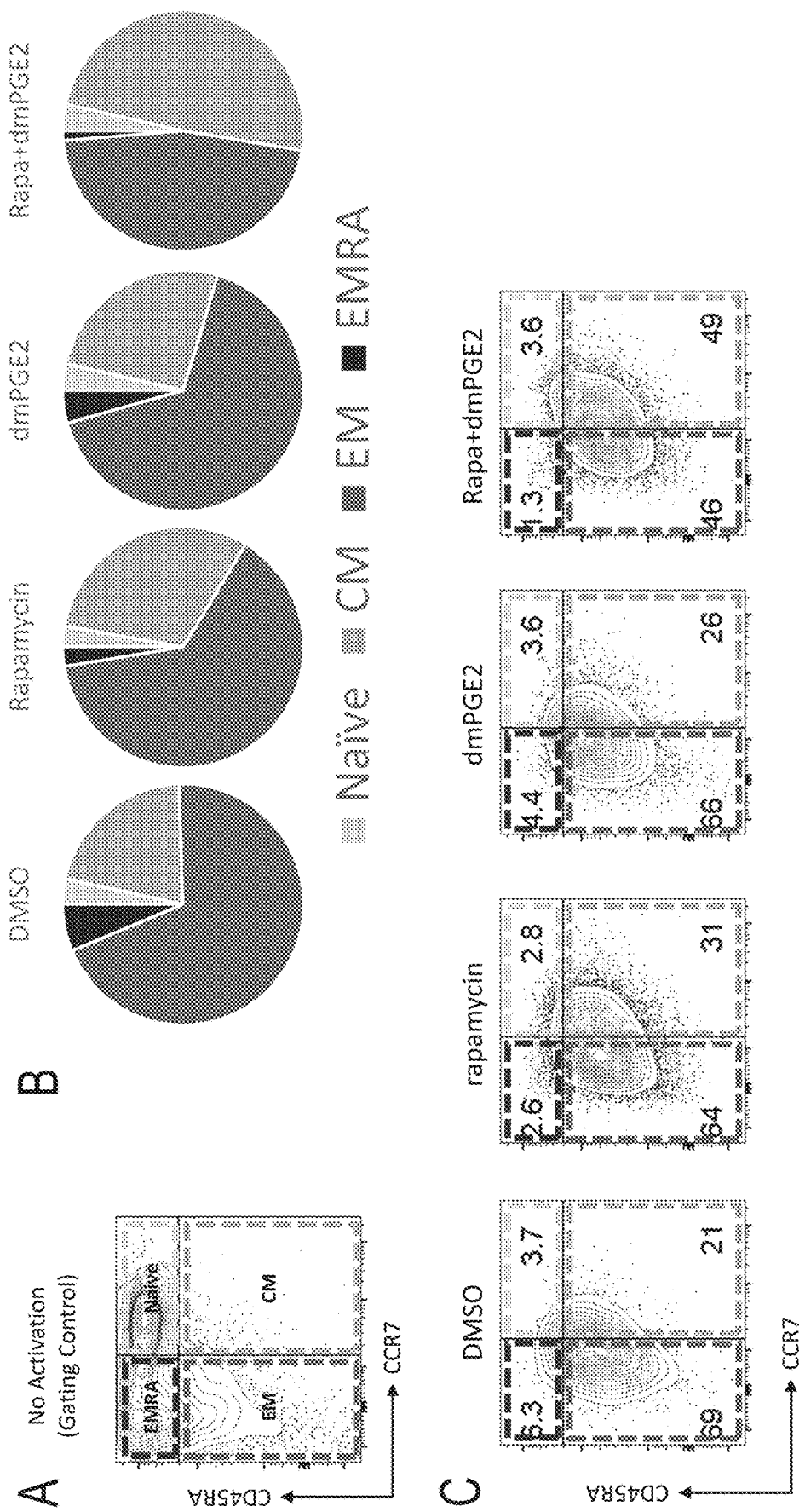
FIG. 4 shows CAR-T cells treated with rapamycin+dmPGE2 combination acquire a central memory phenotype. A: T cell subsets including central memory (Tcm), naïve (Tn), effector memory (Tem) and CD45RA+ effector memory (Temra) T cells. B: T cell subsets present in cultures after DMSO, rapamycin, dmPGE2, and rapamycin+dmPGE2 combination treatment. C: Flow cytometry analysis used to identify the different subsets under respective compound treatment.

Studies in both non-human primate and NOD/Scid IL-2RγC$^{null}$ (NSG) mouse models have demonstrated that T cells with a central memory (Tcm) phenotype have improved persistence after adoptive transfer (Berger et al. 2008; Wang et al. 2011). In addition, CAR-expressing CD4 and CD8 central memory T cell (Tcm) subsets were administered to Non-Hodgkin lymphoma patients after hematopoietic stem cell transplantation, and the Tcm-derived CAR-T cells demonstrated improved expansion, indicating that Tcm may have a therapeutic advantage in treatment of human cancers. The capability of the rapamycin and dmPGE2 combination in skewing the population toward a Tcm phenotype was accessed. The CD8 Tcm subset was defined based on the expression of the cell surface markers CD45RA and CCR7. FIG. 4A shows a scatter plot of the CD45RA and CCR7 expression in T cells that have not been activated, which was then used for gating of the T cell subsets including Tcm, naïve (Tn), effector memory (Tem) and CD45RA+ effector memory (Temra) cells. Tn and Tcm cells are the least differentiated and have the greatest proliferative potential while Temra cells are the most fully differentiated, have poor proliferative potential but strong effector function (D'Asaro et al. 2006).

CD8 T cells were treated with vehicle, rapa, dmPGE2 or rapa+dmPGE2 as described in Example 5. FIG. 4B shows a schematic representation of the T cells subsets present in cultures after respective treatment. FIG. 4C shows the flow cytometry analysis used to identify the different subsets. Relative to vehicle or either compound alone, there is an increase in the percentage of Tcm subset accompanied by a loss in the more differentiated Tem subset after treatment with the combination of rapamycin and dmPGE2. Thus, treatment with rapa+dmPGE2 causes an increase in a more desirable T cell subset (Tcm) for CAR-T cell therapy. Without being limited by theory, the phenotype shifting from Tem to Tcm, and/or the promoted Tcm expansion may have contributed to the increased percentage of Tcm in the modulated population.

Example 7—Rapa+dmPGE2 Treatment Reduces T Cell Exhaustion Marker Expression

Figure 5:
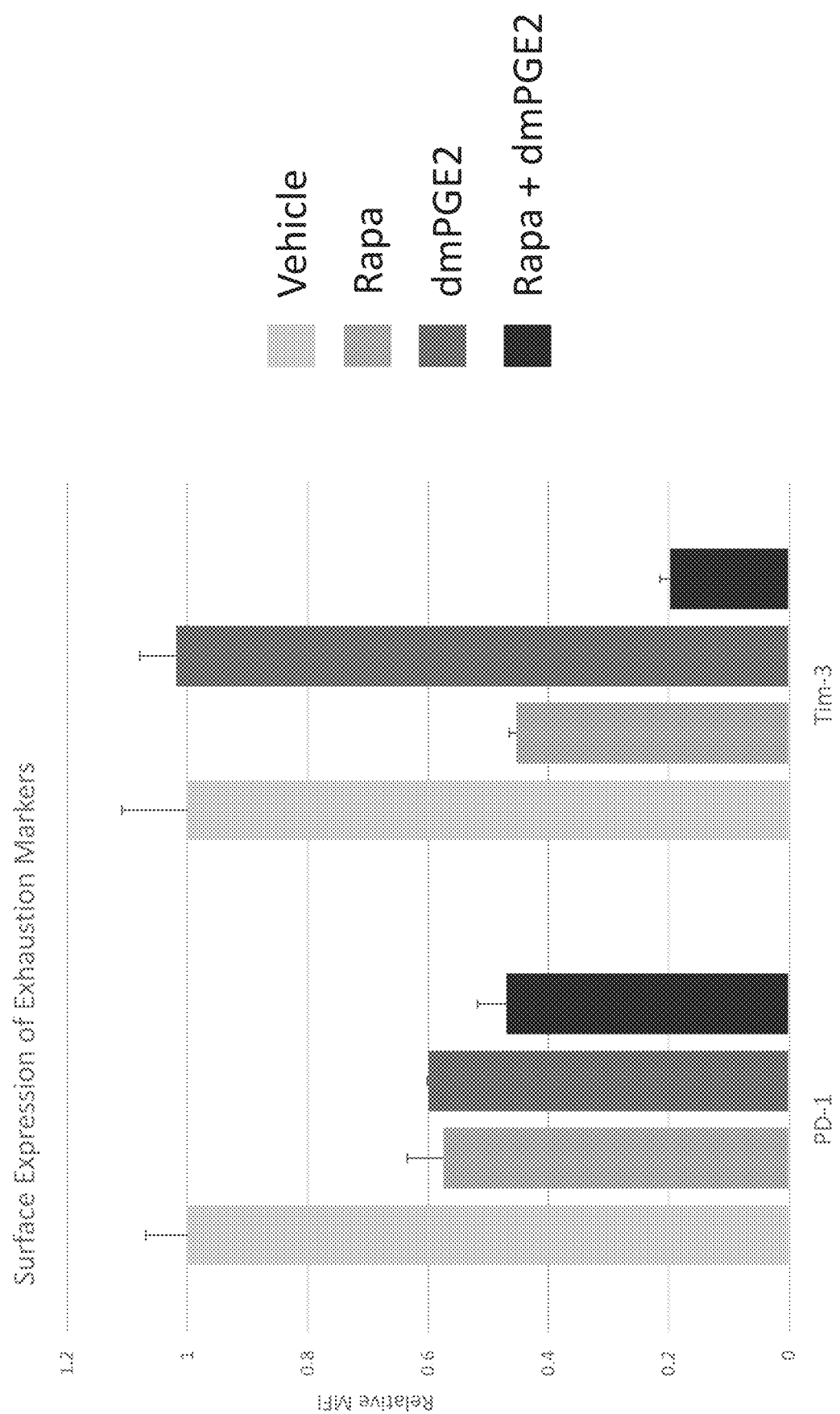
FIG. 5 shows the expression exhaustion markers, PD-1 and Tim-3, in CD8 CAR-T cells treated under DMSO, rapamycin, dmPGE2, and rapamycin+dmPGE2 combination.

T cell dysfunction due to 'exhaustion' is a state that can preclude adequate control of cancer or infection. T cell exhaustion is characterized by poor effector cell function and increased expression of multiple cell surface proteins, collectively known as exhaustion markers, including PD-1 and Tim-3 (Wherry and Kurachi 2015). To determine the effect of compound treatment of CAR-T cells on exhaustion marker expression, cells from two different donors were prepared and treated as described in Example 5 then stained for PD-1 and Tim-3 and expression was determined using flow cytometry. As shown in FIG. 5, treatment with either rapamycin or dmPGE2 decreased PD-1 expression while treatment with rapamycin and dmPGE2 combination led to a slightly greater reduction in PD-1 expression relative to vehicle, or each individual compound treatment. As to Tim-3 expression under various treatments, rapamycin alone decreased Tim-3 expression while dmPGE2 alone showed no effect when compared to vehicle. However, the combination of rapamycin and dmPGE2 reduced Tim-3 expression more markedly as compared to any single compound treatments or no treatment. An enhanced reduction in Tim-3 expression by rapa+dmPGE2 combination was observed relative to vehicle, rapamycin, and dmPGE2, despite the fact that, when used alone, dmPGE2 has no effect on Tim-3 expression. This data indicated that treating T cells with rapamycin and dmPGE2 combination enhances the cell's anti-tumor capability by reducing T cell exhaustion that contributes to immune dysfunction.

Example 8—Rapa+dmPGE2 Treatment Increases T Cell Mitochondrial Spare Respiratory Capacity Cells generally utilize two major energy pathways, glycolysis and mitochondrial respiration. It has been shown that mitochondrial spare respiratory capacity (SRC), which is the extra capacity available in cells to produce energy in response to increased stress or work, is increased in T memory cells but not in T effector cells, such as Temra (van der Windt et al. 2012).

Figure 6:
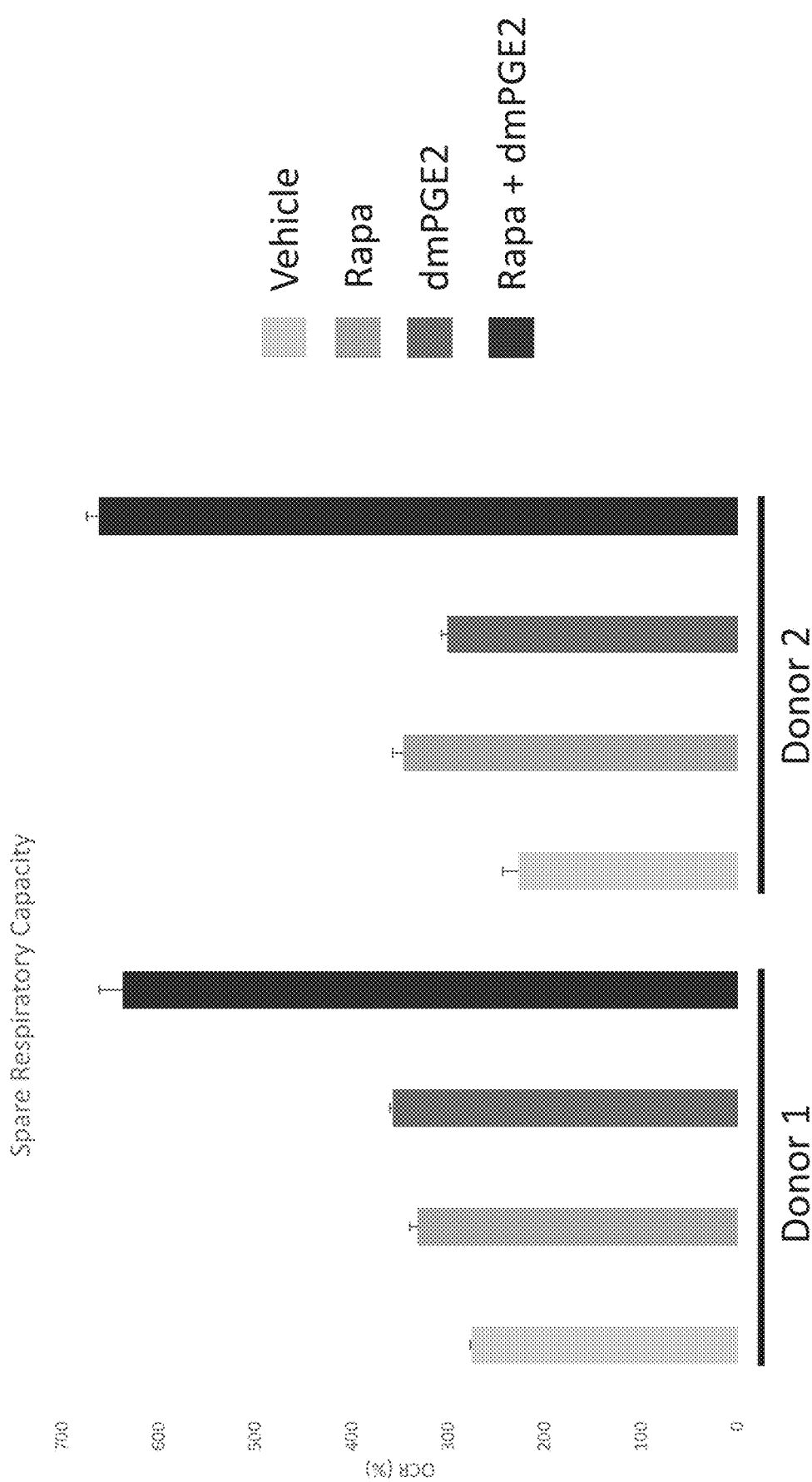
FIG. 6 shows oxygen consumption rate (OCR) in cells treated under DMSO, rapamycin, dmPGE2, and rapamycin+dmPGE2 combination.

We determined whether compound treatment had an effect on SRC using cells transduced and treated as described in Example 5. After treatment, oxygen consumption rate (OCR), a measure of mitochondrial respiration was determined using a Seahorse™ XFe96 system (Seahorse Bioscience, Santa Clara, CA). To do this, the cells were washed and resuspended in non-buffered assay medium. The cells were then seeded in 96-well assay plates, and subjected to the Seahorse™ mitostress test assay. SRC is determined based on the difference between basal OCR and OCR at the maximal respiration rate. FIG. 6 shows that SRC is increased almost two-fold in cells treated with rapa+dmPGE2, whereas treatment with each individual compound shows only a modest increase of about 20-50% relative to vehicle controls. These data indicate that CAR-T cells treated with rapa+dmPGE2 not only increase, or being skewed towards, Tcm phenotype, but also demonstrate the desired metabolic profile related to the memory T cell subset.

Example 9—Genome-Wide Expression Characterization of CD8+ T-Cells Treated with Rapa+dmPGE2

Figure 7A:
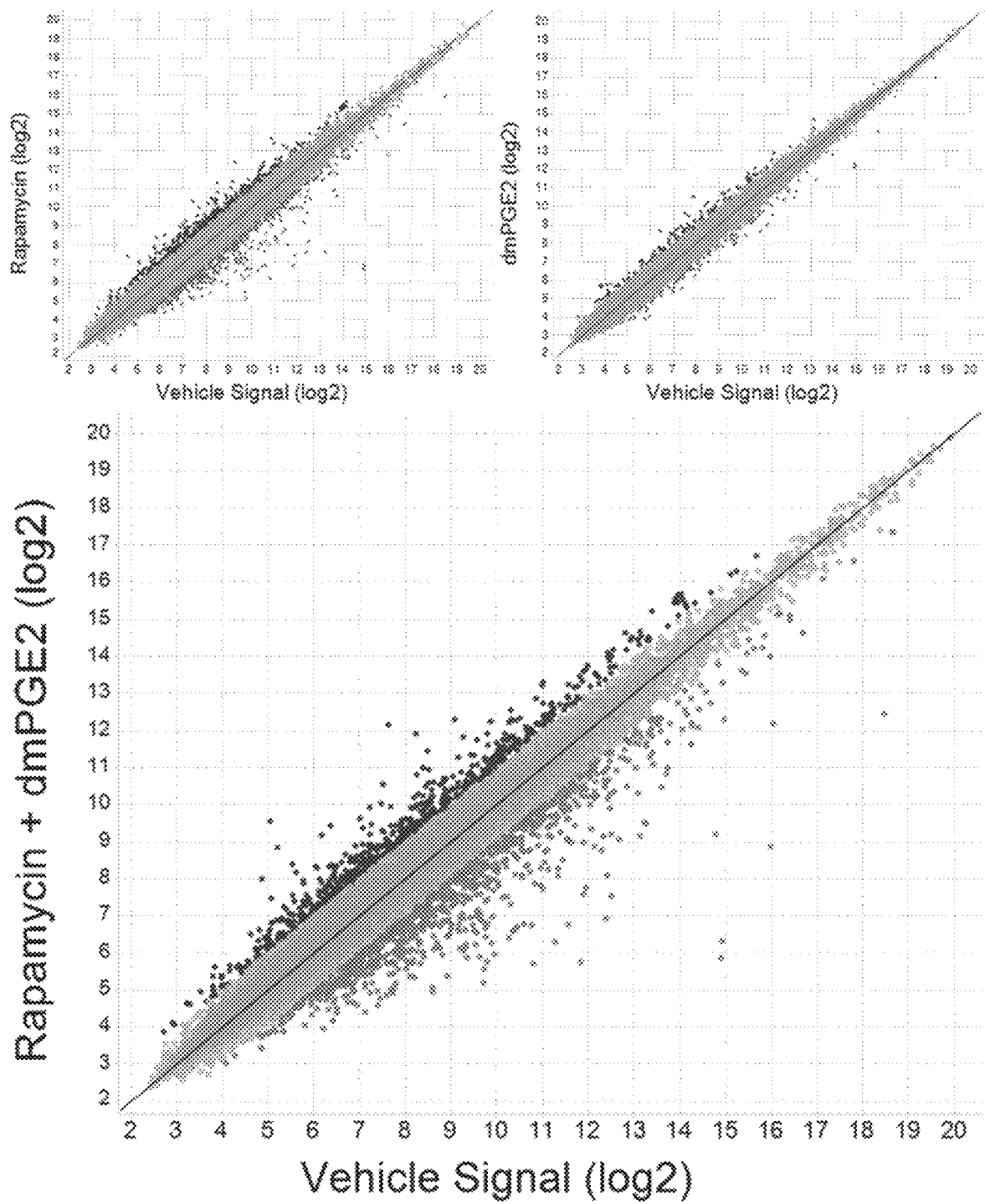
FIGS. 7A-7B show genome-wide expression characterization of CD8+ T-cells under different compound treatment.
Figure 7B:
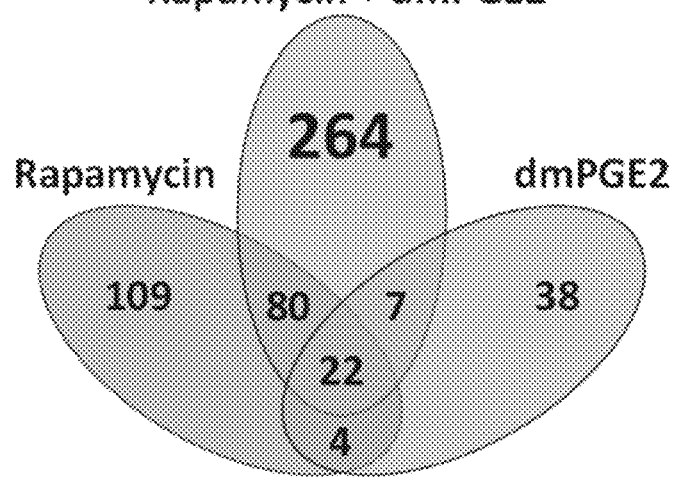
Figure 7B:
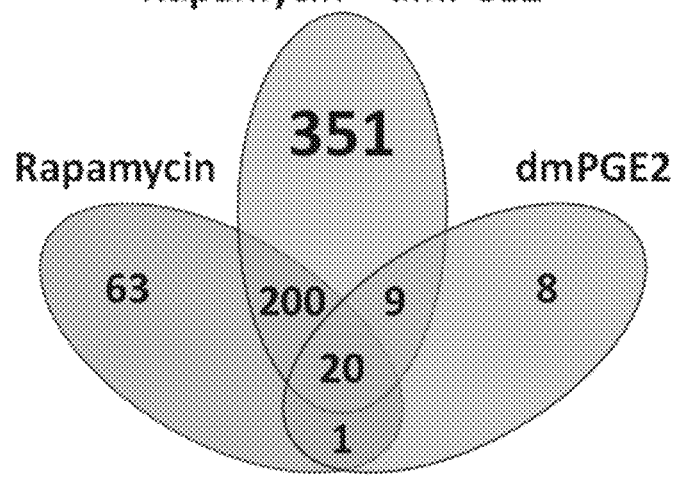

To characterize the genome-wide impact of rapamycin and dmPGE2 treatment individually or in combination during the in vitro T cell expansion process, RNA from cells that are transduced and treated as described in Example 5 was extracted and analyzed on Human Transcriptome Array gene (microarray) chips (Affymetrix, Santa Clara, CA), and the results were compared to a vehicle treated sample. FIG. 7A depicts the genome-wide transcription profiling using microarray chips to show the transcriptional changes of gene probes induced by the small molecules individually and in combination. As shown schematically in FIG. 7B, it is notable that the total number of genes that are up-regulated more than 2 fold compared to vehicle control under the rapa+dmPGE2 treatment is 377, whereas this number is 215 and 71 under the treatment of rapamycin only and dmPGE2 only, respectively. Among the 377 upregulated genes, 264 genes are uniquely upregulated by the combination treatment, but not by either individual compound treatment. As to the down-regulated genes, a total of 581 genes are down-regulated more than 2 fold compared to vehicle control under the rapa+dmPGE2 treatment; whereas only 284 and 38 genes are down-regulated under the rapamycin only and dmPGE2 only treatment, respectively. Among the 581 down-regulated genes, 351 genes are uniquely down-regulated by the combo treatment, but not by either individual compound treatment. The differential gene expression profile under single or combinational compound treatment demonstrates that the combined treatment using both small molecules has a profound transcriptional effect which is significantly greater than the sum of each individual treatment, indicating a synergistic response in the presence of both pathway modulators.

Figure 8:
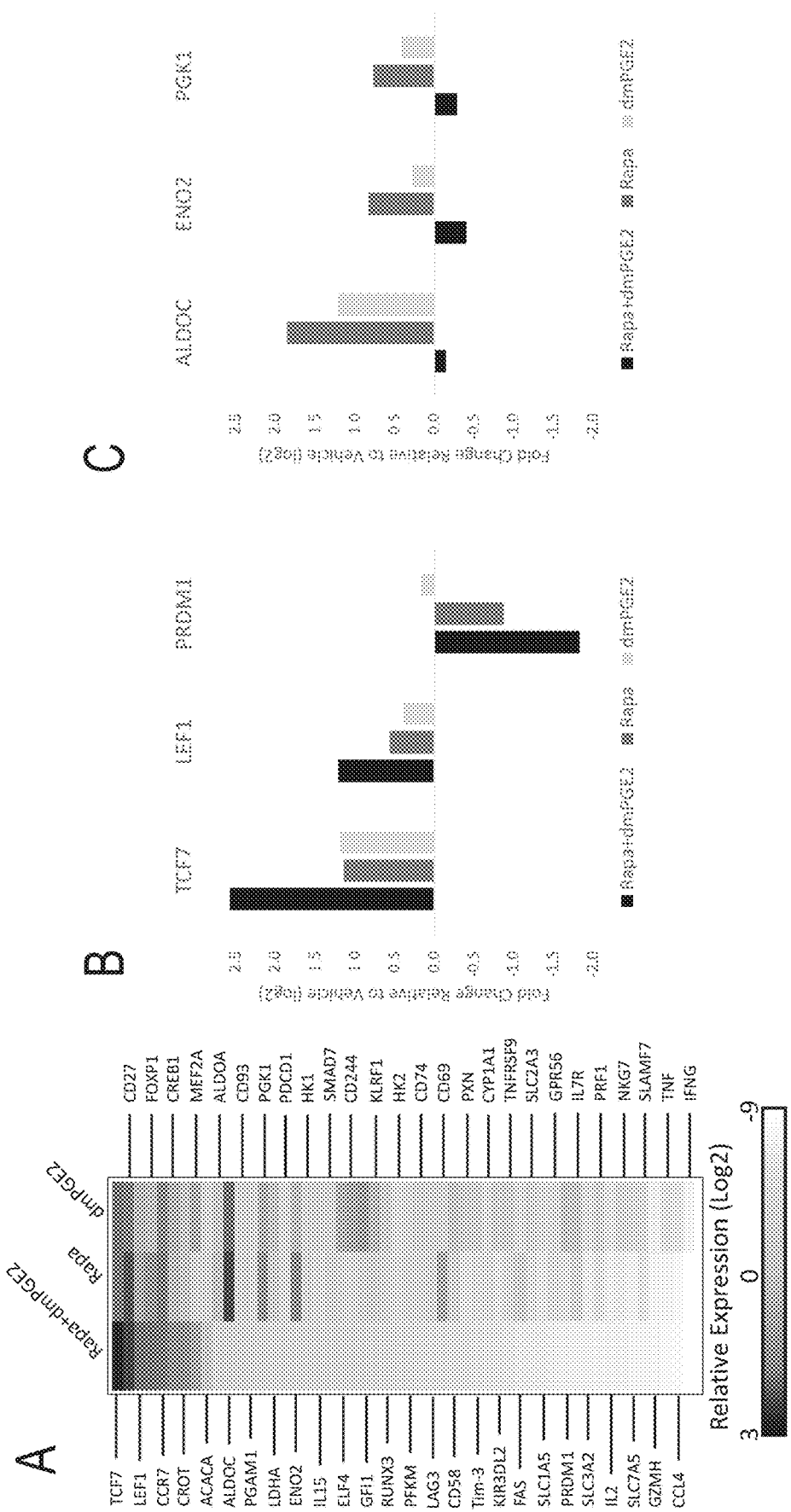
FIG. 8 shows expression level comparison of genes relevant to T cell function, differentiation, and metabolism in T cells treated with rapamycin, dmPGE2, and rapamycin+dmPGE2 combination, respectively. A. Transcriptional changes on many T cell genes that are related to a memory phenotype as well metabolism. B. Transcriptional change of TCF7, LEF1, BLIMP-1 (or PRDM1). C. Transcriptional change of ALDOC, ENO and PGK1 genes under different treatment.

Some exemplary key genes relevant to T cell function (such as cytokine secretion, cytotoxicity, exhaustion, costimulation), differentiation (such as cell development, maturation, and memory cell phenotype) and metabolism (such as glycolysis, amino acid metabolism, cell proliferation) that are differentially expressed under the single or combinational compound treatments are shown in FIG. 8A, and Table 4.

TABLE 4

Relevant genes that are differentially expressed under the single or combinatorial compound treatments

| | Gene | Protein Name | UniProtKB/Swiss-Prot Entry Identifier |
|---|---|---|---|
| 1 | TCF7 | Transcription factor 7 | P36402 |
| 2 | CD27 | CD27 antigen | P26842 |
| 3 | LEF1 | Lymphoid enhancer-binding factor 1 | P27782 |
| 4 | FOXP1 | Forkhead box protein P1 | Q9H334 |
| 5 | CCR7 | C-C chemokine receptor type 7 | P32248 |
| 6 | CREB1 | Cyclic AMP-responsive element-binding protein 1 | P16220 |
| 7 | CROT | Peroxisomal carnitine O-octanoyltransferase | Q9UKG9 |
| 8 | MEF2A | Myocyte-specific enhancer factor 2A | Q02078 |
| 9 | ACACA | 5'-AMP-activated protein kinase catalytic subunit alpha-1 | Q13131 |
| 10 | ALDOA | Fructose-bisphosphate aldolase A | P04075 |
| 11 | ALDOC | Fructose-bisphosphate aldolase C | P09972 |
| 12 | CD93 | Complement component C1q receptor | Q9NPY3 |
| 13 | PGAM1 | Phosphoglycerate mutase 1 | P18669 |
| 14 | PGK1 | Phosphoglycerate kinase 1 | P00558 |
| 15 | LDHA | L-lactate dehydrogenase A chain | P00338 |
| 16 | PDCD1 | Programmed cell death 1 ligand 1 | Q9NZQ7 |
| 17 | ENO2 | Gamma-enolase | P09104 |
| 18 | HK1 | Hexokinase-1 | P19367 |
| 19 | IL15 | Interleukin-15 | P40933 |
| 20 | SMAD7 | Mothers against decapentaplegic homolog 7 | O15105 |
| 21 | ELF4 | ETS-related transcription factor Elf-4 | Q99607 |
| 22 | CD244 | Natural killer cell receptor 2B4 | Q9BZW8 |
| 23 | GFI1 | Zinc finger protein Gfi-1 | Q99684 |
| 24 | KLRF1 | Killer cell lectin-like receptor subfamily F member 1 | Q9NZS2 |
| 25 | RUNX3 | Runt-related transcription factor 3 | Q13761 |
| 26 | HK2 | Hexokinase-2 | P52789 |
| 27 | PFKM | ATP-dependent 6-phosphofructokinase | P08237 |
| 28 | CD74 | HLA class II histocompatibility antigen gamma chain | P04233 |
| 29 | LAG3 | Lymphocyte activation gene 3 protein | P18627 |
| 30 | CD69 | Early activation antigen CD69 | Q07108 |
| 31 | CD58 | Lymphocyte function-associated antigen 3 | P19256 |
| 32 | PXN | Paxillin | P49023 |
| 33 | Tim-3 | T-cell immunoglobulin and mucin domain-containing protein 3T cell immunoglobulin mucin | Q8TDQ0 |
| 34 | CYP1A1 | Cytochrome P450 1A1 | P04798 |
| 35 | KIR3DL2 | Killer cell immunoglobulin-like receptor 3DL2 | P43630 |
| 36 | TNFRSF9 | Tumor necrosis factor receptor superfamily member 9 | Q07011 |
| 37 | FAS | Tumor necrosis factor receptor superfamily member 6 | P25445 |
| 38 | SLC2A3 | Solute carrier family 2, facilitated glucose transporter member 3 | P11169 |
| 39 | SLC1A5 | Neutral amino acid transporter B | Q15758 |
| 40 | GPR56 | Adhesion G-protein coupled receptor G1 | Q9Y653 |
| 41 | PRDM1 | PR domain zinc finger protein 1 | O75626 |
| 42 | IL7R | Interleukin-7 receptor subunit alpha | P16871 |
| 43 | SLC3A2 | 4F2 cell-surface antigen heavy chain | P08195 |
| 44 | PRF1 | PRF1 | P14222 |
| 45 | IL2 | Interleukin-2 | P60568 |
| 46 | NKG7 | Protein NKG7 | Q16617 |
| 47 | SLC7A5 | Large neutral amino acids transporter small subunit 1 | Q01650 |
| 48 | SLAMF7 | SLAM family member 7 | Q9NQ25 |
| 49 | GZMH | Granzyme H | P20718 |
| 50 | TNF | Tumor necrosis factor | P01375 |
| 51 | CCL4 | C-C motif chemokine 4 | P13236 |
| 52 | IFNG | Interferon gamma | P01579 |

Example 10—Gene Panel Characterization of CD8+1-Cells Treated with Rapa+dmPGE2

To further characterize the impact of both small molecules in combination on the expression changes for a panel of genes important for T cell maturation, total RNA was extracted from cells transduced and prepared as in Example 5. The RNA was analyzed on Affymetrix human transcriptome arrays and fold changes (relative to vehicle treatment) of the genes in the panel were determined. The inclusion of both small molecules had a profound transcriptional impact on many key T cell genes some of which are known to promote a memory phenotype as well impacting metabolism (FIG. 8A). Treatment with both rapamycin and dmPGE2 resulted in synergistic effects for both transcription factor genes (FIG. 8B), and genes involved in glycolysis (FIG. 8B). The transcription factors TCF7 and LEF1 are important for the generation of functional memory cells (Zhou et al., J Immunol. 2012; 189(6): 2722-2726), and treatment with both rapamycin and dmPGE2 increased the expression of these genes more than either compound alone (FIG. 8B). BLIMP-1 is a transcriptional repressor gene expressed in terminally differentiated and effector memory T cells, and BLIMP-1 deficiency promotes the acquisition of central memory T cell properties (Rutishauser et al., Immunity. 2009; 31(2): 296-308). Treatment with the combination of rapamycin and dmPGE2 resulted in a greater decrease of BLIMP-1 expression compared to either compound alone (FIG. 8B). Interestingly, BLIMP-1 is slightly upregulated when treated with dmPGE2 alone, which is consistent with the observation that dmPGE2 promotes effector T cell differentiation (Sreeramkumar et al., 2015). So it is surprising that the combination treatment using both rapamycin and dmPGE2 not only "corrects" dmPGE2's tendency in driving T cell differentiation, but also achieves a synergistic effect when combined with rapamycin in down-regulating BLIMP-1 expression.

In addition to changes in transcription factor expression, the combination of rapamycin and dmPGE2 also affected the expression of genes involved in metabolism. The genes ALDOC, ENO2, and PGK1 are all involved in different steps of the glycolysis pathway, and the combined treatment with rapamycin and dmPGE2 resulted in down-regulation of these genes (FIG. 8C). In contrast, treatment with either compound alone caused an up-regulation of all three of these glycolysis-related genes (FIG. 8C). Activated T cells preferentially switch to aerobic glycolysis which is more suited for supporting full effector function (Chang et al., Cell. 2013; 153(6): 1239-1251). Induction of high glycolytic activity in CD8+ T cells drives T cells toward a terminally differentiated state rather than memory cells (Sukumar et al., J Clin Invest. 2013; 123(10): 4479-4488). A reduction in the ability of cells treated with rapamycin and dmPGE2 to undergo glycolysis through reduced expression of ALDOC, ENO2, and PGK1, along with the increase in spare respiratory capacity as shown in Example 8, supports the notion that the combination treatment is skewing the cell towards a central memory phenotype.

Example 11—RT-qPCR Quantitation of CCR7 and CD62L in CD8+ T-Cells Treated with Rapa+dmPGE2

Figure 9:
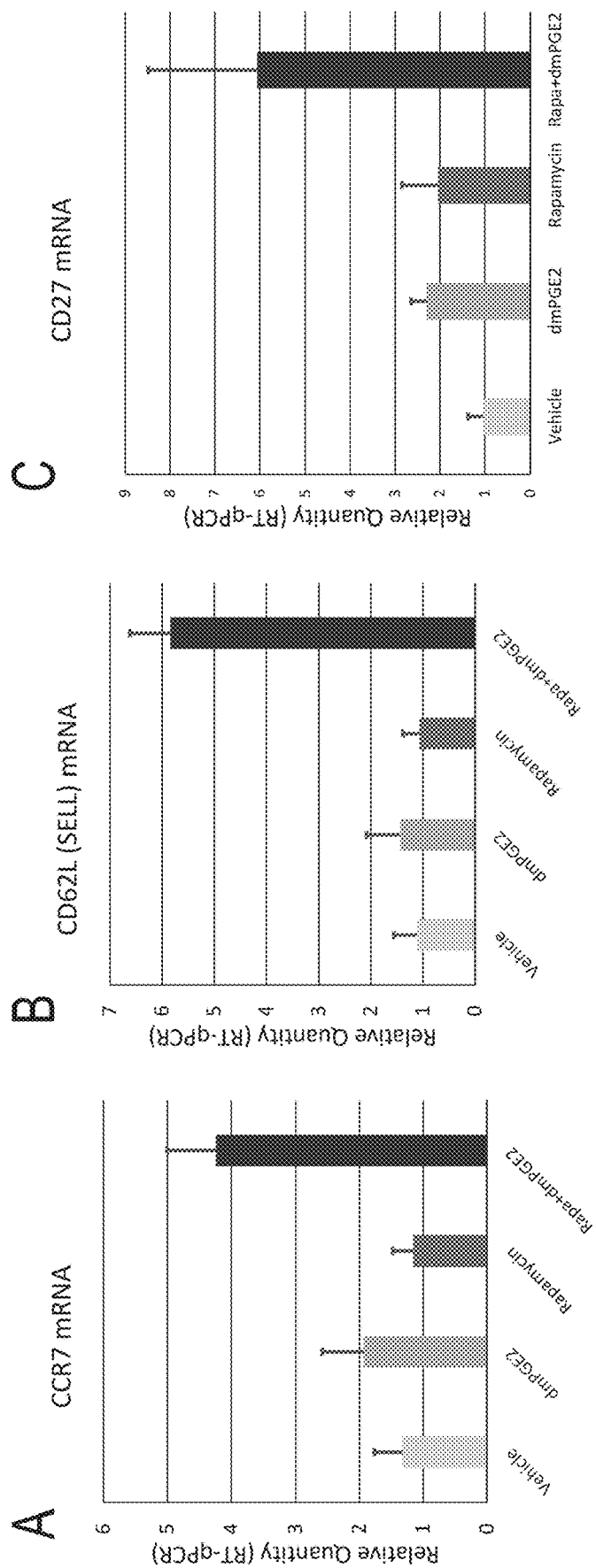
FIG. 9 shows RT-qPCR quantitation of memory cell marker genes in CD8+ T-cells treated with treated with DMSO, rapamycin, dmPGE2, and rapamycin+dmPGE2 combination. A: CCR7 mRNA quantification. B: CD62L mRNA quantification. C: CD27 mRNA quantification.

To further characterize the impact of rapa+dmPGE2 in memory cell skewing, the expression changes for two key genes, CCR7 and CD62L, known to be highly expressed in memory T cells were investigated. The total RNA was extracted from cells treated with compounds as described in Example 5. The RNA was analyzed using RT-qPCR and TaqMan gene expression assays specific to each gene. Relative quantitation of each gene transcript was determined for each in vitro treatment. FIGS. 9A and 9B show the dramatic increase in expression of both key memory T cell genes with rapa+dmPGE2 treatment, while the individual compounds induced relatively minimal transcriptional increases for both of these genes. FIG. 9C showed a similar effect of rapa+dmPGE2 treatment on CD27 gene expression, which corroborates the cell surface expression of CD27 in Example 5 and FIG. 3. The observed requirement for both rapamycin and dmPGE2 implies a synergistic response between pathways to promote the expressional changes towards a memory T cell.

Example 12—Treatment with Rapa+dmPGE2 Improves CAR-T Cell Expansion in a Serial Killing Assay A critical prognostic marker of CAR-T cell therapy in clinical trials is the expansion of the CAR-T cells in the patient post-treatment (Porter et al. 2015). An in vitro serial killing assay, where CAR-T cells are allowed to "clear" tumor cells in vitro over multiple rounds, is a model that can assess CAR-T expansion in the presence of tumor cells that express the antigen recognized by the CAR. To this end, CD8 T cells were transduced to obtain CAR-T cells, and treated as in Example 5, then cryopreserved. After thawing, the CAR-T cells were co-cultured with Nalm6 tumor cells that express endogenous CD19 and transgenic mKate2, a far-red fluorescent protein. Expression of eGFP in the CAR-T cells and mKate2 in the Nalm6 target cells allows easy and reliable identification and counting of both cell types in the serial killing assay. Prior to starting each round of killing, cell numbers were adjusted so that the same ratio of CAR-T cell to Nalm6 target cell was maintained across the CAR-T cell cultures generated from different compound treatments.

Figure 10:
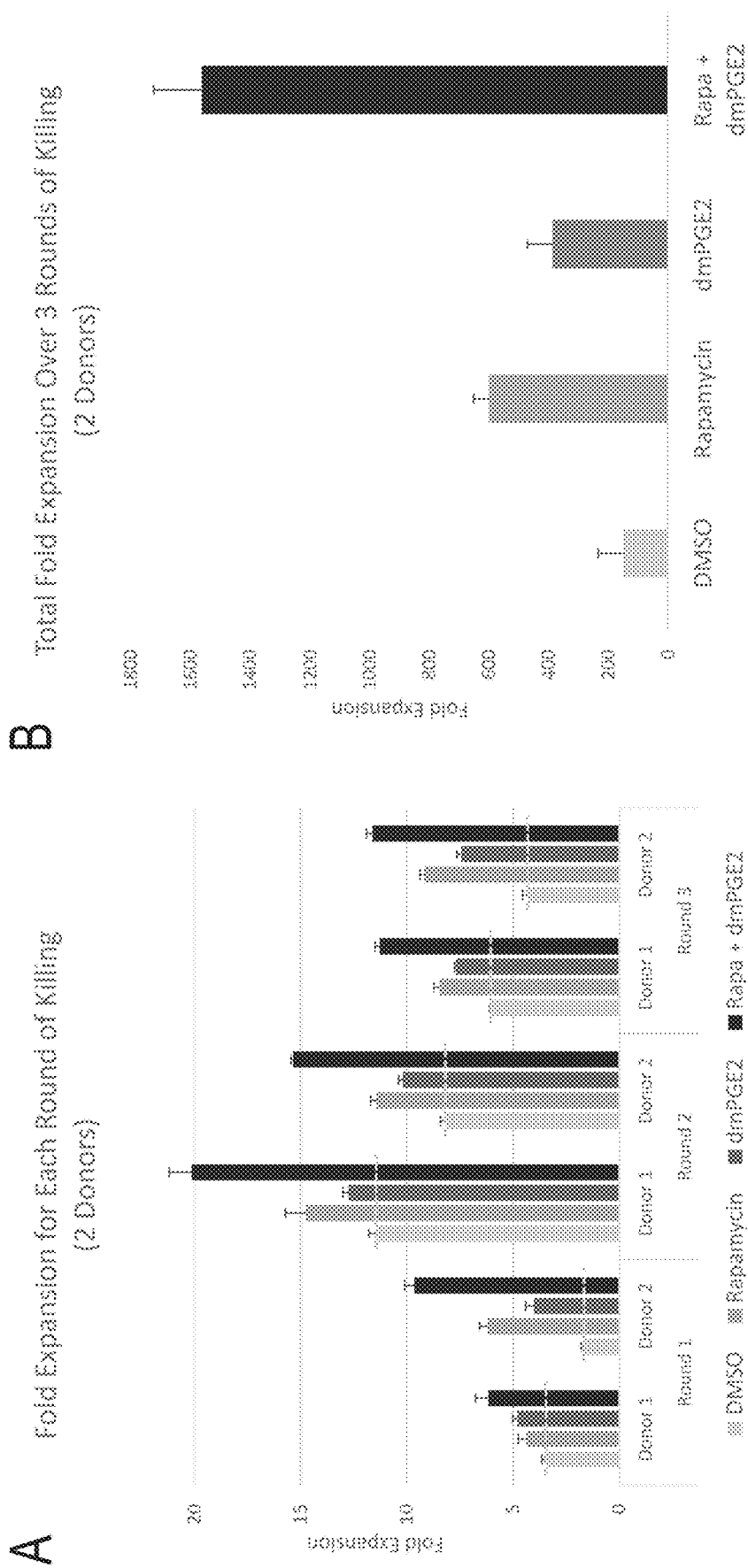
FIG. 10 shows in vitro serial killing assay to assess CAR-T cell expansion in the presence of tumor cells, and the CAR-T cells were treated with DMSO, rapamycin, dmPGE2, and rapamycin+dmPGE2 combination. A: Fold expansion of CAR-T cells for each round of killing. B: Comparison of total fold expansion of treated CAR-T cells over 3 rounds of killing.
Figure 11:
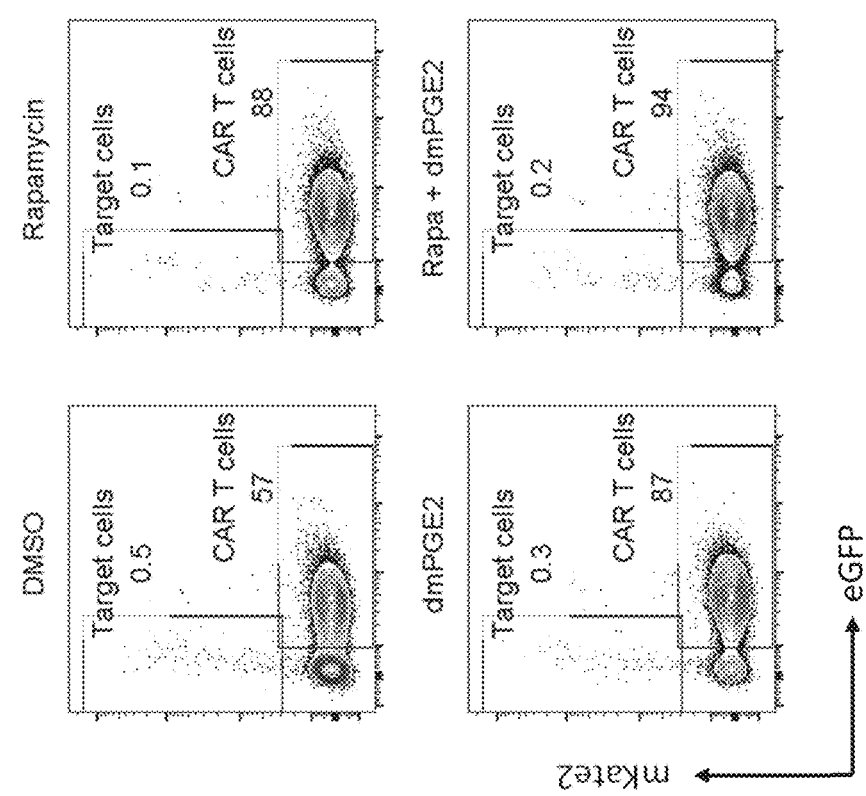
FIG. 11 shows the killing ability of the CAR-T cells in vitro was unaffected in the three rounds of killing assays. A: CAR-T cells previously treated with rapa (abbreviation for "rapamycin"), dmPGE2, or rapa+dmPGE2 all cleared target cells over time. B: Flow cytometry analysis of viable cells in the co-cultures show very few target cells remaining under vehicle, rapamycin, dmPGE2, and rapamycin+dmPGE2 combination.

FIG. 10A shows the fold expansion of CAR-T cells from two donors after each round of tumor cell killing. CAR-T cells treated with rapa+dmPGE2 show consistently improved expansion relative to vehicle or either compound individually. When total expansion over all three rounds of serial killing is determined (FIG. 10B), rapa+dmPGE2 shows much greater expansion than either compound individually indicating a potential synergistic effect in this critical parameter. Despite the observed difference in expansion, the ability of the CAR-T cells to kill tumor cells in vitro was unaffected for three rounds of in vitro killing. CAR-T cells previously treated with rapa, dmPGE2, or rapa+dmPGE2 successfully cleared target cells over time (FIG. 11A). At the end of round three, flow cytometry analysis of viable cells in the co-cultures show very few mKate2 positive cells for vehicle and all compound-treated cells (FIG. 11B).

Figure 12:
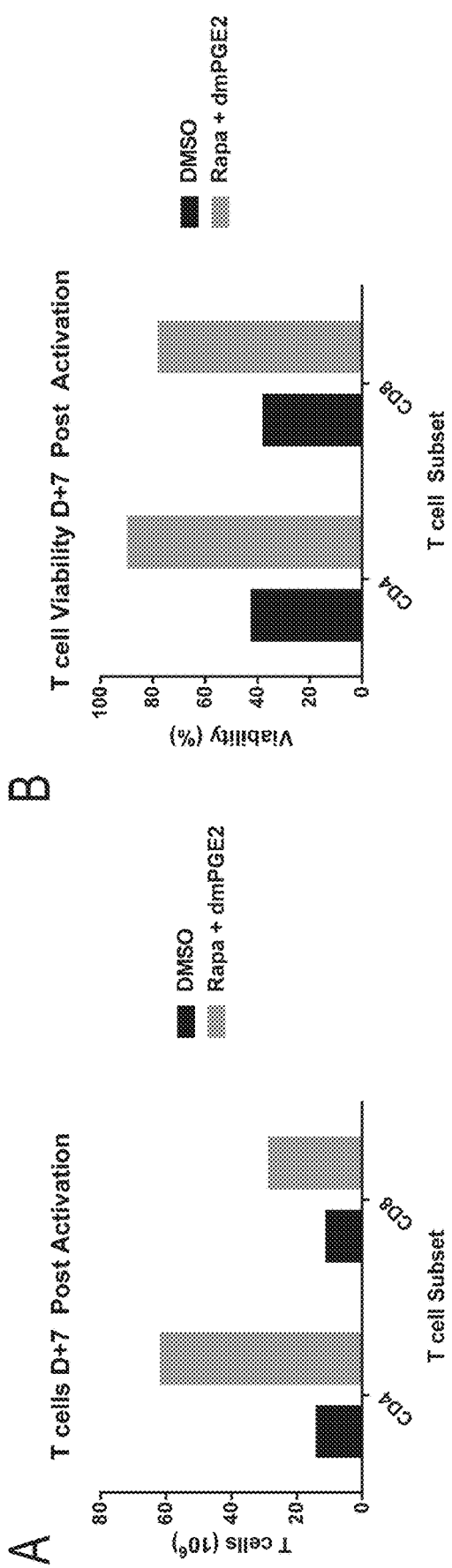
FIG. 12 shows the effect of adding rapamycin and dmPGE2 in combination to CD4 and CD8 T cell in larger-scale culture format at 1 week post activation. A: increased expansion relative to DMSO. B: Increased viability relative to DMSO.

Example 13—Demonstration of Improved CAR-T Cell Expansion with Rapa+dmPGE2 in Larger-Scale Culture Format To determine the effect of rapa+dmPGE2 on CD4 T cells and to demonstrate that the increased expansion of rapa+dmPGE2 would scale to larger expansion formats, CD4 and CD8 T cells were separately activated and expanded in vitro. The cells were transduced with the CAR-2 construct (FIG. 2) one day after activation and then replated into 24-well GREX plates with or without compounds. Half the media was replaced every two days thereafter until harvest one week post activation. FIG. 12 demonstrates that the addition of rapa+dmPGE2 results in increased CD4 and CD8 T cell expansion (FIG. 12A) and viability (FIG. 12B) at one week post activation relative to DMSO.

Example 14—Improved In Vivo Efficacy of Rapa+dmPGE2-Treated CAR-T Cells

Figure 13A:
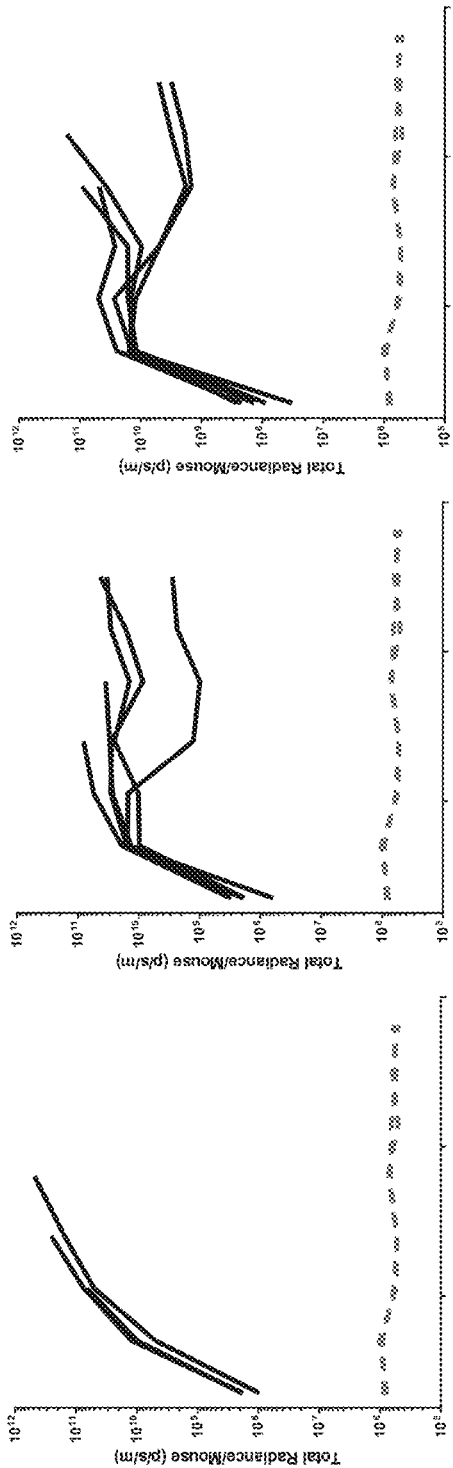
FIGS. 13A-13B show improved in vivo efficacy of rapa+dmPGE2-treated CAR-T cells.
Figure 13A:
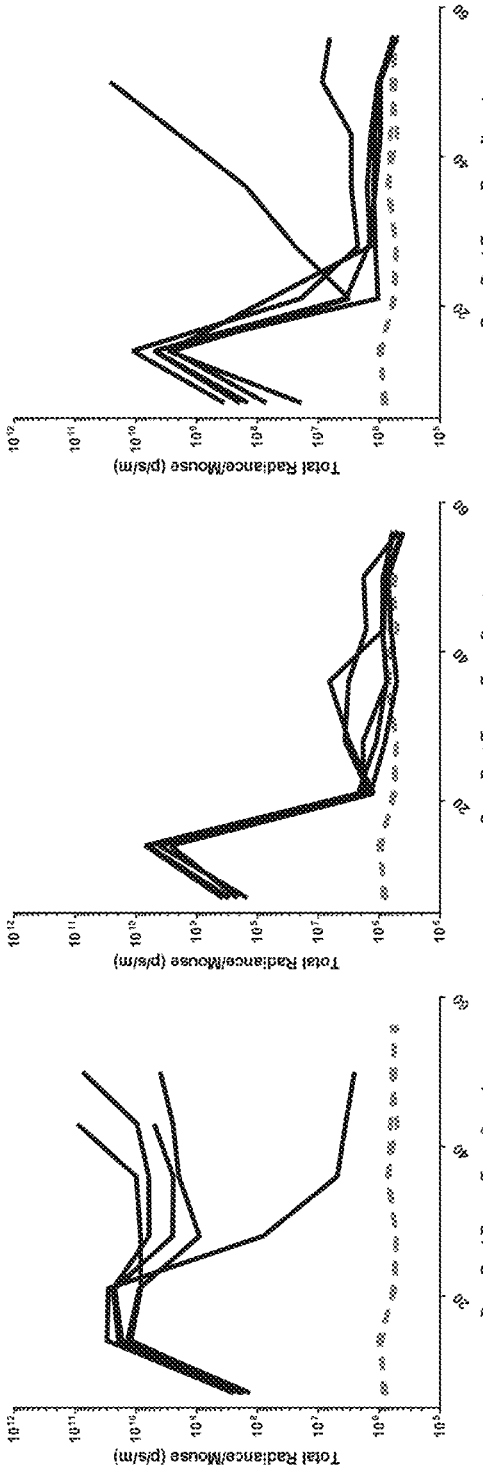

To determine whether rapa+dmPGE2 treatment increased the in vivo tumor clearance and persistence of CAR-T cells NSG mice were injected with Nalm-6-luc, a CD19+ human tumor line engineered to express firefly luciferase. CAR-T cells were generated from CD4+ and CD8+ T cells that were separately activated and expanded in vitro. The cells were transduced with the CAR-2 construct (FIG. 2) one day after activation and then replated into 24-well GREX plates with or without the compounds. Half the media was replaced every two days thereafter until harvest one week post-activation. One week after tumor injection, the NSG mice were treated with $0.2 \times 10^6$ CD4 and CD8 CAR-T cells mixed at a 1:1 ratio via retroorbital injection. The mice were imaged periodically to determine tumor burden. FIG. 13A shows that CAR-T cells treated with rapa+dmPGE2 or the PI3K inhibitor PI-103 were able to clear tumor from the majority of mice while those treated with untransduced T cells, or CAR-T cells treated with DMSO, U0126 or TWS119, demonstrated minimal tumor control.

Figure 13B:
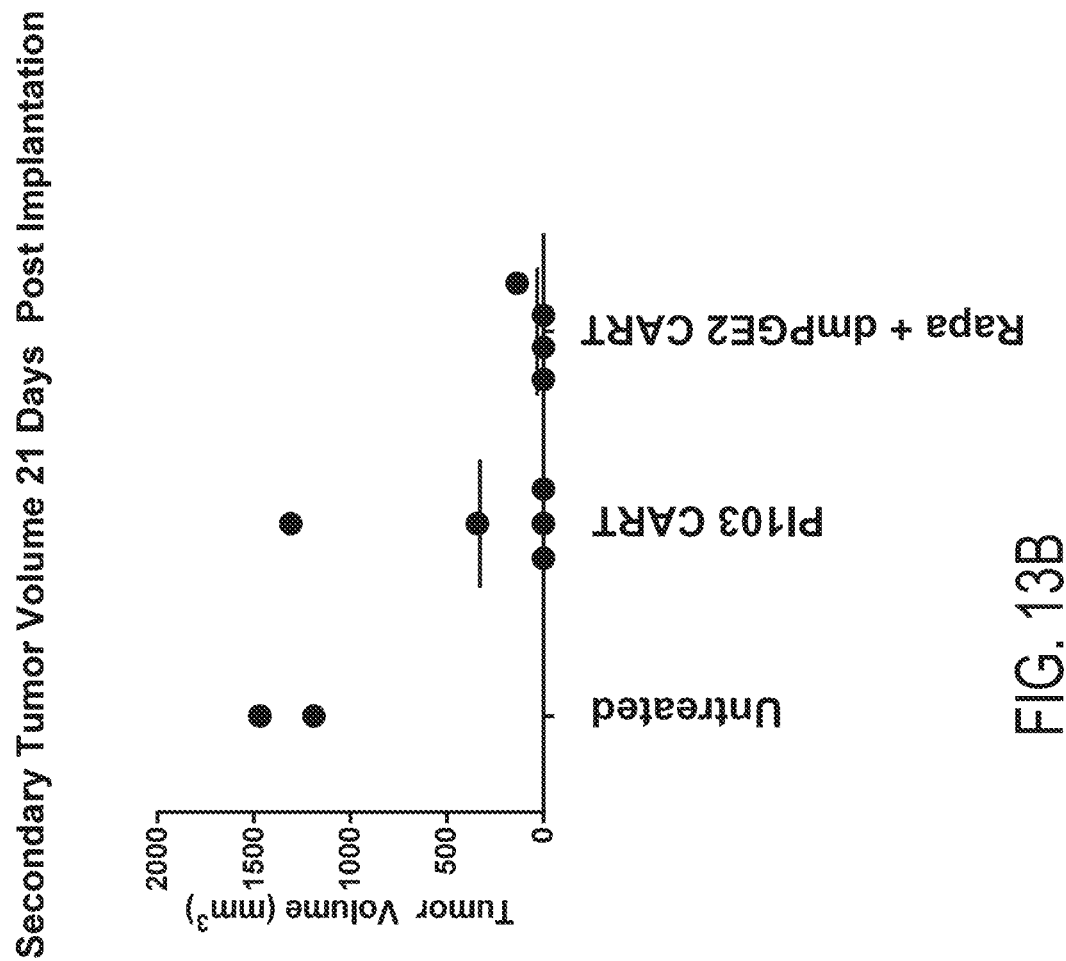
Figure 14:
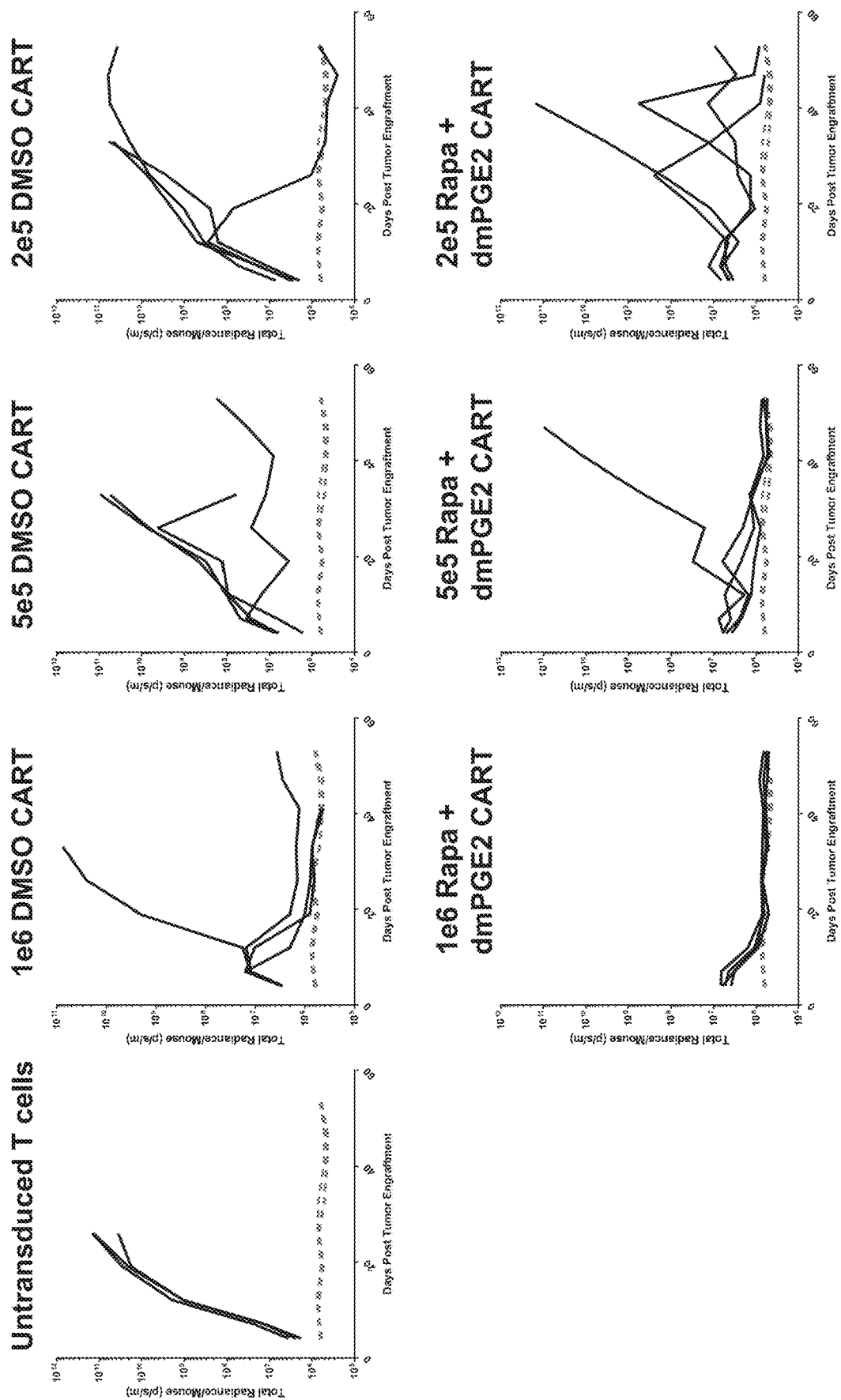
FIG. 14 shows rapa+dmPGE2 treatment increased the in vivo tumor clearance and persistence of CAR-T cells after cryopreservation.

Example 15—Improved Secondary Tumor Anti-Tumor Response with Rapa+dmPGE2-Treated CAR-T Cells To determine whether the CAR-T cells that mediated initial tumor clearance were able to persist and provide long-term protection, the mice that survived primary tumor challenge (Example 14) were rechallenged with K562-CD19, a human myelogenous leukemia line engineered to express CD19, 60 days after the primary tumor injection. The only two groups that had mice that survived until the start of this rechallenge study were the rapa+dmPGE2 and PI-103-treated cohorts. FIG. 13B shows that at 21 day post challenge with secondary tumor 75% (¾) of the rapa+dmPGE2-treated CAR-T mice and 60% (⅗) of the PI103 CAR-T-treated mice had no detectable tumor.

Example 16—Improved In Vivo Efficacy of Cryo-Preserved Rapa+dmPGE2-Treated CAR-T Cells To determine whether rapa+dmPGE2 treatment increased the in vivo tumor clearance and persistence of CAR-T cells after cryopreservation, we injected NSG mice with $0.5 \times 10^6$ Nalm-6-luc, a CD19 expressing human tumor line that was engineered to express firefly luciferase. Four days later mice were treated with $1.0 \times 10^6$, $0.5 \times 10^6$ or $0.2 \times 10^6$ CD4 and CD8 CAR-T cells mixed at a 1:1 ratio. CAR-T cells were generated from CD4+ and CD8+ T cells that were separately activated and expanded in vitro as described in Example 14. The cells were transduced with the CAR-2 construct (FIG. 2) one day after activation and then replated into 24-well GREX plates with or without compounds. Half the media was replaced every two days thereafter until harvest one week post activation. Cells were cryopreserved and then thawed for use. NSG mice were infused with tumor cells followed one week later by CAR-T transfer via retroorbital injection.

Figure 15:
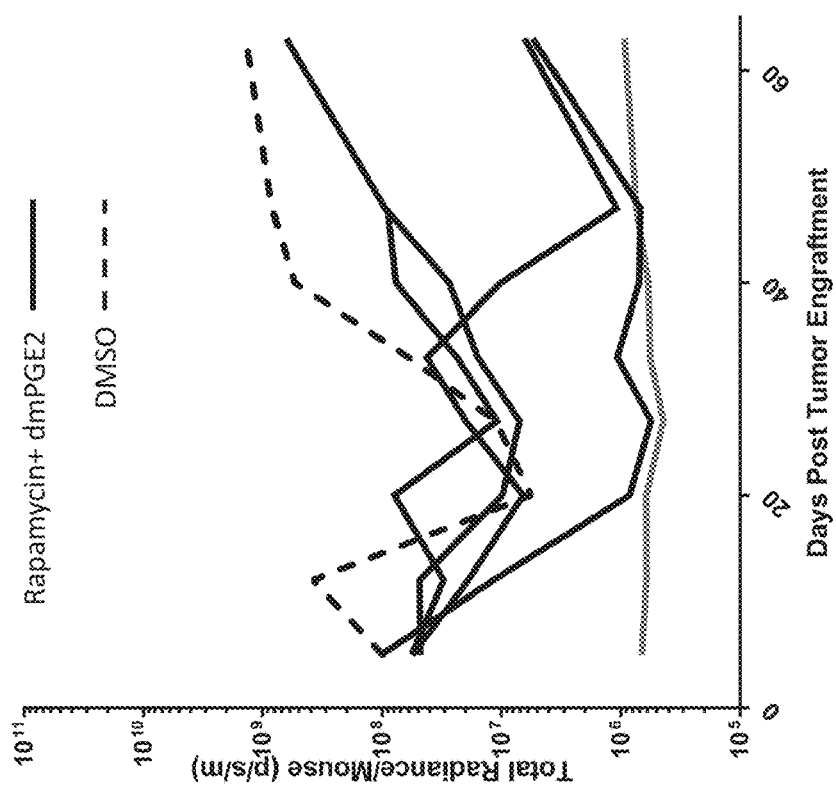
FIG. 15 shows tumor clearance and persistence of suboptimal doses of CAR-T cells under (A) rapa and (B) rapa+dmPGE2 treatment.
Figure 15:
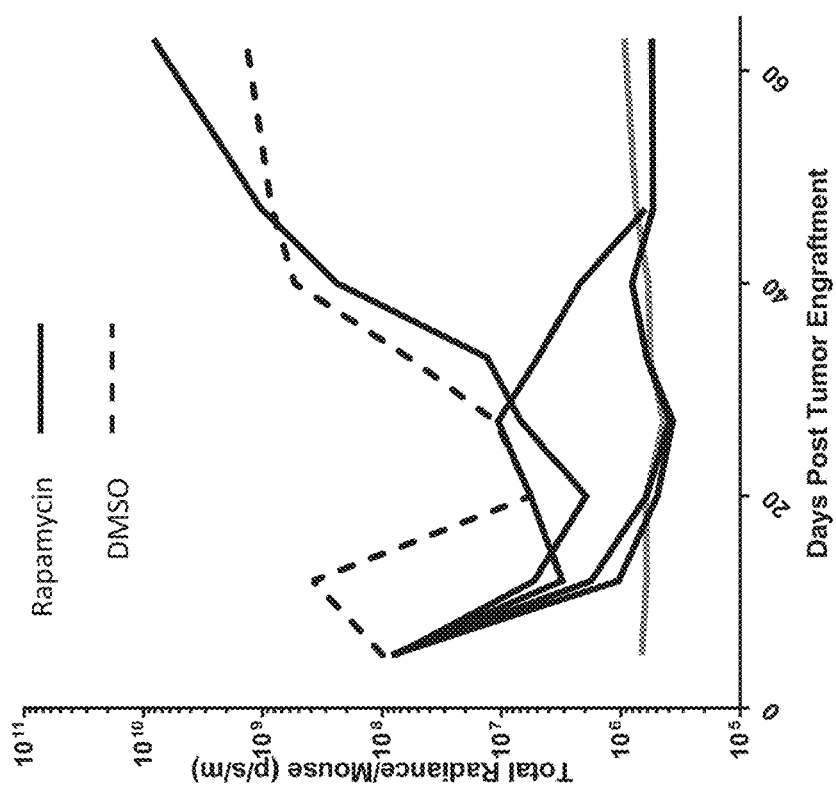

In one experiment, a suboptimal dose of CAR-T cells ($0.2 \times 10^6$) that had been grown in the presence of (1) DMSO; (2) Rapamycin; or (3) Rapamycin and $dmPGE_2$ (right panel, solid line) were injected into the tumor-bearing mice. CAR-T cells treated with Rapamycin (FIG. 15A) or Rapamycin and dmPGE2 (FIG. 15B) were able to reduce tumor burden within a week of adoptive transfer while CAR-T cells treated with DMSO were not. No mice injected with DMSO-treated CAR-T cells were able to reduce tumor burden below detection and all mice failed to have sustained anti-tumor responses and relapsed (FIGS. 15A and 15B). As shown in FIG. 15A, one of four mice injected with Rapamycin-treated CAR-T cells relapsed. The other three injected with Rapamycin-treated CAR-T cells were able to reduce tumor burden below detection, and one of those three mice was able to sustain long-term anti-tumor responses while the other two of the three with undetectable tumor burden did not survive beyond 30 and 45 days, respectively (FIG. 15A). Among the four mice injected with Rapamycin and dmPGE2-treated CAR-T cells, two of the four were able to sustain long-term anti-tumor responses, while the other two relapsed. One of the two mice which sustained long-term anti-tumor responses was able to reduce tumor burden below detection. All four mice injected with Rapamycin and dmPGE2-treated CAR-T cells survived beyond 60 days.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composition, wherein the composition is a culture medium comprising a combination,
    wherein the combination comprises (a) a mammalian target of rapamycin (mTOR) inhibitor, and (b) dimethyl prostaglandin E2 (dmPGE2) or an analogue or derivative thereof; and
    wherein the combination is present in an amount effective to modulate a population of T cells to (a) reduce expression of one or more T cell exhaustion markers, or (b) increase mitochondrial spare respiratory capacity, in comparison to a corresponding population of T cells that are not modulated with the combination.

2. The composition of claim 1, wherein the one or more T cell exhaustion markers comprise one or more of PD-1 and Tim-3.

3. The composition of claim 1, wherein the combination is present in an amount effective to (a) increase a central memory T cell subpopulation of the population of T cells, and (b) decrease an effector T cell subpopulation of the population of T cells.

4. The composition of claim 1, further comprising the population of T cells.

5. The composition of claim 4, wherein the population of T cells comprises (a) increased gene expression in at least one of CD27, C-C chemokine receptor type 7 (CCR7), CD62L, transcription factor 7 (TCF7), lymphoid enhancer-binding factor 1 (LEF1), and (b) decreased gene expression in at least one of PR domain zinc finger protein 1 (BLIMP- 1), fructose-bisphosphate aldolase C (ALDOC), gamma enolase (ENO2), PD-1 and Tim-3, in comparison to a corresponding population of T cells that are not modulated with the combination.

6. The composition of claim 4, wherein the population of T cells comprises increased spare respiratory capacity (SRC) in comparison to a corresponding population of T cells that are not modulated with the composition.

7. The composition of claim 4, wherein the population of T cells comprises at least one of the following:
   (a) increased gene expression in at least one of CD27, CCR7, CD62L, TCF7, and LEF1;
   (b) decreased gene expression in at least one of BLIMP-1, ALDOC, ENO2, and PGK1;
   (c) increased central memory T cell subpopulation;
   (d) decreased effector T cell subpopulation; and
   (e) improved capability in tumor clearance and persistence;
   compared to a corresponding population of T cells that are not modulated with the composition.

8. The composition of claim 4, wherein T cells of the population of T cells comprise at least one genetic modification.

9. The composition of claim 8, wherein the at least one genetic modification comprises an insertion, a deletion, or a nucleic acid replacement.

10. The composition of claim 8, wherein the at least one genetic modification comprises an exogenous nucleic acid encoding a T Cell Receptor (TCR) and/or a Chimeric Antigen Receptor (CAR).

11. The composition of claim 8, wherein the at least one genetic modification comprises insertion or modification of a sequence encoding at least one of a safety switch protein, a targeting modality, a receptor, a signaling molecule, a transcription factor, a pharmaceutically active protein or peptide, a drug target candidate, or a protein promoting one or more activities; wherein the one or more activities comprise one or more of engraftment, trafficking, homing, viability, self-renewal, persistence, immune response regulation and modulation, and survival of the T cells.

12. The composition of claim 8, wherein the at least one genetic modification comprises deletion or reduced expression of B2M, TAP1, TAP2, Tapasin, NLRC5, PD1, LAG3, TIM3, RFXANK, CIITA, RFX5, or RFXAP, or any gene in the chromosome 6p21 region.

13. The composition of claim 8, wherein the at least one genetic modification comprises introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

14. The composition of claim 8, wherein the population of T cells are differentiated in vitro from stem cells, hematopoietic stem or progenitor cells, or progenitor cells; and wherein the stem cells, hematopoietic stem or progenitor cells, or progenitor cells comprise the at least one genetic modification.

15. The composition of claim 14, wherein the stem cells comprise induced pluripotent stem cells (iPSCs) or embryonic stem cells (ESCs).

16. The composition of claim 14, wherein the progenitor cells are CD34+ hemogenic endothelium cells, multipotent progenitor cells, or T cell progenitor cells.

\* \* \* \* \*